United States Patent [19]

Haslanger et al.

[11] Patent Number: 4,463,015
[45] Date of Patent: Jul. 31, 1984

[54] ARYL SUBSTITUTED 7-OXABICYCLOHEPTANE COMPOUNDS, USEFUL IN INHIBITING PLATELET AGGREGATION

[75] Inventors: Martin F. Haslanger, Lambertville; Masami Nakane, Plainsboro, both of N.J.

[73] Assignee: E. R. Squibb & Sons, Inc., Princeton, N.J.

[21] Appl. No.: 409,192

[22] Filed: Aug. 18, 1982

[51] Int. Cl.$^3$ .................... A61K 31/34; C07D 307/00
[52] U.S. Cl. .................... 424/285; 424/244; 424/267; 424/274; 549/463; 549/60; 546/269; 548/525
[58] Field of Search ............ 549/463; 542/416, 418, 542/420, 430, 432, 400, 471; 424/244, 267, 274, 285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/458 |
| 4,228,180 | 10/1980 | Sprague | 424/285 |
| 4,254,044 | 3/1981 | Sprague | 424/285 |

FOREIGN PATENT DOCUMENTS 0043292 6/1982 European Pat. Off. .
2039909 8/1980 United Kingdom .

*Primary Examiner*—Henry R. Jiles
*Assistant Examiner*—Bernard Dentz
*Attorney, Agent, or Firm*—Lawrence S. Levinson; Burton Rodney

[57] ABSTRACT

7-Oxabicycloheptane and prostaglandin analogs are provided having the structural formula

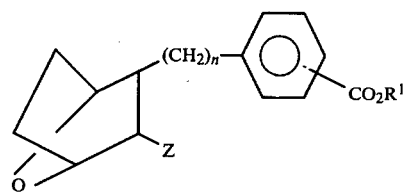

and including all stereoisomers thereof.

The compounds are cardiovascular agents useful, for example, in the treatment of thrombolytic disease.

19 Claims, No Drawings

ARYL SUBSTITUTED 7-OXABICYCLOHEPTANE COMPOUNDS, USEFUL IN INHIBITING PLATELET AGGREGATION

DESCRIPTION OF THE INVENTION

The present invention relates to 7-oxabicycloheptane prostaglandin analogs which are cardiovascular agents useful, for example, in the treatment of thrombolytic disease. These compounds have the structural formula

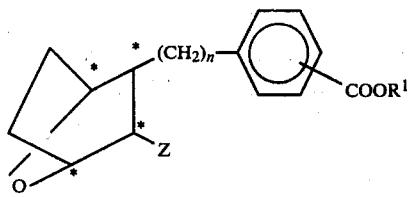

I and including all stereoisomers thereof, wherein

Z is 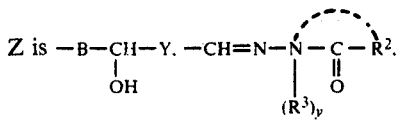

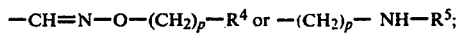

n is 1 or 2;
$R^1$ is H or lower alkyl;
B is —CH=CH—, —C≡C— or $(CH_2)_2$;
Y is alkyl; substituted alkyl; aryl-lower alkyl; alkenyl; alkynyl, aryl; pyridyl; substituted pyridyl; pyridyl-lower alkyl; thienyl, substituted thienyl; thienyl-lower alkyl; cycloalkyl; cycloalkylalkyl; or substituted cycloalkylalkyl;
y is 0 or 1, where y is 1, $R^3$ is H or lower alkyl;
$R^2$ is lower alkyl, lower alkoxy, aryl, alkylamino, arylamino, aryloxy, pyridinyl or cycloalkyl or where y is 0 as indicated by

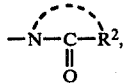

$R^2$ can be a —$(CH)_x$— linking group (wherein x is 3, 4 or 5) which together with

may form an N-containing 5-, 6- or 7-membered heterocycle, with the proviso that when $R^3$ is H, $R^2$ is lower alkoxy;
$R^4$ is lower alkyl, cycloalkyl, aryl, arylalkyl or alkanoyl;
p is 0 to 5;
m is 1 to 8; and
$R^5$ is lower alkyl, lower alkoxy, aralkoxy or

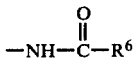

wherein $R^6$ is lower alkyl or phenyl.

Thus, the formula I compounds of the invention include the following:

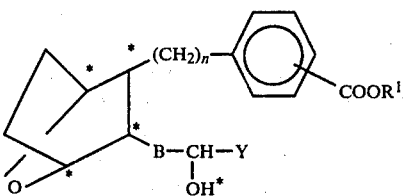

II

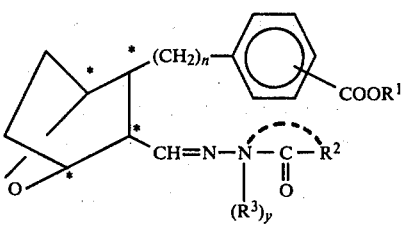

III

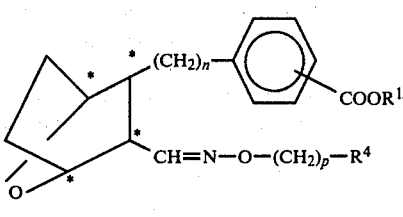

IV and

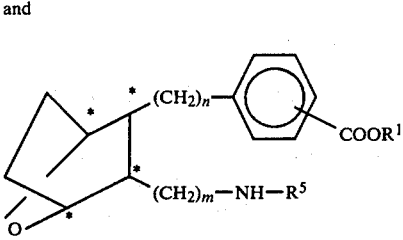

V

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "substituted pyridyl" refers to a pyridyl group substituted with one or two halogen or lower alkyl groups.

The term "substituted thienyl" refers to a thienyl group substituted with one or two halogen or lower alkyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aryloxy" includes any of the above lower alkyl or alkyl group or aryl groups linked to an oxygen atom.

The term "alkylamino" or "arylamino" includes any of the above alkyl groups or aryl groups linked to an amino group.

The term "lower alkenyl" or "alkenyl" refers to an unsaturated hydrocarbon group having from 3 to 6 carbon atoms and a single carbon-carbon double bond. Typical lower alkenyl groups include, for example, 2-propenyl, 1-propenyl, 1-butenyl, 2-butenyl, 3-butenyl and the like.

The term "lower alkynyl" or "alkynyl" refers to an unsaturated hydrocarbon group having from 3 to 6 carbon atoms, and a single carbon-carbon triple bond. Typical alkynyl groups include, for example, 1-propynyl, 1-butynyl, 2-propynyl, 2-butynyl, 3-butynyl and the like.

The term "halogen" or "halo" as used herein refers to chlorine, bromine, fluorine or iodine with fluorine being preferred.

The terms "$(CH_2)_m$", "$(CH_2)_n$" and "$(CH_2)_p$" include a straight or branched chain radical having from 1 to 8 carbons in the normal chain in the case of $(CH_2)_m$, 1 or 2 carbons in the normal chain in the case of $(CH_2)_n$ and 0 to 5 carbons in the case of $(CH_2)_p$, and may contain one or more lower alkyl substituents. Examples of $(CH_2)_m$, $(CH_2)_n$ and $(CH_2)_p$ groups include $CH_2$, $CH_2CH_2$, $(CH_2)_3$, $(CH_2)_4$, $(CH_2)_5$, $(CH_2)_6$, $(CH_2)_7$, $$-(CH_2)_2-\underset{CH_3}{\underset{|}{CH}}-, \quad -CH_2-\underset{CH_3}{\underset{|}{CH}}-, \quad -CH_2-\underset{CH_3}{\underset{|}{CH}}-\underset{CH_3}{\underset{|}{CH}}-CH_2-,$$

$$-CH_2-\underset{CH_3}{\underset{|}{CH}}-CH_2-\underset{CH_3}{\underset{|}{CH}}-,$$

and the like.

Preferred are those compounds of formula II wherein n is 2, $R^1$ is H or methyl, B is —CH=CH—, and Y is $$-\underset{\underset{CH_3}{|}}{\overset{\overset{CH_3}{|}}{C}}-CH_2-CH_2-CH_3,$$

cycloalkyl, especially cyclohexyl, 1-methylcyclohexyl, cycloalkylalkyl,

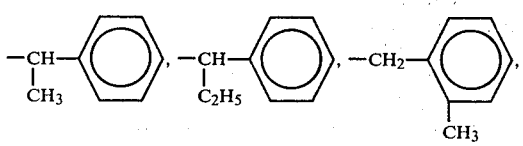

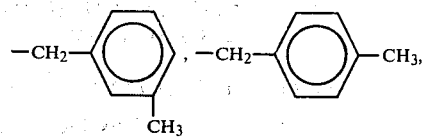

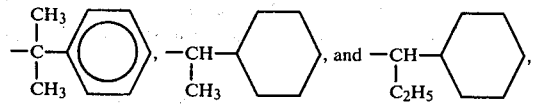

and the $COOR^1$ group is in the para position.

Also preferred are compounds of formula V wherein n is 1, $R^1$ is H or methyl, m is 1 to 3 and $R^5$ is $$-NH-\overset{\overset{O}{\|}}{C}-alkyl.$$

The various compounds of the invention may be prepared as outlined below.

Compounds of formula I wherein Z is

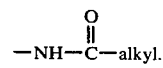

(formula II) may be prepared according to the following reaction description.

The starting compounds of formula I wherein Z is

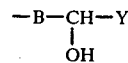

(formula II), and B is —CH=CH— and n is 2, are prepared starting with the hydroxymethyl compound of formula VI

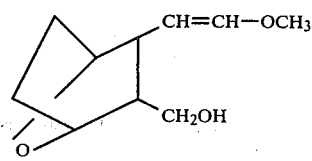

(prepared as described in U.S. Pat. No. 4,143,054). The formula VI compound is acylated by reacting same with an alkanoyl halide such as acetyl chloride in the presence of a basic organic solvent such as pyridine or 2,6-dimethylpyridine to form compound VII

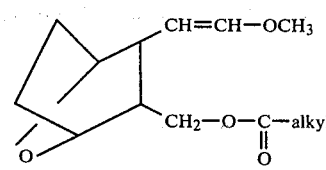

which is then hydrolyzed in the presence of aqueous acid such as trifluoroacetic acid or hydrochloric acid to form aldehyde VIII

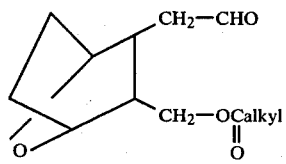  VIII

The aldehyde VIII is then subjected to a Grignard reaction by reacting same with magnesium and a halogenated aromatic derivative such as an o-, m- or p-bromo styrene compound

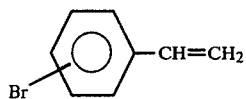

to form the dihydroxy compound IX

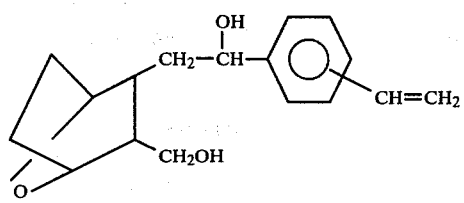  IX

The dihydroxy compound IX is acylated by reaction with an alkanoyl halide such as acetyl chloride in the presence of a basic organic solvent such as pyridine to form ester compound X

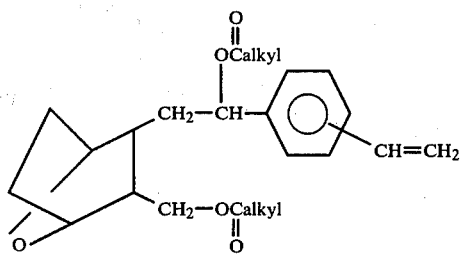  X

Ester X is subjected to oxidative cleavage by reacting same with an oxidizing agent such as sodium iodate in the presence of ruthenium chloride and an appropriate solvent such as carbon tetrachloride, acetonitrile and water to form carboxylic acid XI

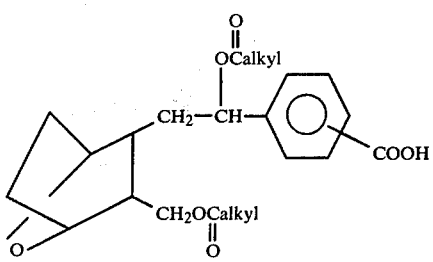  XI

Acid XI is esterified by, for example, reacting same with diazomethane in ether to form the ester XII

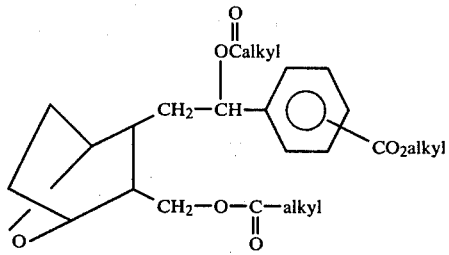  XII which is then reduced by reaction with hydrogen employing a palladium on carbon catalyst in the presence of acetic acid to form ester XIII

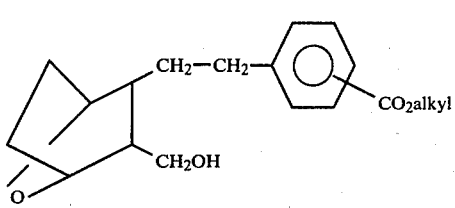  XIII

The remaining alkanoate moiety is removed from ester XIII by subjecting same to acetate hydrolysis, for example, reacting XIII with potassium carbonate in the presence of an alcohol solvent, such as methanol, to form the hydroxymethyl compound XIV

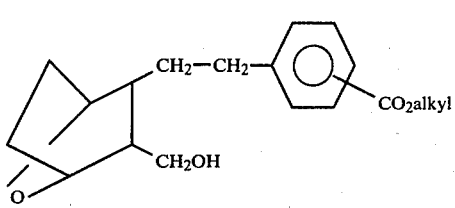  XIV

The compound XIV is then oxidized by reaction, for example with pyridinium chlorochromate in the presence of a chlorinated hydrocarbon solvent to form the corresponding aldehyde XV

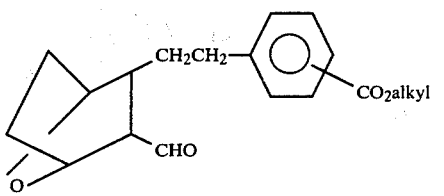  XV

Where aldehyde XV is in the cis endo form it is epimerized by reaction with sodium methoxide in the presence of methanol to form the corresponding trans isomer. However, if compound XV is in the cis exo form, it need not be epimerized but is directly subjected to a Wadsworth-Emmons reaction (as is the trans form of the isomer, if present), by reacting same with a dialkoxy phosphonate, such as of the structure

  A employing a molar ratio of XV:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

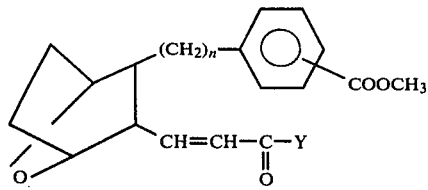

XVI

Compound XVI may then be reduced by reacting same with sodium borohydride as described herein to form ester compound XVII

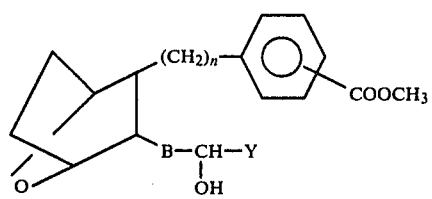

XVII wherein B is —CH=CH— and n is 2. The ester XVII can be converted to the free acid, that is, to

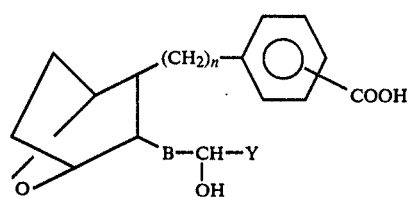

XVIII (B is —CH=CH— and n is 2) by treating the ester with a base, such as lithium hydroxide, followed by neutralization with an acid, such as dilute hydrochloric acid or oxalic acid.

Intermediate aldehydes of the structure

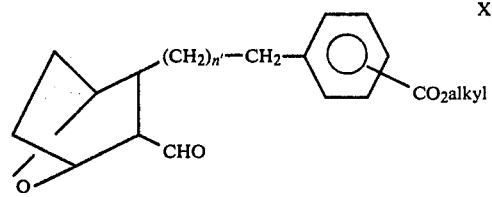

XVA wherein n' is 0 or 1 in the form of its cis exo isomer, that is the [1β,2α,3α,4β] form, may be prepared by reacting a benzofuran-ol or benzopyran-ol of the structure

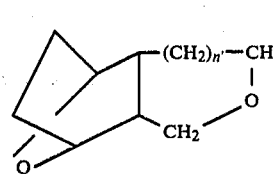

VIA (wherein n' is 0 in the case of the benzofuran and n' is 1 in the case of the benzopyran, each of which is prepared as described in U.S. Pat. No. 4,143,054) with a hydrazine compound of the structure

A' in the presence of a chlorinated hydrocarbon solvent to form the corresponding hydrazone

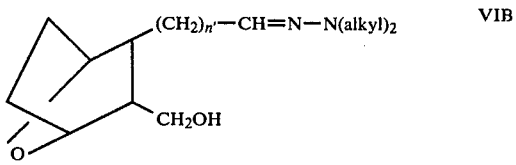

VIB

The formula VIB compound is acylated by reacting same with an alkanoyl halide such as acetyl chloride in the presence of a basic organic solvent such as pyridine or 2,6-dimethylpyridine to form compound VIIA

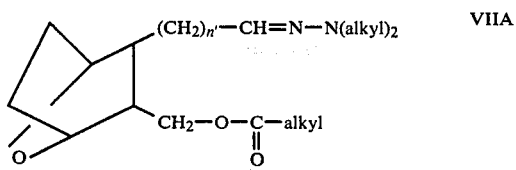

VIIA which is then hydrolyzed in the presence of cupric chloride and an inert solvent such as tetrahydrofuran buffered to pH 7 to form aldehyde VIIIA

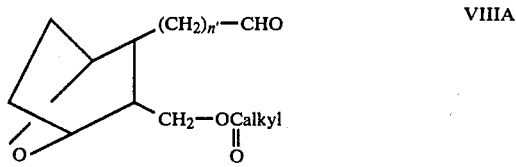

VIIIA

The aldehyde VIIIA may then be subjected to a Grignard reaction in the presence of a bromo styrene compound as described hereinbefore to form the dihydroxy compound

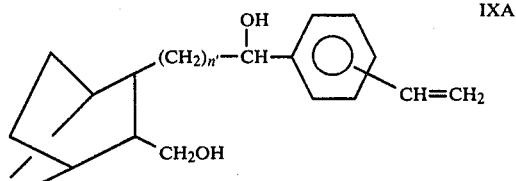

IXA which is then acylated (as described hereinbefore) to form diester XA

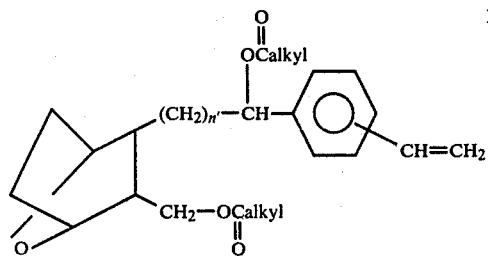

The diester XA is subjected to oxidative cleavage (as described above) to form carboxylic acid XIA

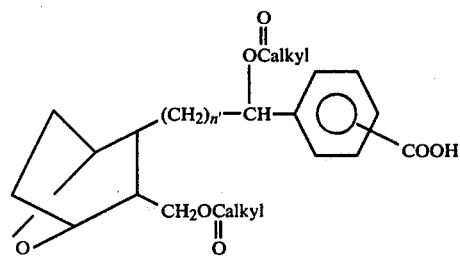

which is esterified to ester XIIA

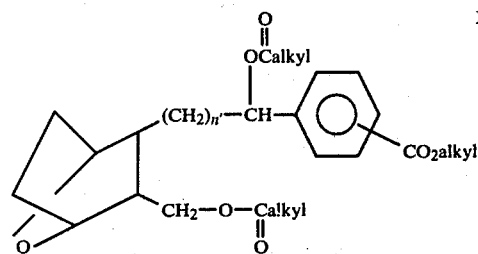

The ester XIIA is reduced to ester XIIIA

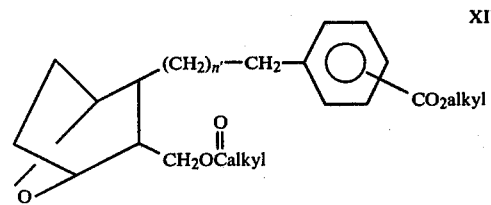

which is then hydrolyzed to hydroxymethyl compound XIVA'

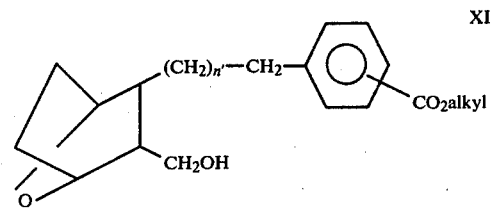

Hydroxymethyl compound XIVA' is then oxidized to the aldehyde intermediate XVA. The aldehyde XVA may then be employed to prepare any of the formula I compounds of the invention as described herein.

Compounds of formula II wherein B is —$CH_2$—$CH_2$— are prepared by reducing compound XVII

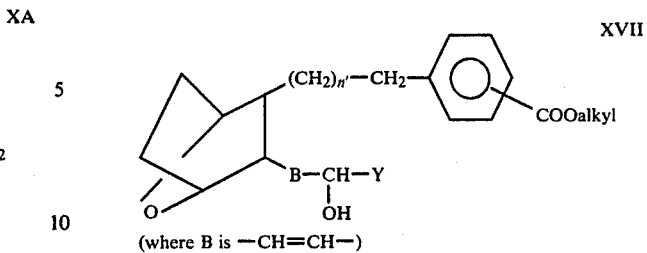

(where B is —CH=CH—) employing conventional reduction procedures to form compound XIX

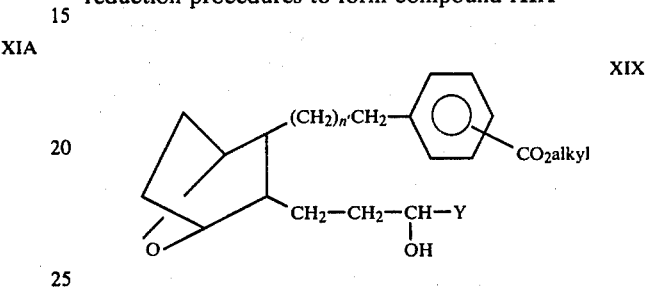

which is then subjected to ester hydrolysis to form

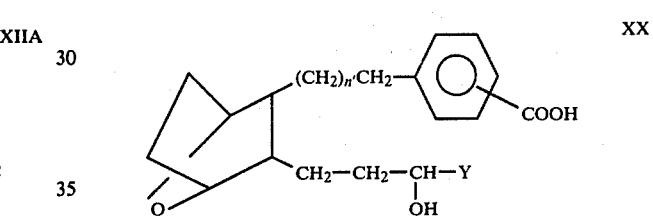

Compounds of formula II wherein B is —C≡C— may be prepared by reacting the aldehyde XVB

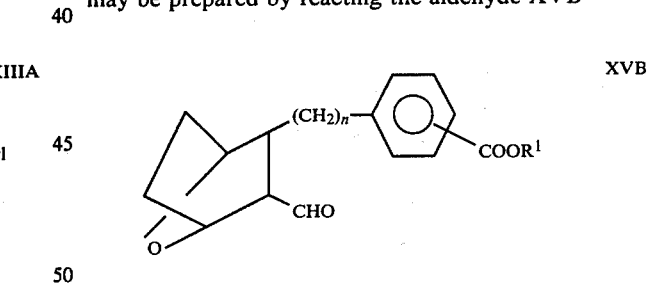

(wherein $R^1$ is lower alkyl) with a phosphonate B

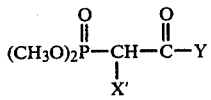

(wherein X' is Cl or Br, prepared as described in U.S. Pat. No. 4,169,145) employing a molar ratio of XVB:B of within the range of from about 1:1 to about 0.2:1 in the presence of potassium t-butoxide in tetrahydrofuran or sodium hydride in dimethylsulfoxide. The resulting phosphonate product, an α-haloenone (which is a mixture of E and Z isomers) is then subjected to a base such as potassium t-butoxide in tetrahydrofuran to form

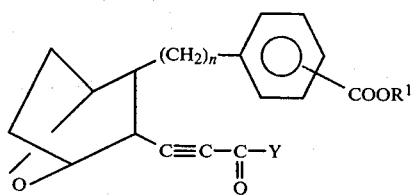

XXI

The ynone XXI is then reduced with NaBH$_4$—CeCl$_3$ to afford II. A similar technique is described in U.S. Pat. No. 4,169,145, Example 23 and is described in Il. Farmaco-Ed. Sc. O Vol. 31-fasc. 10, pp. 763–766 (1975) in the paper entitled "α-Halo-α,β-unsaturated ketones: a synthetic approach to 13-dehydroprostaglandins" by C. Gandolfi and coworkers.

The compounds of formula II of this invention have five centers of asymmetry as indicated by the asterisks in formula II. However, it will be apparent that each of the formulae set out above which do not include asterisks still represent all of the possible stereoisomers thereof. All of the various stereoisomeric forms are within the scope of the invention.

The various stereoisomeric forms of the formula II compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

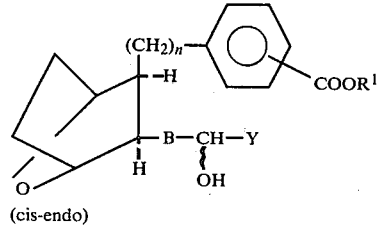

IIa (cis-endo)

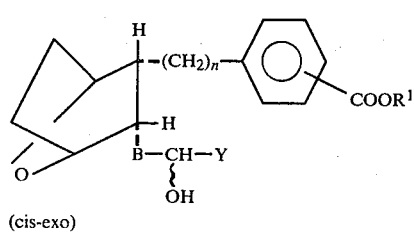

IIb (cis-exo)

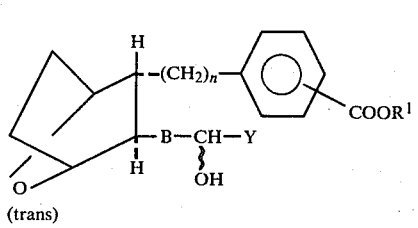

IIc (trans)

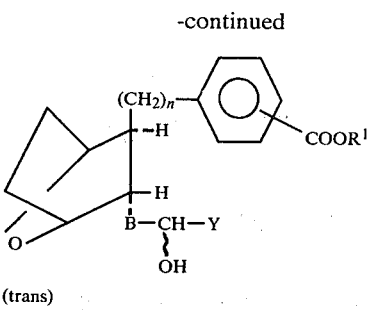

IId (trans)

Compounds of formula I wherein Z is

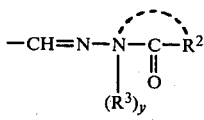

(formula III) may be prepared according to the following reaction sequence.

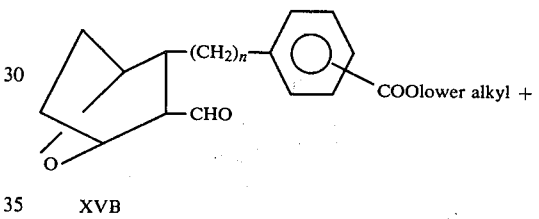

XVB $$H_2N-N-C-R^2 \xrightarrow{EtOH}$$
(R$^2$ is other than aryloxy)

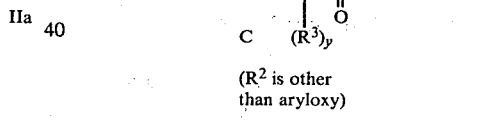

XXII ester hydrolysis →

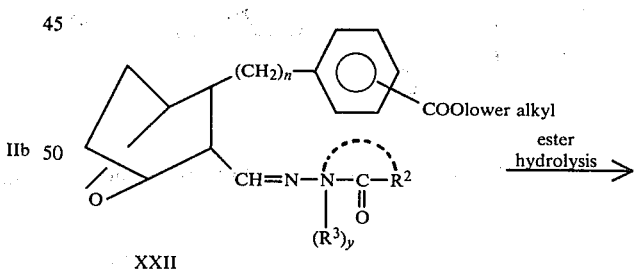

XXII

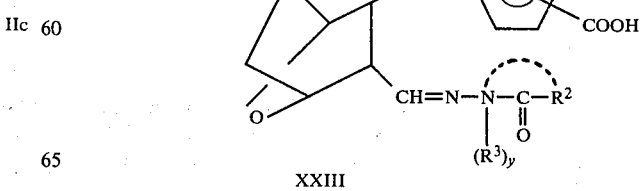

XXIII

Aldehyde XVB of the structure

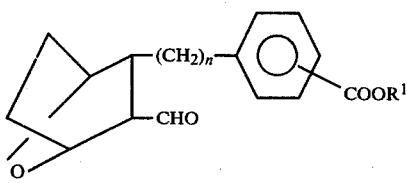

XVB wherein $R^1$ is lower alkyl (prepared as described above) is reacted with a hydrazine derivative, such as of the structure

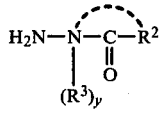

C.

employing a molar ratio of XVB:C of within the range of from about 0.8:1 to about 1:1, in the presence of a solvent, such as methanol or ethanol, to form an ester compound of the structure

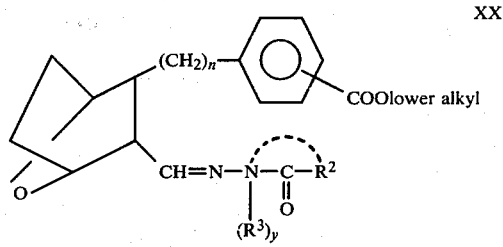

XXII

The ester XXII can be converted to the free acid, that is, to

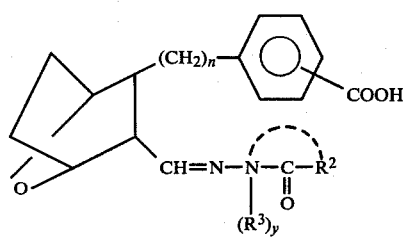

XXIII by treating the ester XXII with a base, such as lithium hydroxide, followed by neutralization with an acid, such as dilute hydrochloric acid or oxalic acid.

Where $R^2$ is aryloxy, the starting aldehyde XVB is replaced by the corresponding acid

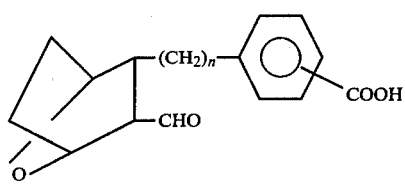

XVB which is prepared as described hereinafter:

The compounds of formula III of this invention have four centers of asymmetry as indicated by the asterisks in formula III. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

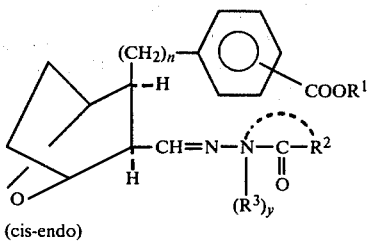

IIIa (cis-endo)

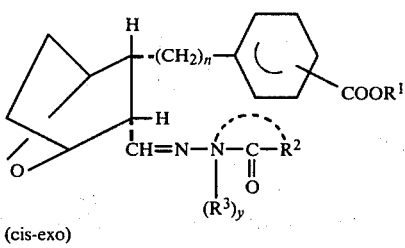

IIIb (cis-exo)

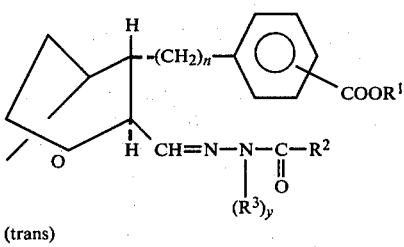

IIIc (trans)

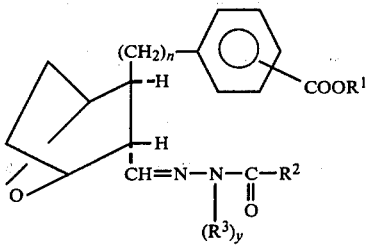

IIId

Compounds of formula I wherein Z is —CH=N—O—$(CH_2)_p$—$R^4$ (formula IV) may be prepared according to the following reaction sequence.

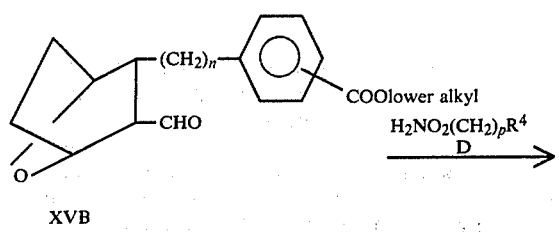

-continued

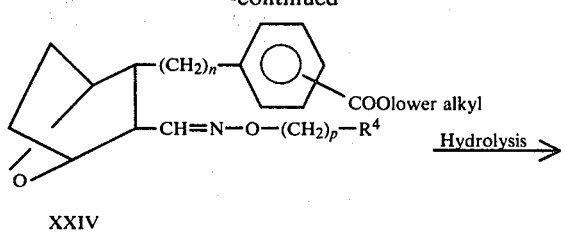

XXIV

Hydrolysis →

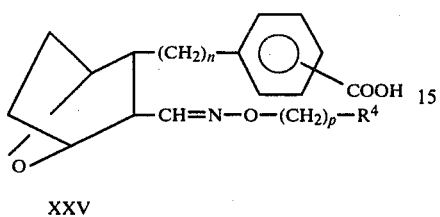

XXV

Aldehyde XVB of the structure

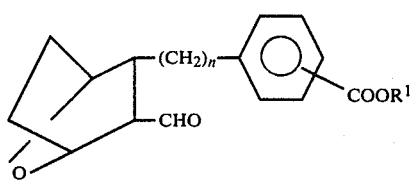

XVB wherein $R^1$ is lower alkyl (prepared as described above) is reacted with an oxyamine, such as of the structure $$H_2NO(CH_2)_pR^4 \qquad D$$

employing a molar ratio of XVB:D of within the range of from about 0.1:1 to about 1:1, under basic conditions, such as in the presence of sodium acetate and an inert organic solvent, such as ethanol, ether, tetrahydrofuran or toluene to form a compound of the structure

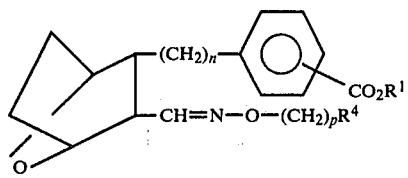

XXIV

The ester XXIV can be converted to the free acid, that is, to

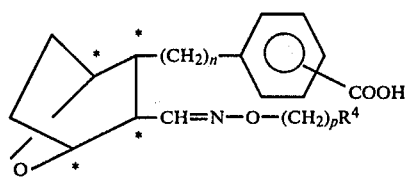

XXV by treating the ester XXIV with a base, such as lithium hydroxide, followed by neutralization with an acid, such as dilute hydrochloric acid or oxalic acid.

The compounds of formula IV have four centers of asymmetry as indicated by the asterisks in formula IV. However, it will be apparent that each of the formulae set out above which do not include asterisks still represent all of the possible stereoisomers thereof. All of the various stereoisomeric forms are within the scope of the invention.

The various stereoisomeric forms of the compounds of formula IV of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

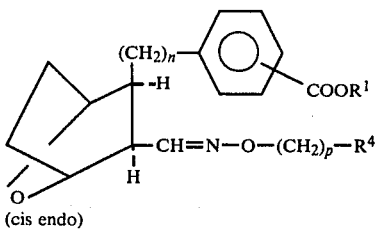
(cis endo)
IVa

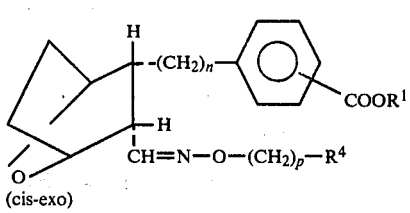
(cis-exo)
IVb

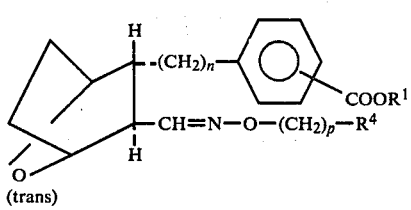
(trans)
IVc

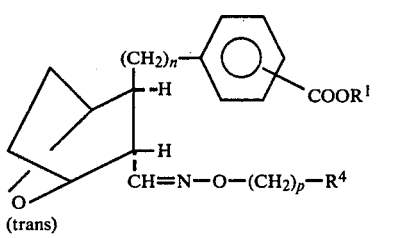
(trans)
IVd

Compounds of formula V (Z is $(CH_2)_m$—NH—$R^5$) may be prepared according to the following reaction sequence.

A. Where m is 1 and $R^5$ is lower alkyl

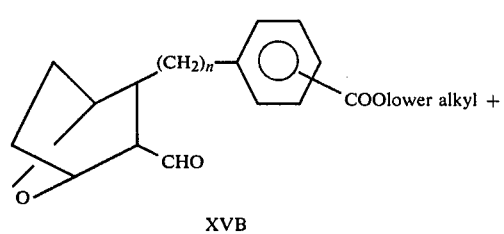

XVB $R^5NH_2 \longrightarrow$

E

-continued

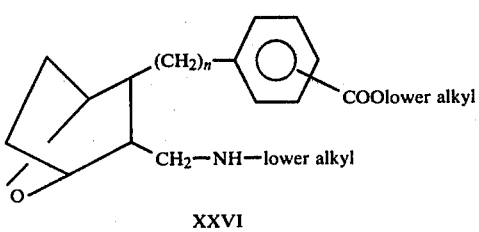

XXVI

B. Where m is 1 and $R^5$ is $-O(CH_2)_qR^7$ where $R^7$ is alkyl or aralkyl and q is 1 to 5, that is, lower alkoxy or aralkoxy

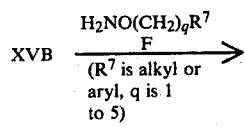

XVB $\xrightarrow[\text{F}]{\text{H}_2\text{NO(CH}_2)_q\text{R}^7}$ ($R^7$ is alkyl or aryl, q is 1 to 5)

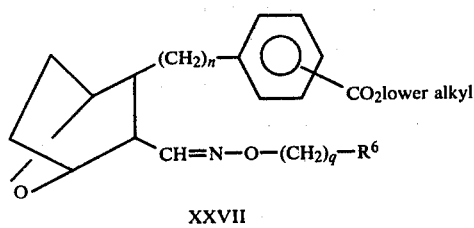

XXVII

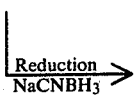 $\xrightarrow[\text{NaCNBH}_3]{\text{Reduction}}$

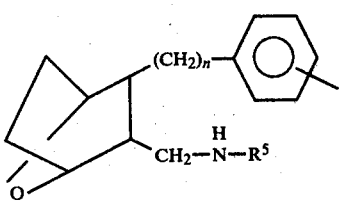

XXVIII $\Bigg\downarrow$ Hydrolysis

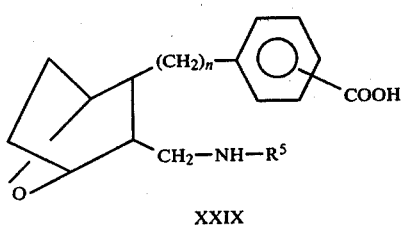

XXIX

C. Where m is 1 and $R^5$ is $-\text{NH}-\overset{\overset{\displaystyle O}{\|}}{\text{C}}-R^6$ ($R^6$ is lower alkyl or phenyl).

XVB $\xrightarrow[\text{G}]{\text{H}_2\text{N}-\text{NH}\overset{\overset{\displaystyle O}{\|}}{\text{C}}-R^6}$ -continued

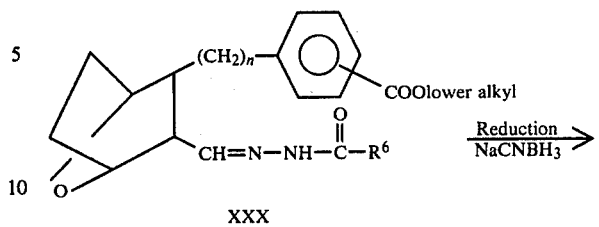

XXX $\xrightarrow[\text{NaCNBH}_3]{\text{Reduction}}$

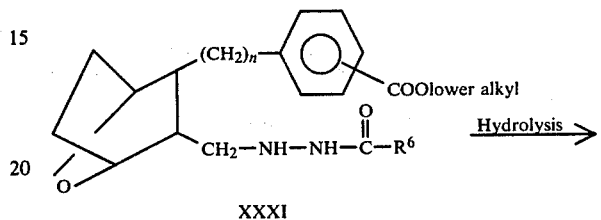

XXXI $\xrightarrow{\text{Hydrolysis}}$

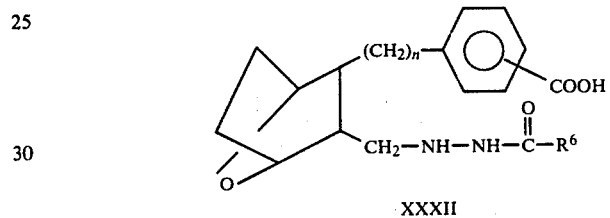

XXXII

D. Where m is 0 and $R^5$ is $-\text{NH}-$alkyl

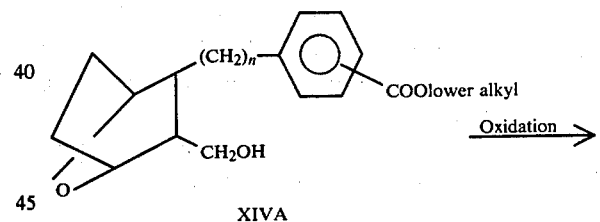

XIVA $\xrightarrow{\text{Oxidation}}$

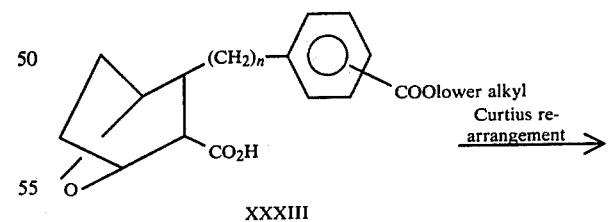

XXXIII $\xrightarrow{\text{Curtius re-arrangement}}$

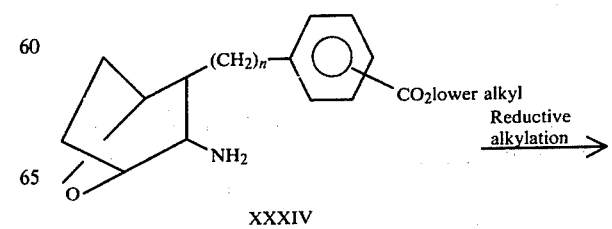

XXXIV $\xrightarrow{\text{Reductive alkylation}}$

-continued

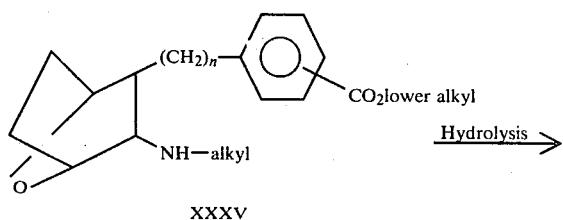

XXXV

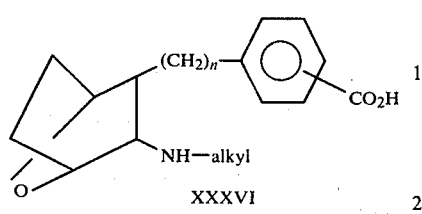

XXXVI

As seen in reaction sequence "A", compounds of the invention where m is 1 and $R^5$ is lower alkyl, that is

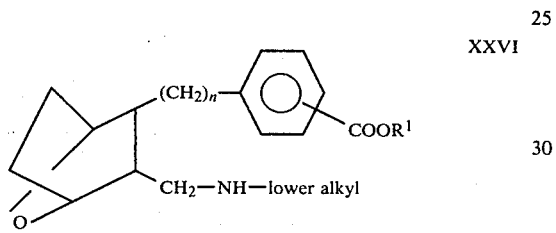

XXVI are prepared by reacting aldehyde XVB with an alkylamine ($R^5NH_2$) E employing a molar ratio of XVB:alkylamine of within the range of from about 0.8:1 to about 1:1, in a solvent such as methanol or ethanol, and a reducing agent such as sodium borohydride or sodium cyanoborohydride.

As seen in reaction sequence "B", compounds of the invention wherein m is 1 and $R^5$ is lower alkoxy or aralkoxy, that is

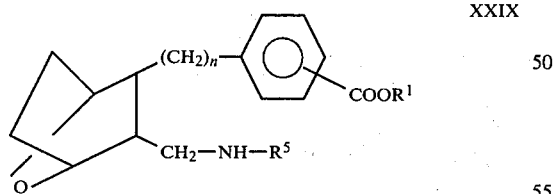

XXIX are prepared by reacting aldehyde XVB with an oxyamine, such as of the structure

   F (p is 1 to 5, $R^7$ is alkyl or aralkyl) employing a molar ratio of XVB:F of within the range of from about 0.8:1 to about 1:1 in a solvent such as methanol or ethanol to form compound XXVII

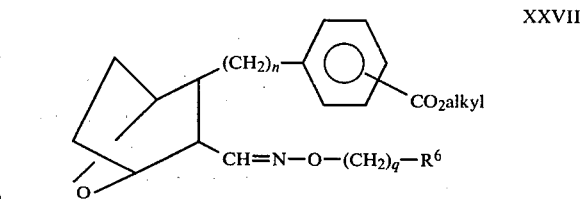

XXVII

Compound XXVII is then reduced, such as by reacting XXVII with a reducing agent such as $NaBH_4$ or $NaCNBH_3$ in a solvent such as methanol or ethanol and in the presence of acetic acid to form the ester compound XXVIII which is hydrolyzed to acid XXIX.

Where q is 0 so that $R^5$ is aryloxy, then compound XIVA is first hydrolyzed by reacting same with lithium hydroxide or sodium hydroxide to form the corresponding carboxylic acid XIVB

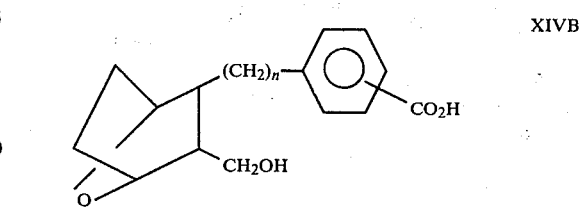

XIVB which is then subjected to a Collins oxidation to form the corresponding aldehyde XVB'

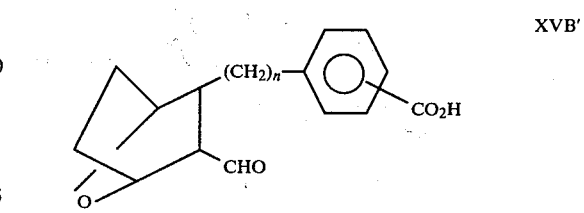

XVB'

Aldehyde XVB' is reacted with an aryloxyamine F

   F (where q is 0 and $R^7$ is aryl) to form the compound XXVIIA

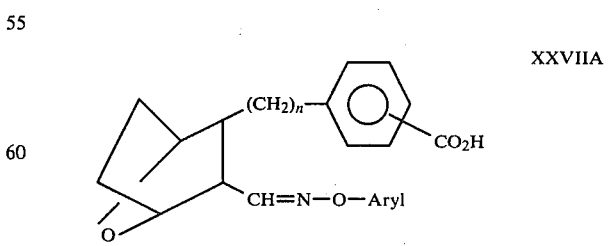

XXVIIA

Compound XXVIIA is then reduced with $NaCNBH_3$ in the presence of acetic acid to form the aryloxyamine of the invention

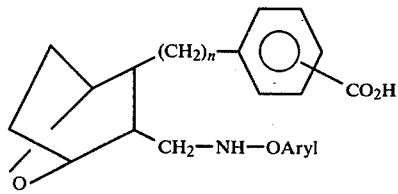

XXVIIIA

In the reaction sequence identified as "C" compounds of the invention wherein m is 1 and

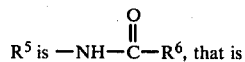

that is

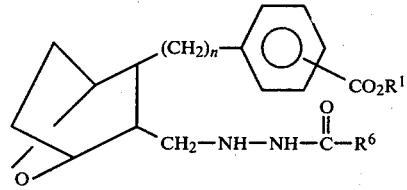

XXXII are prepared by reacting aldehyde XVB with a hydrazine derivative

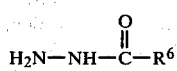

G to form compound XXX, employing a molar ratio of XVA:G of within the range of from about 0.8:1 to about 1:1, in a protic solvent such as methanol or ethanol.

Compound XXX is then reduced, such as by reacting XXX with a reducing agent, such as NaBH$_3$CN or NaBH$_4$ in the presence of acetic acid or hydrogen with palladium on carbon as a catalyst to form compound XXXI.

Any of the aforementioned esters can be converted to the free acid

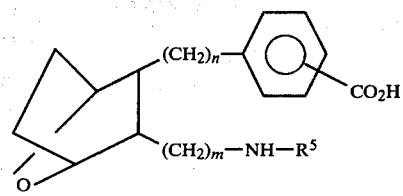

VA by treating the esters with a base, such as lithium hydroxide, followed by neutralization with an acid, such as dilute hydrochloric acid or oxalic acid.

In the reaction sequence identified as "D", compounds of the invention wherein m is 0 and R$^5$ is —NH—alkyl, that is

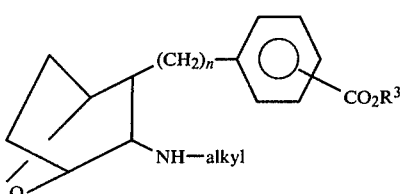

XXXVI are prepared by oxidizing hydroxymethyl compound XIVA, such as by reacting XIVA with an oxidizing agent, such as pyridinium dichromate in a solvent, such as dimethylformamide, to form the acid XXXIII. Acid XXXIII is subjected to a Curtius rearrangement reaction which involves reacting acid XXXIII with carbonyldiimidazole in the presence of an inert organic solvent, such as toluene, under an inert atmosphere, followed by addition of trimethylsilylazide to the reaction mixture and the resulting isocyanate solution is converted to the amine XXXIV by reacting same with hydrochloric acid.

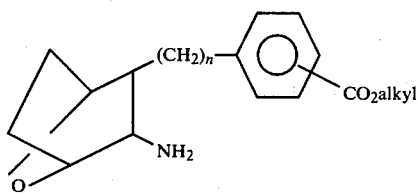

XXXIV

The amine XXXIV is subjected to reductive alkylation by reacting same with heptanal in a solvent, such as methanol and then adding sodium borohydride or other reducing agent, such as sodium cyanoborohydride in the presence of acetic acid to form the ester compound XXXV which may be hydrolyzed to the corresponding acid XXXVI.

The formula V compounds of this invention have four centers of asymmetry as indicated by the asterisks in formula V. However, it will be apparent that each of the formulae set out above which do not include asterisks still represent all of the possible stereoisomers thereof. All of the various stereoisomeric forms are within the scope of the invention.

The various stereoisomeric forms of the formula V compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

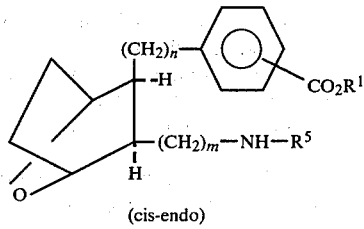

Va (cis-endo)

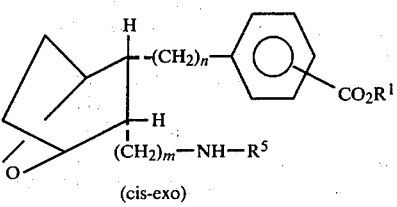

Vb (cis-exo)

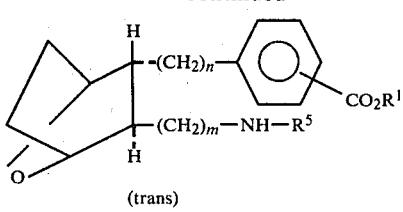

Vc (trans)

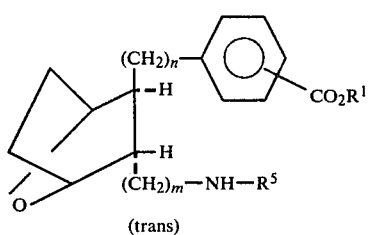

Vd (trans)

The nucleus in each of the compounds of the invention is depicted as

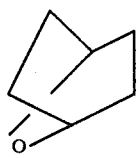

for matter of convenience; it will also be appreciated that the nucleus in the compounds of the invention may be depicted as

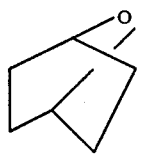

The compounds of this invention are cardiovascular agents useful as platelet aggregation inhibitors, e.g., for treatment of thrombolytic disease, such as coronary or cerebral thromboses. They are also selected thromboxane $A_2$ synthetase inhibitors and/or thromboxane antagonists, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 gm/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of this invention.

EXAMPLE 1

[1β,2β,3α(1E),4β]-4-[2-[3-(3-Cyclohexyl-3-hydroxy-1-propenyl)-7-oxabicyclo[2.2.1]hept-2-yl]ethyl]benzoic acid (fast moving isomer)

A.

(endo)-3-[2-Methoxyethenyl)-7-oxabicyclo[2.2.1]heptane-2-methanol acetate

To 2.5 g of (endo)-3-(2-methoxyethenyl)-7-oxabicyclo[2.2.1]heptane-2-methanol prepared as described in U.S. Pat. No. 4,143,054, Example 7, (13.5 mmole) in 5.5 ml pyridine (67.4 mmole, 5 equiv.) was added at 0° C. 1.6 mg acetyl chloride (20.2 mm, 1.5 equiv.). The mixture was stirred at 0° C. for 50 minutes, then diluted with 300 ml of ethyl ether. The ethereal solution was washed with three 100 ml portions of saturated cupric sulfate solution and two 100 ml portions of water and dried over anhydrous magnesium sulfate, and concentrated to give 2.5 g of title A oil. This oil was used without purification.

B.

(endo)-3-(Acetoxymethyl)-7-oxabicyclo[2.2.1]heptane-2-acetaldehyde

A mixture of 2.5 g of crude compound from Part A and 45 ml of 20% aqueous trifluoroacetic acid was stirred under an argon atmosphere for 30 minutes. To the reaction mixture was added solid sodium bicarbonate in small portions until the solution turned basic. The solution was then saturated with sodium chloride and extracted with five 200 ml portions of dichloromethane. The organic layer was dried over anhydrous magnesium sulfate and concentrated to give 2.2 g of title B aldehyde (77.2%).

C.

4-[1-Hydroxy-2-[(3-hydroxymethyl)-7-oxabicyclo[2.2.1]hept-2-yl)]ethyl]styrene

To 267 mg of magnesium turnings (11 mmole, 2.5 equiv.) in 10 ml of dry tetrahydrofuran (THF) under an argon atmosphere at 25° C. was added dropwise a solution of 2.12 g of bromostyrene (11.6 mmole, 2.6 equiv.) in 10 ml THF. The mixture was stirred for 2 hours. To this Grignard solution was added dropwise at 25° C. a solution of 929 mg of Part B aldehyde (4.4 mmole) in 10 ml THF over a one hour period. The reaction was stirred for 30 minutes, guenched with 2.5 ml of 1N HCl solution and diluted with 500 ml of ether. The ethereal solution was washed with three 100 ml portions of saturated sodium bicarbonate, two 100 ml portions of water, then dried over anhydrous magnesium sulfate and concentrated to give a crude oil.

This crude oil was purified by flash chromatography on a LPS-1 silica gel column, eluting with 25% EtOAc/hexane to give 840 mg of title C dihydroxy compound (70.2%).

D.

4-[1-Hydroxy-2-[(3-hydroxymethyl)-7-oxabicyclo[2.2.1]hept-2-yl]ethyl]styrene, diacetate To 840 mg of dihydroxy compound from Part C in 3 ml of pyridine was added at 0° C. 1 ml of acetyl chloride. The mixture was stirred at 0° C. for 1 hour and diluted with 150 ml of ether. The ethereal solution was washed with three 50 ml portions of saturated cupric sulfate solution and two 50 ml portions of water and dried over anhydrous magnesium sulfate and concentrated to give a crude oil.

This crude oil was purified by flash chromatography on a LPS-1 silica gel column, eluting with 30% EtOAc/hexane to give 552 mg of title D diacetate compound (47.4%).

E.
[1β,2β,3β,4β]-4-[2-[3-Acetoxymethyl-7-oxabicyclo[2.2.1]hept-2-yl]acetoxyethyl]benzoic acid and

F.
[1β,2β,3β,4β]-4-[2-[3-Acetoxymethyl-7-oxabicyclo[2.2.1]hept-2-yl]acetoxyethyl]benzoic acid, methyl ester To 552 mg of the diacetate from Part D (1.54 mmole) in 4 ml carbon tetrachloride, 4 ml acetonitrile and 6 ml of $H_2O$ at 25° C. were added 1.36 g sodium periodate (6.32 mmole, 4.1 equiv.) and 8.53 mg Ruthenium (III) chloride trihydrate (0.03 mmole, 2.2%). The reaction mixture was stirred for 1 hour and diluted with 50 ml dichloromethane ($CH_2Cl_2$). The aqueous layer was extracted with three 50 ml portions of $CH_2Cl_2$. The combined organic layer was dried over anhydrous magnesium sulfate, filtered through a bed of Celite with 100 ml ether, and concentrated to give 463 mg of crude title E acid.

This crude acid was treated with excess diazomethane in ether and quenched with 0.5 ml of glacial acetic acid. The ethereal solution was washed with 10 ml of saturated sodium bicarbonate, dried over anhydrous magnesium sulfate, and concentrated to give a crude oil.

This crude oil was purified by flash chromatography on a LPS-1 silica gel column, eluting with 25% EtOAc/hexane to give 273 mg of the title F ester (45.4%).

G.
[1β,2β,3β,4β,]-4-[2-[3-Acetoxymethyl-7-oxabicyclo[2.2.1]hept-2-yl]ethyl]benzoic acid, methyl ester A mixture of 599 mg ester from Part F and 599 mg of 10% palladium on carbon in 30 ml of glacial acetic acid was shaken in a Parr bottle at 25° C. under 50 psi hydrogen pressure for 4 hours. The mixture was filtered through a bed of Celite and concentrated to give 330 mg of title G ester (66.9%).

H.
[1β,2β,3β,4β]-4-[2-[3-Hydroxymethyl-7-oxabicyclo[2.2.1]hept-2-yl]ethyl]benzoic acid, methyl ester To 330 mg of ester from Part G (1 mmole) in 20 ml of methanol was added 165 mg of potassium carbonate (1.2 mmole, 1.2 equiv.) The mixture was stirred under an argon atmosphere at 25° C. for 1 hour. The reaction was poured into 300 ml of saturated ammonium chloride then extracted with three 100 ml portions of ether. The ethereal extracts were washed with 50 ml of brine, dried over anhydrous magnesium sulfate, and concentrated to give 275 mg of title H alcohol in the form of a white solid (95.8%).

I.
[1β,2β,3β,4β]-4-[2-[3-Formyl-7-oxabicyclo[2.2.1]hept-2-yl]ethyl]benzoic acid (cis endo isomer)

and

J.
[1β,2β,3β,4β]-4-[2-[3-Formyl-7-oxabicyclo]2.2.1]hept-2-yl]ethyl]benzoic acid (trans isomer)

To 275 mg of alcohol from Part H (0.96 mmole) was added at 25° C., 602 mg of pyridinium chlorochromate (PCC) (2.88 mmole, 3 equiv.). The reaction was stirred for 1 hour, diluted with 200 ml of ether, filtered through a bed of Florisil and concentrated to give title I aldehyde in the form of an oil.

Title I oil was dissolved in 10 ml of methanol and to this solution was added 27 mg of sodium methoxide. The reaction was stirred at 25° C. for 2 hours, then poured into 300 ml of saturated ammonium chloride and extracted with three 100 ml portions of ether. The combined ethereal extract was washed with 50 ml of brine, dried over anhydrous magnesium sulfate and concentrated to give 238 mg of title J aldehyde (87.5%).

K.
[1β,2β,3α(1E),4β]-4-[2-[3-(3-Cyclohexyl-3-oxo-1-propenyl)-7-oxabicyclo[2.2.1]hept-2-yl]ethyl]benzoic acid, methyl ester To a slurry of 44 mg of 50% sodium hydride in mineral oil (0.9 mmole, 1.1 equivalent) in 15 ml of anhydrous dimethoxy ethane (DME) was added 231.9 mg of 2-oxo-2-cyclohexylethyldimethylphosphonate (1.0 mmole, 1.2 equiv.) in 5 ml of DME at 0° C. under an argon atmosphere. The mixture was stirred under argon at 25° C. for 1 hour. To this solution at 25° C. was added 238 mg of aldehyde from Part J (0.83 mmole) in 5 ml of DME. After 20 minutes, the reaction was quenched with 0.5 ml of glacial acetic acid, concentrated, and dissolved in 100 ml of ether. The ethereal solution was washed with three 30 ml portions of 5% potassium bicarbonate and dried over anhydrous magnesium sulfate and concentrated to give 313 mg of Part K compound in the form of a yellow solid. This solid was used in the next reaction without purification.

L.
[1β,2β,3α(1E),4β]-4-[2-[3-(3-Cyclohexyl-3-hydroxy-1-propenyl)-7-oxabicyclo[2.2.1]hept-2-yl]ethyl]benzoic acid, methyl ester (fast moving isomer) and

M.
[1β,2β,3α(1E),4β]-4-[2-[3-(3-Cyclohexyl-3-hydroxy-1-propenyl)-7-oxabicyclo[2.2.1]hept-2-yl]ethyl]benzoic acid, methyl ester (slow moving isomer)

To a solution of 313 mg of crude compound from Part K in 10 ml of dry methanol was added at 25° C. under an argon atmosphere 308.2 mg of cerium chloride containing 35% water (0.83 mmole, 1 equiv.). The reaction was stirred for 10 minutes at 25° C., cooled to 0° C. and 31.3 mg of sodium borohydride (0.83 mmole, 4 equiv.) was slowly added. After stirring for 10 minutes at 0° C., the reaction mixture was poured into 150 ml of saturated ammonium chloride. The mixture was extracted with three 50 ml portions of ether. The ethereal extracts were washed with three 30 ml portions of water and 30 ml of brine. The organic layer was dried over anhydrous magnesium sulfate and concentrated.

Separation and purification was done on a preparative TLC plate, eluting with 50% ethyl acetate in hexane to give 75 mg of title L ester and 75 mg of title M ester.

TLC of title L ester:silica gel; EtOAc/hexane (1:1), $R_f \sim 0.41$.

TLC of title M ester: $R_f\sim 0.31$.

N.

[1β,2β,3α(1E),4β]-4-[2-[3-(3-Cyclohexyl-3-hydroxy-1-propenyl)-7-oxabicyclo[2.2.1]hept-2-yl]ethyl]benzoic acid (fast moving isomer)

75 mg of alcohol ester from Part L (0.19 mmole) was dissolved in 10 ml of an 80% tetrahydrofuran-water solution, chilled to 0° C. and 3.8 ml of a 1N potassium hydroxide solution was added. The reaction was stirred at 25° C. for 30 hours. The THF was evaporated under high vacuum and the residue was diluted with 10 ml of water, acidified to pH 3 with a 10% aqueous oxalic acid solution, extracted with three 30 ml portions of ether. The organic layer was washed with three 20 ml portions of water and 20 ml of brine. The product was dried over anhydrous magnesium sulfate and concentrated to give 60 mg of a white solid.

This solid was purified by recrystallization with ethyl acetate and hexane. 18 mg of title product was isolated (24.9%).

Anal. Calcd for $C_{24}H_{32}O_4$ (included 0.35 mole of water): C, 73.76; H, 8.43 Found: C, 73.76; H, 8.30

TLC: Silica gel; ethyl acetate; $R_f\sim 0.45$.

EXAMPLE 1A

[1β,2β,3α(1E),4β]-4-]2-[3-(3-Cyclohexyl-3-hydroxy-1-propenyl)-7-oxabicyclo[2.2.1]hept-2-yl]ethyl]benzoic acid (slow moving isomer)

75 mg of alcohol ester from Example 1, Part M, (0.19 mmole) was dissolved in 10 ml of an 80% tetrahydrofuran-water solution, chilled to 0° C. and 3.8 ml of a 1N potassium hydroxide solution was added. The reaction was stirred at 25° C. for 30 hours. The THF was evaporated under high vacuum and the residue was diluted with 10 ml of water, acidified to pH 3 with a 10% aqueous oxalic acid solution, extracted with three 30 ml portions of ether. The organic layer was washed with three 20 ml portions of water and 20 ml of brine. The product was dried over anhydrous magnesium sulfate and concentrated to give 60 ml of a white solid.

This solid was purified by recrystallization with ethyl acetate and hexane. 15 mg of title product was isolated (24.0%).

Anal. Calcd for $C_{24}H_{32}O_4$ (included 0.21 mole of water) C, 74.24; H, 8.41 Found: C, 74.24; H, 8.35

TLC: Silica gel; ethyl acetate; $R_f\sim 0.40$

EXAMPLE 2

[1β,2α,3α(1E),4β]-4-[2-[3-(3-Cyclohexyl-3-hydroxy-1-propenyl)-7-oxabicyclo[2.2.1]hept-2-yl]ethyl]benzoic acid

A.

(exo)-2-[3-Hydroxymethyl-7-oxabicyclo[2.2.1]hept-2-yl]acetaldehyde, dimethylhydrazone A mixture of 5.0 g (exo)octahydro-5,8-epoxy-1H-benzopyran-3-ol (prepared as described in U.S. Pat. No. 4,143,054) (29.6 mmol) and N,N-dimethylhydrazine (3.5 g, 59.0 mmol, 2 eq) in 25 ml of dry $CH_2Cl_2$ was stirred at 25° C. for 2 hours. The mixture was concentrated to yield the title compound in the form of a crude oil. This crude oil was used without purification.

B.

(exo)-2-[3-Acetoxymethyl-7-oxabicyclo[2.2.1]hept-2-yl]acetaldehyde, dimethyl hydrazone To the title A crude oil in 11.7 g pyridine (148 mmol, 5 eq) at 0° C. was added 3.5 g acetylchloride (44.4 mmol, 1.5 eq). The mixture was stirred at 0° C. for 1 hour, then diluted with 500 ml ether. The ethereal solution was washed with three 150 ml portions of saturated cupric sulfate solution and two 100 ml portions of water, dried over anhydrous magnesium sulfate, concentrated to give 3.5 g of title B compound in the form of a crude oil. This was used without purification.

C.

(exo)-2-[3-Acetoxymethyl-7-oxabicyclo[2.2.1]hept-2-yl]acetaldehyde

To a solution of 3.5 g crude title B compound in 200 ml tetrahydrofuran at 25° C. was added a solution of 4.7 g cupric chloride dihydrate (27.5 mmol, 2 eq) in 220 ml of a pH 7 phosphate buffer. The mixture was stirred at 25° C. for 2.5 hours and then concentrated. The residue was diluted with 600 ml dichloromethane and filtered through a bed of Celite. The filtrate was washed with three 150 ml portions of 5% saturated sodium bicarbonate, then dried over anhydrous magnesium sulfate and concentrated to yield 2.6 g of title C compound in the form of a yellow oil. This was used without purification.

D.

[1β,2α,3α,4β]-4-[1-Hydroxy-2-[(3-hydroxymethyl)-7-oxabicyclo[2.2.1]hept-2-yl]ethyl]styrene and

E.

[1β,2α,3α,4β]-4-[1-Hydroxy-2-[(3-hydroxymethyl)-7-oxabicyclo[2.2.1]hept-2-yl]ethyl]styrene, diacetate To 747 mg Mg turnings (30.8 mmol, 2.5 eq) in 10 ml of dry THF under an argon atmosphere at 25° C. was added dropwise 5.93 g bromostyrene (32.5 mmol, 2.6 eq) in 20 ml of dry THF. The mixture was stirred for 1 hour. To this Grignard reagent was added at 25° C. 2.6 g title C aldehyde (12.3 mmol) in 30 ml of dry THF over a 1 hour period. The reaction mixture was stirred for 30 minutes then quenched with 30 ml of 1N HCl solution and diluted with 1 liter of ether. The ethereal solution was washed with three 100 ml portions of saturated sodium bicarbonate, two 100 ml portions of water, dried over anhydrous magnesium sulfate and then concentrated to yield title D dihydroxy compound as a yellow oil.

A solution of the above title D dihydroxy compound, 130.5 g of triethylamine (1.28 mole, 104 eq), 984 mg 4-dimethyl amino pyridine (8.12 mmole, 0.66 eq) and 66.3 g acetic anhydride (0.64 mole, 52 eq) was stirred at 25° C. for 30 minutes. The mixture was concentrated under vacuum then poured into 100 ml of an ice-water mixture. The aqueous solution was extracted with four 200 ml portions of $CH_2Cl_2$. The combined organic layer was dried over anhydrous magnesium sulfate and concentrated to give a crude oil.

This crude oil was purified on a LPS-1 silica gel column, eluting with 2 liters of 10% EtOAc/hexane and 1 liter of 50% EtOAc/hexane to yield 2.9 g title E diacetate compound as a yellow oil.

F.
[1β,2α,3α,4β]-4-[2-[3-Acetoxymethyl-7-oxabicyclo[2.2.1]hept-2-yl]acetoxyethyl]benzoic acid and

G.
[1β,2α,3α,4β]-4-[2-[3-Acetoxymethyl-7-oxabicyclo[2.2.1]hept-2-yl]acetoxyethyl]benzoic acid, methyl ester To 2.9 g title E diacetate (8.1 mmole) in 20 ml acetonitrile, 20 ml of carbon tetrachloride, 30 ml of water was added at 25° C. 7.14 g sodium periodate (33.2 mmole, 4.1 eq) and 44.8 mg ruthenium (III) chloride trihydrate (0.15 mmole, 2.2%). The mixture was stirred at 25° C. for 2 hours and then diluted with 200 ml $CH_2Cl_2$. The aqueous layer was extracted with three 50 ml portions of $CH_2Cl_2$. The combined organic layer was dried over anhydrous magnesium sulfate and concentrated. The residue was diluted with 300 ml of ether and filtered through a bed of Celite. The filtrate was concentrated to give 2.7 g of title F compound as an oil.

This oil was treated with excess diazomethane in ether to give 2.6 g of a crude oil.

This crude oil was purified on a LPS 1 silica gel column, eluting with 20% EtOAc/hexane to give 1.5 g of pure ester title G compound.

H.
[1β,2α,3α,4β]-4-[2-[3-Acetoxymethyl-7-oxabicyclo[2.2.1]hept-2-yl]ethyl]benzoic acid, methyl ester A mixture of 1.5 g title G compound and 1.5 g of 10% palladium on carbon in 100 ml of glacial acetic acid was shaken in a Parr bottle at 25° C. under 50 psi hydrogen pressure for 6 hours. The mixture was filtered through a bed of Celite and concentrated to give 1.1 g of title H compound as a clear oil.

I.
[1β,2α,3α,4β]-4-[2-[3-Hydroxymethyl-7-oxabicyclo[2.2.1]hept-2-yl]ethyl]benzoic acid, methyl ester To 920 mg of title H compound (2.79 mmole) in 20 ml of methanol was added 460 mg of potassium carbonate (3.34 mmole, 1.2 eq). The mixture was stirred under an argon atmosphere at 25° C. for 1 hour. The reaction mixture was poured into 200 ml of saturated ammonium chloride, then extracted with three 200 ml portions of ether. The ethereal extracts were washed with 100 ml of brine, dried over anhydrous magnesium sulfate, and concentrated to give 750 mg of title I compound as a white solid.

J.
[1β,2α,3α,4β]-4-[2-[3-Formyl-7-oxabicyclo[2.2.1]hept-2-yl]ethyl]benzoic acid, methyl ester A mixture of chromium trioxide (1.56 g, 15.6 mmole, 6 eq) pyridine (2.47 g, 31.3 mmole, 12 eq) in 100 ml of $CH_2Cl_2$ was stirred under an argon atmosphere at 25° C. for 30 minutes. Dry celite (5.0 g) was added, followed by a solution of title I compound (750 mg, 2.61 mmole) in 50 ml $CH_2Cl_2$. The filtrate was washed with three 100 ml portions of 5% sodium bicarbonate, 100 ml of 10% hydrochloric acid, 100 ml of saturated sodium bicarbonate, dried over anhydrous magnesium sulfate, then filtered through a bed of Florisil and concentrated.

The residue was purified by flash chromatography on a LPS-1 silica gel column, eluting with 20% EtOAc/-hexane to yield 535 mg of title J compound as a white solid.

K.
[1β,2α,3α(1E),4β]-4-[2-[3-(3-Cyclohexyl-3-oxo-1-propenyl)-7-oxabicyclo[2.2.1]-hept-2-yl]ethyl]benzoic acid, methyl ester To a slurry of 99 mg of 50% sodium hydride in mineral oil (200 mmole, 1.1 eq) in 30 ml of anhydrous dimethoxy ethane (DME) was added 702.8 mg of 2-oxo-2-cyclohexylethyldimethylphosphonate (3.0 mmole, 1.6 eq) in 10 ml of DME at 0° C. under an argon atmosphere. The mixture was stirred under argon at 25° C. for 1 hour. To this solution at 25° C. was added 535 mg of title J compound (1.88 mmole) in 10 ml of DME. After 60 minutes, the reaction was quenched with 2 ml of glacial acetic acid, concentrated and dissolved in 200 ml of ether. The ethereal solution was washed with three 50 ml portions of 5% potassium bicarbonate and dried over anhydrous magnesium sulfate and concentrated to give 980 mg of a crude oil. This oil was purified by flash chromatography on a LPS-1 silica gel column eluting with 10% EtOAc in hexanes to yield 587 mg of title K compound as a white solid.

L.
[1β,2α,3α(1E),4β]-4-[2-[3-(3-Cyclohexyl-3-hydroxy-1-propenyl)-7-oxabicyclo[2.2.1]hept-2-yl]ethyl]benzoic acid, methyl ester (fast moving isomer) and

M.
[1β,2α,3α(1E),4β]-4-[2-[3-(3-Cyclohexyl-3-hydroxy-1-propenyl)-7-oxabicyclo[2.2.1]hept-2-yl]ethyl]benzoic acid, methyl ester (slow moving isomer)

To a solution of 587 mg of title K compound in 15 ml of dry methanol was added at 25° C. under an argon atmosphere 578 mg of cerium chloride containing 25.7% water (1.49 mmole, 1 eq). The reaction was stirred for 10 minutes at 25° C., cooled to 0° C. and 56.6 mg of sodium borohydride (1.49 mmole, 4 eq) was slowly added. After stirring for 10 minutes at 0° C., the reaction mixture was poured into 100 ml of saturated ammonium chloride. The mixture was extracted with three 150 ml portions of ether. The ethereal extracts were washed with three 50 ml portions of water and 50 ml of brine. The organic layer was dried over anhydrous magnesium sulfate and concentrated.

Separation and purification was done on LPS-1 silica gel column, eluting with 25% ethyl acetate in hexane to give 365 mg of title L compound and 125 mg of title M compound.

TLC of L: silica gel, EtOAc/hexane (1:1); $R_f \sim 0.62$
TLC of M: $R_f \sim 0.46$

N.
[1β,2α,3α(1E),4β]-4-[2-[3-(3-Cyclohexyl-3-hydroxy-1-propenyl)-7-oxabicyclo[2.2.1]hept-2-yl]ethyl]benzoic acid 365 Mg of title L alcohol ester (0.92 mmole) was dissolved in 30 ml of an 80% tetrahydrofuran-water solution, and 19 ml of a 1N potassium hydroxide solution was added dropwise. The reaction was stirred at 25° C., then warmed up to 50° C. over a 48 hour period. The THF was evaporated under high vacuum and the residue was diluted with 20 ml of water, acidified to pH 3 with a 10% aqueous oxalic acid solution and extracted with three 60 ml portions of ether. The organic layer was washed with three 30 ml portions of water and 30 ml of brine. The product was dried over anhydrous magnesium sulfate and concentrated to give a white solid.

This was filtered through a polycarbonate membrane. The solvents were evaporated under high vacuum for 2 days to give 325 mg of title product (94.2%).

Analysis calcd for C, 74.96; H, 8.39 Found: C, 74.74; H, 8.39

TLC: silica gel; ethyl acetate/hexane (7:3); $R_f \sim 0.46$

EXAMPLE 3

[1β,2β,3α(1E,3S*),4β]-4-[2-[3-(3-Hydroxy-4,4-dimethyl-1-octenyl)-7-oxabicyclo[2.2.1]hept-2-yl]ethyl]benzoic acid

A.
[1β,2β,3α(1E),4β]-4-[2-[3-(3-Oxo-4,4-dimethyl-1-octenyl)-7-oxabicyclo[2.2.1]hept-2-yl]ethyl]benzoic acid, methyl ester To a slurry of 41.8 mg of 50% sodium hydride in mineral oil (0.87 mmole, 1.1 equivalent) in 60 ml of anhydrous dimethoxyethane (DME) is added 237 mg of 2-oxo-3,3-dimethyl heptyl dimethyl phosphonate (0.95 mmole, 1.2 equiv.) in 10 ml of DME at 0° C. under an argon atmosphere. The mixture is stirred under argon at 25° C. for 1 hour. To this solution at 25° C. is added [1β,2β,3α,4β)]-4-[2-[3-formyl-7-oxabicyclo[2.2.1]hept-2-yl]ethyl]benzoic acid, methyl ester prepared as described in Example 1 (0.79 mmole) in 5 ml of DME. After 45 minutes, the reaction is quenched with 0.5 ml of glacial acetic acid, concentrated, and dissolved in 150 ml of ether. The ethereal solution is washed with three 40 ml portions of 5% potassium bicarbonate and dried over anhydrous magnesium sulfate and concentrated. The residue is purified by flash chromatography on LP-1 silica gel, eluting with 3:7 ether/hexane to provide 290 mg (93.7%) yield of the title A compound.

B.
[1β,2β,3α(1E,3S*),4β]-4-[2-[3-(3-Hydroxy-4,4-dimethyl-1-octenyl)-7-oxabicyclo[2.2.1]hept-2-yl]ethyl]benzoic acid, methyl ester and

C.
[1β,2β,3α(1E,3R*),4β]-4-[2-[3-(3-Hydroxy-4,4-dimethyl-1-octenyl)-7-oxabicyclo[2.2.1]hept-2-yl]ethyl]benzoic acid, methyl ester To a solution of the title A compound (3.2 mmole) in 30 ml of dry methanol is added at 25° C. under an argon atmosphere 1.19 g of cerium chloride heptahydrate (3.2 mmole, 1 equivalent). The reaction is stirred for 10 minutes at 25° C., cooled to 0° C. and 123.4 mg of sodium borohydride (3.2 mmole) is slowly added. After stirring for 10 minutes at 0° C., the reaction is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

The residue is purified by flash chromatography on LP-1 silica gel column, eluting with 1:4 EtOAc/hexane to give the title B compound and the title C compound.

D.
[1β,2β,3α(1E,3S*),4β]-4-[2-[3-(3-Hydroxy-4,4-dimethyl-1-octenyl)-7-oxabicyclo[2.2.1]hept-2-yl]ethyl]benzoic acid The alcohol ester (title B compound) (1.61 mmole) is dissolved in 90 ml of an 80% tetrahydrofuran-water solution, chilled to 0° C. and 16.1 ml of a 1N lithium hydroxide solution is added dropwise. The reaction mixture is stirred at 0° C., then slowly warmed up to 25° C. and stirred for 15 hours. The THF is evaporated under high vacuum and the residue is diluted with 30 ml of water, acidified to pH 3 with a 10% aqueous oxalic acid solution, and extracted with three 100 ml portions of ether. The organic layer is washed with three 100 ml portions of water and 100 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 4 days to give [1β,2β,3α(1E,3S*),4β]-4-[2-[3-(3-hydroxy-4,4-dimethyl-1-octenyl)-7-oxabicyclo[2.2.1]hept-2-yl]ethyl]benzoic acid.

EXAMPLE 4

[1β,2β,3α(1E,3R*),4β]-4-[2-[3-(3-Hydroxy-4,4-dimethyl-1-octenyl)-7-oxabicyclo[2.2.1]hept-2-yl]ethyl]benzoic acid To 0.73 mmole of the Example 3 title C alcohol ester in 40 ml of an 80% tetrahydrofuran-water solution at 0° C. is slowly added 7.4 ml of a 1M lithium hydroxide solution. The reaction is stirred at 0° C. and allowed to warm to 25° C. while stirring for 15 hours. The THF is evaporated and the residue is diluted with 20 ml of water, acidified to pH 3 with a 10% aqueous oxalic acid solution, and extracted with three 100 ml portions of ether and 100 ml of brine. The product is dried over anhydrous magnesium sulfate and concentrated to give an oil.

This oil is purified on a CC-7 silica gel column, eluting with a gradient of distilled pentane/ether, filtered through a polycarbonate membrane, and the solvents are evaporated under high vacuum for 4 days to give the title compound as an oil.

EXAMPLE 5

[1β,2β,3α(1E,3S*),4β]-4-[2-[3-(4-Cyclopentyl-3-hydroxy-1-butenyl)-7-oxabicyclo[2.2.1]hept-2-yl]ethyl]benzoic acid

A.
[1β,2β,3α(1E),4β]-4-[2-[3-(3-Oxo-4-cyclopentyl-1-butenyl)-7-oxabicyclo[2.2.1]hept-2-yl]ethyl]benzoic acid, methyl ester To a slurry of 240 mg of 50% sodium hydride in mineral oil (4.76 mmole, 1.1 equivalent) in 60 ml of dimethoxyethane (DME) is added 1.26 g of 2-oxo-3-cyclopentyl propyl dimethylphosphonate (5.41 mmole, 1.2 equivalents) in 10 ml of DME at 0° C. under an argon atmosphere. The mixture is stirred under argon at 25° C. for 1 hour. To this solution at 25° C. is added [1β,2β,3α,4β)]-4-[2-[3-formyl-7-oxabicyclo[2.2.1]hept-2-yl]ethyl]benzoic acid, methyl ester prepared as described in Example 1 (4.53 mmole) in 10 ml of DME. After 1 hour, the reaction is quenched with 1 ml of glacial acetic acid, concentrated, dissolved in 300 ml of ether. The ethereal solution is washed with three 100 ml portions of 5% potassium bicarbonate and 100 ml of brine. The organic layer is dried over anhydrous magnesium sulfate and concentrated to give 1.76 g of crude title A compound. This crude oil is used directly in the next reaction without purification.

B.

[1β,2β,3α(1E,3S*),4β]-4-[2-[3-(4-Cyclopentyl-3-hydroxy-1-butenyl)-7-oxabicyclo[2.2.1]hept-2-yl]ethyl]-benzoic acid, methyl ester and

C.

[1β,2β,3α(1E,3R*),4β]-4-[2-[3-(4-Cyclopentyl-3-hydroxy-1-butenyl)-7-oxabicyclo[2.2.1]hept-2-yl]ethyl]-benzoic acid, methyl ester To a solution of 4.5 mmoles of crude title A compound in 30 ml of dry methanol is added at 25° C. under an argon atmosphere 1.73 g cerium chloride containing 35% water (4.53 mmole, 1 equiv.). The reaction is stirred for 10 minutes at 25° C., cooled to 0° C. and 175 mg of sodium borohydride (4.53 mmole, 4 equiv.) is slowly added. After stirring for 10 minutes at 0° C., the reaction is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

The residue is purified and separated on Waters HPLC, eluting with 1:3 EtOAc/hexane to give the title B compound and the title C compound.

D.

[1β,2β,3α(1E,3S*),4β]-4-[2-[3-(4-Cyclopentyl-3-hydroxy-1-butenyl)-7-oxabicyclo[2.2.1]hept-2-yl]ethyl]-benzoic acid Title B alcohol ester (0.42 mmole) is dissolved in 20 ml of an 80% tetrahydrofuran-water solution, chilled to 0° C. and 4.2 ml of a 1N lithium hydroxide solution is added dropwise. The reaction is stirred at 0° C., then slowly warmed up to 25° C. while stirring over an 18 hour period. The THF is evaporated under high vacuum and the residue is diluted with 10 ml of water, acidified to pH 3 with a 10% aqueous oxalic acid solution, and extracted with three 50 ml portions of ether. The organic layer is washed with three 50 ml portions of water and 50 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 10 days to give [1β,2β,3α(1E,3S*),4β]-4-[2-[3-(3-cyclopentyl-3-hydroxy-1-butenyl-7-oxabicyclo[2.2.1]hept-2-yl]ethyl]-benozic acid.

EXAMPLE 6

[1β,2β,3α(1E,3R*),4β]-4-[2-[3-(4-Cyclopentyl-3-hydroxy-1-butenyl)-7-oxabicyclo[2.2.1]hept-2-yl]ethyl]-benzoic acid Title C alcohol ester (prepared as described in Example 5) (0.27 mmole) is dissolved in 10 ml of an 80% tetrahydrofuran-water solution, chilled to 0° C. and 2.7 ml of a 1N lithium hydroxide solution is added dropwise. The reaction mixture is stirred at 0° C. then slowly warmed up to 25° while stirring over an 18 hour period. The THF is evaporated under high vacuum and the residue is diluted with 10 ml of water, acidified to pH 3 with a 10% aqueous oxalic acid solution, and extracted with three 50 ml portions of ether. The organic layer is washed with three 50 ml portions of water and 50 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 10 days to give the title compound.

EXAMPLE 7

[1β,2β,3α(1E,3S*),4β]-4-[2-[3-(3-Hydroxy-4-phenyl-1-butenyl)-7-oxabicyclo[2.2.1]hept-2-yl]ethyl]benzoic acid

A.

[1β,2β,3α(1E),4β]-4-[2-[3-(3-Oxo-4-phenyl-1-butenyl)-7-oxabicyclo[2.2.1]hept-2-yl]ethyl]benzoic acid, methyl ester To 411.6 mg of freshly distilled diisopropylamine in 80 ml of dry toluene at −78° C. is added 2.3 ml of a 1.6M solution of n-butyllithium in hexane (3.71 mmole). The mixture is stirred for 5 minutes, and to this mixture at −78° C. is added 952.5 mg of 2-oxo-3-phenylpropyl-dimethylphosphonate (3.91 mmole, 1.1 equivalent). The mixture is warmed up to 25° C. while stirring. To this mixture at 25° C. is added [1β,2β,3α,4β]-4-[2-[3-formyl-7-oxabicyclo[2.2.1]hept-2-yl]ethyl]benzoic acid, methyl ester (prepared as described in Example 1) (3.55 mmole). After 2.5 hours, the reaction is quenched with 0.5 ml of glacial acetic acid, diluted with 300 ml of ether. The ethereal solution is washed with three 100 ml portions of a 5% sodium bicarbonate solution and 100 ml of brine. The organic layer is dried over anhydrous magnesium sulfate, concentrated to give a crude oil. This oil is used in the next step without purification.

B.

[1β,2β,3α(1E,3S*),4β]-4-[2-[3-(3-Hydroxy-4-phenyl-1-butenyl)-7-oxabicyclo[2.2.1]hept-2-yl]ethyl]benzoic acid, methyl ester and

C.

[1β,2β,3α(1E,3R*),4β]-4-[2-[3-(3-Hydroxy-4-phenyl-1-butenyl)-7-oxabicyclo[2.2.1]hept-2-yl]ethyl]benzoic acid, methyl ester To a solution of 2.6 mmoles of the crude title A compound in 30 ml of dry methanol is added at 25° C. under an argon atmosphere 1.18 g of cerium chloride containing 35% water (2.64 mmole, 1 equiv.). The reaction is stirred for 10 minutes at 25° C., cooled to 0° C. and 119 mg of sodium borohydride (2.64 mmole, 4 equiv.) is slowly added. After stirring for 10 minutes at 0° C., the reaction is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

Separation and purification is done on Waters HPLC, eluting with 30% ethyl acetate in hexane to give the title B compound and the title C compound.

D.
[1β,2β,3α(1E,3S*),4β]-4-[2-[3-(3-Hydroxy-4-phenyl-1-butenyl)-7-oxabicyclo[2.2.1]hept-2-yl]ethyl]benzoic acid Title B alcohol ester (0.78 mmole) is dissolved in 50 ml of an 80% tetrahydrofuran-water solution, chilled to 0° C. and 7.8 ml of a 1N lithium hydroxide solution is added dropwise. The reaction mixture is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 100 ml portions of ether. The organic layer is washed with three 100 ml portions of water and 100 ml of brine. The product is dried over anhydrous magnesium sulfate and concentrated to give an oil.

This oil is purified on a CC-7 column, eluting with a gradient of distilled pentane/ether and filtered through a polycarbonate membrane. The solvents are evaporated under high vacuum for 12 days to give the title compound.

EXAMPLE 8

[1β,2β,3α(1E,3R*),4β]-4-[2-[3-(3-Hydroxy-4-phenyl-1-butenyl)-7-oxabicyclo[2.2.1]hept-2-yl]ethyl]benzoic acid Title C alcohol ester (prepared as described in Example 7) (0.71 mmole) is dissolved in 40 ml of an 80% tetrahydrofuran-water solution, chilled to 0° C. and 7.1 ml of a 1N lithium hydroxide solution is added dropwise. The reaction mixture is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 100 ml portions of ether. The organic layer is washed with three 100 ml portions of water and 100 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 12 days to give the title compound.

EXAMPLE 9

[1β,2β,3α(1E,3S*),4β]-4-[2-[3-(3-Cyclopentyl-3-hydroxy-1-propenyl)-7-oxabicyclo[2.2.1]hept-2-yl]ethyl]benzoic acid

A.
[1β,2β,3α(1E),4β]-4-[2-[3-(3-Oxo-3-cyclopentyl-1-propenyl)-7-oxabicyclo[2.2.1]hept-2-yl]ethyl]benzoic acid To 375.6 mg of freshly distilled diisopropylamine (3.71 mmole, 1.1 equiv.) in 80 ml of dry toluene at −78° C. is added 2.3 ml of a 1.6M solution of n-butyllithium in hexane (3.71 mmole, 1.1 equiv.). The mixture is stirred for 5 minutes, and to this mixture at −78° C. is added 891.7 mg of 2-oxo-2-cyclopentyl ethyl dimethyl phosphonate (4.05 mmole, 1.2 equiv.). The mixture is warmed up to 25° C. while stirring. To this mixture at 25° C. is added [1β,2β,3α,4β]-4-[2-[3-formyl-7-oxabicyclo[2.2.1]hept-2-yl]ethyl]benzoic acid, methyl ester (prepared as described in Example 1) (3.41 mmole). After 2.5 hours, the reaction is quenched with 0.5 ml of glacial acetic acid, diluted with 300 ml of ether. The ethereal solution is washed with three 100 ml portions of a 5% sodium bicarbonate solution and 100 ml of brine. The organic layer is dried over anhydrous magnesium sulfate, concentrated to give 1.26 g of a crude oil. This oil is used in the next step without purification.

B.
[1β,2β,3α(1E,3S*),4β]-4-[2-[3-(3-Hydroxy-3-cyclopentyl-1-propenyl)-7-oxabicyclo[2.2.1]hept-2-yl]ethyl]benzoic acid, methyl ester and

C.
[1β,2β,3α(1E,3R*),4β]-4-[2-[3-(3-Hydroxy-3-cyclopentyl-1-propenyl)-7-oxabicyclo[2.2.1]hept-2-yl]ethyl]benzoic acid, methyl ester To a solution of 3.4 mmoles of crude title A compound in 30 ml of dry methanol is added at 25° C. under an argon atmosphere 1.29 g of cerium chloride containing 35% water (3.41 mmole, 1 equiv.). The reaction is stirred for 10 minutes at 25° C., cooled to 0° C. and 130 mg of sodium borohydride (3.41 mmole, 4 equiv.) is slowly added. After stirring for 10 minutes at 0° C., the reaction is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

Separation and purification is done on Waters HPLC, eluting with 30% ethyl acetate in hexane to give the title B compound and title C compound.

D.
[1β,2β,3α(1E,3S*),4β]-4-[2-[3-(3-Cyclopentyl-3-hydroxy-1-propenyl)-7-oxabicyclo[2.2.1]hept-2-yl]ethyl]benzoic acid Title B alcohol ester (1.18 mmole) is dissolved in 50 ml of an 80% tetrahydrofuran-water solution, chilled to 0° C. and 11.8 ml of a 1N lithium hydroxide solution is added dropwise. The reaction mixture is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 100 ml portions of water and 100 ml of brine. The product is dried over anhydrous magnesium sulfate and concentrated to give an oil.

EXAMPLE 10

[1β,2β,3α(1E,3R*),4β]-4-[2-[3-(3-Cyclopentyl-3-hydroxy-1-propenyl)-7-oxabicyclo[2.2.1]hept-2-yl]ethyl]benzoic acid Title C alcohol ester (prepared as described in Example 9) (0.82 mmole) is dissolved in 40 ml of an 80% tetrahydrofuran-water solution, chilled to 0° C. and 8.2 ml of a 1N lithium hydroxide solution is added dropwise. The reaction mixture is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, extracted with three 100 ml portions of ether. The organic layer is washed with three 100 ml portions of water and 100 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 11 days to give the title compound.

EXAMPLE 11

[1β,2β,3α(1E,3S*),4β]-4-[2-[3-(4-Cyclohexyl-3-hydroxy-1-butenyl)-7-oxabicyclo[2.2.1]hept-2-yl]ethyl]benzoic acid

A.
[1β,2β,3α(1E,3S*),4β]-4-[2-[3-(3-Oxo-4-cyclohexyl-1-butenyl)-7-oxabicyclo[2.2.1]hept-2-yl]ethyl]benzoic acid To 402.7 mg of freshly distilled diisopropylamine (3.98 mmole, 1.05 equiv.) in 30 ml of dry toluene at −78° C. is added 2.49 ml of a 1.6M solution of n-butyllithium in hexane (3.98 mmole, 1.05 equiv.). The mixture is stirred for 5 minutes, and to this mixture at −78° C. is added 1.034 g of 2-oxo-cyclohexylpropyl dimethyl phosphonate (4.17 mmole, 1.1equiv.). The mixture is warmed up to 25° C. while stirring. To this mixture at 25° C. is added [1β,2β,3α,4β]-4-[2-[3-formyl-7-oxabicyclo[2.2.1]hept-2-yl]ethyl]benzoic acid, methyl ester (prepared as described in Example 1) (3.79 mmole). After 4.5 hours, the reaction is quenched with 0.5 ml of glacial acetic acid, and diluted with 300 ml of ether. The ethereal solution is washed with three 100 ml portions of a 5% sodium bicarbonate solution and 100 ml of brine. The organic layer is dried over anhydrous magnesium sulfate, and concentrated to give 1.38 g of a crude oil. This oil is used in the next step without purification.

B.
[1β,2β,3α(1E,3S*),4β]-4-[2-[3-(4-Cyclohexyl-3-hydroxy-1-butenyl)-7-oxabicyclo[2.2.1]hept-2-yl]ethyl]benzoic acid, methyl ester and

C.
[1β,2β,3α(1E,3R*),4β]-4-[2-[3-(4-Cyclohexyl-3-hydroxy-1-butenyl)-7-oxabicyclo[2.2.1]hept-2-yl]ethyl]benzoic acid, methyl ester To a solution of 2.7 mmoles of crude title A compound in 25 ml of dry methanol is added at 25° C. under an argon atmosphere 1.04 g of cerium chloride containing 35% water (2.71 mmole, 1 equiv.). The reaction is stirred for 10 minutes at 25° C., cooled to 0° C. and 105 mg of sodium borohydride (2.71 mmole, 4 equiv.) is slowly added. After stirring for 10 minutes at 0° C., the reaction mixture is poured into 150 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

Separation and purification are done on LP-1 silica gel column eluting with 30% ethyl aceate in hexane to give title B compound and title C compound.

D.
[1β,2β,3α(1E,3S*),4β]-4-[2-[3-(4-Cyclohexyl-3-hydroxy-1-butenyl)-7-oxabicyclo[2.2.1]hept-2-yl]ethyl]benzoic acid Title B compound (0.6 mmole) is dissolved in 25 ml of an 80% tetrahydrofuran-water solution, chilled at 0° C. and 6.0 ml of a 1N lithium hydroxide solution is added dropwise. The reaction is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 50 ml portions of ether. The organic layer is washed with three 50 ml portions of water and 50 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 7 days to give the title compound.

EXAMPLE 12

[1β,2β,3α(1E,3R*),4β]-4-[2-[3-(4-Cyclohexyl-3-hydroxy-1-butenyl)-7-oxabicyclo[2.2.1]hept-2-yl]ethyl]benzoic acid Title C alcohol ester (prepared in Example 11) (0.28 mmole) is dissolved in 15 ml of an 80% tetrahydrofuran-water solution, chilled to 0° C. and 2.8 ml of a 1N lithium hydroxide solution is added dropwise. The reaction is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 30 ml portions of ether. The organic layer is washed with three 30 ml portions of water and 30 ml of brine. The product is dried over-anhydrous magnesium sulfate and concentrated to gie an oil.

This oil is purified on a CC-7 silica gel column, eluting with a gradient of distiled pentane/ether and filtered through a polycarbnate membrane. The solvents are evaporated under high vacuum for 7 days to give the title compound.

EXAMPLE 13

[1β,2β,3α(1E,3S*),4β]-4-[2-[3-[3-Hydroxy-4-(3-thienyl)-1-butenyl]-7-oxabicyclo[2.2.1]hept-2-yl]ethyl]benzoic acid

A.
[1β,2β,3α(1E,3S*),4β]-4-[2-[3-[3-Oxo-4-(3-thienyl)-1-butenyl]-7-oxabicyclo[2.2.1]hept-2-yl]ethyl]benzoic acid To 402.7 mg of freshly distilled diisopropylamine (3.98 mmole, 1.05 equiv.) in 30 ml of dry toluene at −78° C. is added 2.47 ml of a 1.6M solution of n-butyllithium in hexane (3.98 mmole, 1.05 equiv.). The mixture is stirred for 5 minutes, and to this mixture at −78° C. is added 1.034 g of 2-oxo-3-(3-thienyl)propyl dimethyl phosphonate (4.17 mmole, 1.1 equiv.). The mixture is warmed up to 25° C. while stirring. To this mixture at 25° C. is added [1β,2β,3α,4β]-4-[2-[3-formyl-7-oxabicyclo[2.2.1]hept-2-yl]ethyl]benzoic acid, methyl ester (prepared as described in Example 1) (3.79 mmole). After 3 hours, the reaction is quenched with 0.5 ml of glacial acetic acid, diluted with 300 ml of ether. The ethereal solution is washed with three 100 ml portions of a 5% sodium bicarbonate solution and 100 ml of brine. The organic layer is dried over anhydrous magnesium sulfate, and concentrated to give 1.05 g of a crude oil. This oil is used in the next step without purification.

B.
[1β,2β,3α(1E,3S*),4β]-4-[2-[3-[3-Hydroxy-4-(3-thienyl)-1-butenyl]-7-oxabicyclo[2.2.1]hept-2-yl]ethyl]benzoic acid, methyl ester and

C.
[1β,2β,3α(1E,3R*),4β]-4-[2-[3-[3-[3-Hydroxy-4-(3-thienyl)-1-butenyl]-7-oxabicyclo[2.2.1]hept-2-yl]ethyl]benzoic acid, methyl ester To a solution of 3.69 mmoles of crude title A compound in 30 ml of dry methanol is added at 25° C. under an argon atmosphere 1.416 g of cerium chloride containing 35% water (3.69 mmole, 1 equiv.). The reaction is stirred for 10 minutes at 25° C., cooled to 0° C. and 142.7 mg of sodium borohydride (3.69 mmole, 4 equiv.) is slowly added. After stirring for 10 minutes at 0° C., the reaction mixture is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

Separation and purification is done on Water HPLC eluting with 35% ethyl acetate in hexane to give title B compound and title C compound.

D.
[1β,2β,3α(1E,3S*),4β]-4-[2-[3-[3-Hydroxy-4-(3-thienyl)-1-butenyl]-7-oxabicyclo[2.2.1]hept-2-yl]ethyl]benzoic acid Title B alcohol ester (0.52 mmole) is dissolved in 20 ml of an 80% tetrahydrofuran-water solution, chilled to 0° C. and 5.2 ml of a 1N lithium hydroxide solution is added dropwise. The reaction is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 50 ml portions of ether. The organic layer is washed with three 30 ml portions of water and 30 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 7 days to give the title compound.

EXAMPLE 14

[1β,2β,3α(1E,3R*),4β]-4-[2-[3-[3-Hydroxy-4-(3-thienyl)-1-butenyl]-7-oxabicyclo[2.2.1]hept-2-yl]ethyl]benzoic acid Title C alcohol ester (prepared in Example 13) (0.44 mmole) is dissolved in 20 ml of an 80% tetrahydrofuran-water solution, chilled to 0° C. and 4.4 ml of a 1N lithium hydroxide solution is added dropwise. The reaction is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution, and extracted with three 50 ml portions of ether. The organic layer is washed with three 30 ml portions of water and 30 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 7 days to give the title compound.

EXAMPLE 15

[1β,2α,3α(1E,3S*),4β]-4-[2-[3-(3-Hydroxy-4-phenoxy-1-butenyl)-7-oxabicyclo[2.2.1]hept-2-yl]ethyl]benzoic acid

A.
[1β,2α,3α(1E),4β]-4-[2-[3-(3-Oxo-4-phenoxy-1-butenyl)-7-oxabicyclo[2.2.1]hept-2-yl]ethyl]benzoic acid Sodium hydride (264 mg of 50% in mineral oil, 5.5 mmol) is suspended in dry dimethoxyethane (DME) (50 ml) in an argon atmosphere. A solution of 2-oxo-3-phenoxypropyldimethyl phosphonate (1.9 g, 7.5 mmol) in 10 DME is added. After 45 minutes dist hexamethyl phosphonic triamide (HMPA) (5 ml) is added and the mixture is stirred an additional 45 minutes at room temperature. A solution of aldehyde [1β,2α,3α,4β]-4-[2-[3-formyl-7-oxabicyclo[2.2.1]hept-2-yl]ethyl]benzoic acid, methyl ester (5 mmol) (prepared as described in Example 2) in DME (4 ml) is then added and the mixture is left stirring overnight at room temperature. The reaction is quenched by adding 0.6 ml glacial acetic acid and the solvent is removed in vacuo. The residue is dissolved in ether and washed three times with 1N HCl and twice with saturated NaHCO3 solution. The ether solution is dried over MgSO4 and freed of solvent in vacuo to give 2.25 g oil. This is chromatographed on 110 g silica gel 60 eluting with ether-pet ether (2:3) to give the desired title A compound.

B.
[1β,2α,3α(1E,3S*),4β]-4-[2-[3-(3-Hydroxy-4-phenoxy-1-butenyl)-7-oxabicyclo[2.2.1]hept-2-yl]ethyl]benzoic acid, methyl ester and

C.
[1β,2α,3α(1E,3R*),4β]-4-[2-[3-(3-Hydroxy-4-phenoxy-1-butenyl)-7-oxabicyclo[2.2.1]hept-2-yl]ethyl]benzoic acid, methyl ester The title A compound (2.27 mmol) and cerium chloride hydrate (35.7%, 0.872 g, 2.27 mmol) are dissolved in 22 ml methanol and 2 ml THF in an argon atmosphere. The solution is cooled in an ice bath and sodium borohydride (86 mg, 2.27 mmol) is added portionwise in 30 seconds. The ice bath is removed and the mixture is stirred 8 minutes and then poured into 200 ml saturated NH4Cl solution. The product is extracted into ethyl acetate (5×50 ml), dried and freed of solvent in vacuo leaving 0.9 g of viscous oil. This is chromatographed on 50 g silica gel 60 eluting with ether-pet ether 3:2 to give the title B isomer and the title C isomer.

D.
[1β,2α,3α(1E,3S*),4β]-4-[2-[3-(3-Hydroxy-4-phenoxy-1-butenyl)-7-oxabicyclo[2.2.1]hept-2-yl]ethyl]benzoic acid The title B methyl ester described above (1.1 mmol) is dissolved in 55 ml THF and 10.5 ml H2O in a nitrogen atmosphere. The solution is cooled in an ice bath and 11.0 ml 1N LiOH added. The ice bath is removed and the mixture is stirred at room temperature for 6 hours. Saturated oxalic acid solution is then added to adjust the pH to 3 and the mixture is poured into 400 ml water. The product is extracted into ether (3×200 ml). The combined ether extracts are washed three times with water and once with saturated NaCl solution, dried and freed of solvent in vacuo leaving 407 mg (95%) of the title D compound in the form of a viscous oil.

EXAMPLE 16

[1β,2α,3α(1E,3R*),4β]-4-[2-[3-(3-Hydroxy-4-phenoxy-1-butenyl)-7-oxabicyclo[2.2.1]hept-2-yl]ethyl]benzoic acid The Example 16C methyl ester ([1β,2α,3α(-1E,3R*),4β]-4-[2-[3-(3-hydroxy-4-phenoxy-1-butenyl)-7-oxabicyclo[2.2.1]hept-2-yl]ethyl]benzoic acid, methyl ester) (0.3 mmol) is dissolved in 15 ml THF and 2.9 ml water in an argon atmosphere. The solution is cooled in an ice bath and 3.0 ml 1N LiOH is added. The ice bath is removed and the mixture is stirred at room temperature 6½ hours. The pH is then adjusted to 3 with a saturated solution of oxalic acid and the mixture is poured into 125 ml water. The product is extracted into ether (3×50 ml). The combined ether extracts are washed three times with water and once with saturated NaCl solution, dried over MgSO4, and freed of solvent in vacuo to give the title compound in the form of a viscous oil.

EXAMPLE 17

[1β,2β,3α(3S*),4β]-4-[2-[3-(3-Hydroxyl-1-octynyl)-7-oxabicyclo[2.2.1]hept-2-yl]ethyl]benzoic acid

A.

[1β,2β,3α(1EZ),4β]-4-[2-[3-(2-bromo-3-oxo-1-octenyl)-7-oxabicyclo[2.2.1]hept-2-yl]ethyl]benzoic acid, methyl ester To a slurry of 50% sodium hydride in mineral oil (144 mg, 3 mmol) in 40 ml of anhydrous dimethoxyethane (DME) is added a solution of 1-bromo-2-oxoheptyl-dimethylphosphonate (963.2 mg, 3.2 mmol) in 5 ml of DME. The mixture is stirred at 25° for 90 minutes. A solution of [1β,2β,3α,4β]-4-[2-[3-formyl-7-oxabicyclo[2.2.1]hept-2-yl]ethyl]benzoic acid, methyl ester (prepared as described in Example 1) (2.6 mmol) in 5 ml of DME is added and the mixture is stirred at 25° for 3 hours. The reaction is quenched with 0.2 ml glacial acetic acid and the solvent is removed in vacuo. The residue is diluted with ether and washed with a saturated NaHCO3 solution. The ether layer is dried over MgSO4, filtered and taken to dryness in vacuo to provide 1.2 g of an oil. This is chromatographed on silica gel eluting with ethyl acetate and hexane to give the title A compound as a mixture of E and Z isomers.

B.

[1β,2β,3α(3S*R*,1EZ),4β]-4-[2-[3-(2-Bromo-3-hydroxy-1-octenyl)-7-oxabicyclo[2.2.1]hept-2-yl]ethyl]benzoic acid, methyl ester To 2.1 mmol of the title A ketone and 979.5 mg (2.5 mmol) of cerium chloride heptahydrate in 20 ml of methanol at 0° is added 94 mg (2.5 mmol) of sodium borohydride. The reaction is stirred for 10 minutes, poured into 200 ml of a saturated NH4Cl solution and dried over anhydrous MgSO4 to afford the title B compound as an oil.

C.

[1β,2β,3α(3S*),4β]-4-[2-[3-(3-Hydroxy-1-octynyl)-7-oxabicyclo[2.2.1]hept-2-yl]ethyl]benzoic acid, methyl ester and

D.

[1β,2β,3α(3R*),4β]-4-[2-[3-(3-Hydroxy-1-octynyl)-7-oxabicyclo[2.2.1]hept-2-yl]ethyl]benzoic acid, methyl ester To 2.1 mmol of the title B compound in 10 ml of anhydrous tetrahydrofuran is added 480 mg (4.3 mmol) of potassium t-butoxide. The reaction is stirred for 15 minutes, acidified with 0.1N HCl and extracted with ethyl acetate, washed with saturated NaHCO3, and dried over anhydrous magnesium sulfate to afford an oil. This material is purified by silica chromatography using 1:1 ether-hexane to provide the title C isomer and the title D isomer.

E.

[1β,2β,3α(3S*),4β]-4-[2-[3-(3-Hydroxy-1-octynyl)-7-oxabicyclo[2.2.1]hept-2-yl]ethyl]benzoic acid To 0.79 mmol of the title C ester is dissolved in 40 ml of THF and 10 ml of water, cooled to 0° and 6.9 ml of a 1N LiOH solution is added. The reaction is stirred for 6 hours at 25°, acidified to pH 3 with 10% oxalic acid, diluted with 300 ml of water and extracted with three 200 ml portions of ether. The ethereal layer is washed with water and brine and dried over anhydrous MgSO4 to afford the title compound.

EXAMPLE 18

[1β,2β,3α(1E,3S*),4β]-4-[2-[3-[3-(3-Pyridyl)-3-hydroxy-1-propenyl]-7-oxabicyclo[2.2.1]hept-2-yl]ethyl]benzoic acid By substituting 2-oxo-2-(3-pyridyl)ethyldimethylphosphonate for 2-oxo-2-cyclohexylethyldimethylphosphonate in Example 3, the title compound is obtained.

EXAMPLE 19

[1β,2β,3α(1E,3S*),4β]-4-[2-[3-[4-(3-Pyridyl)-3-hydroxy-1-butenyl]-7-oxabicyclo[2.2.1]hept-2-yl]ethyl]benzoic acid By substituting 2-oxo-3-(3-pyridyl)propyldimethylphosphonate for 2-oxo-2-cyclohexylethyldimethylphosphonate in Example 3, the title compound is obtained.

EXAMPLES 20 AND 21

[1β,2α,3α(1E,3α,4α),4β]-4-[2-[3-(3-Hydroxy-4-phenyl-1-pentenyl)-7-oxabicyclo[2.2.1]hept-2-yl]ethyl]benzoic acid (fast moving isomer A) and

[1β,2α,3α(1E,3α,4β),4β]-4-[2-[3-(3-Hydroxy-4-phenyl-1-pentenyl)-7-oxabicyclo[2.2.1]hept-2-yl]ethyl]benzoic acid (fast moving isomer B)

A. Methyl 2-phenylpropionate

2-Phenylpropionic acid (8.4 g, 56 mmol) in methanol (180 ml) and concentrated H2SO4 (2 ml) were heated at reflux for 4 hours. The reaction was cooled down to room temperature and concentrated in vacuo (~30 ml), which was poured into ice water (~100 ml). The products were extracted with Et2O (150 ml×3), which was washed with saturated NaHCO3, H2O and dried over MgSO4. Filtration and evaporation of solvent yielded a yellow oil (8.9 g), which was distilled to give a colorless oil (8.34 g, 51 mmol, 91%, b.p. 73° C./1.5 mm Hg).

B. 2-Oxo-3-phenylbutyl dimethyl phosphonate n-BuLi (1.6M, 62.5 ml, 100 mmol) was added dropwise to a magnetically stirred solution of dimethyl methyl phosphonate (12.4 g, 100 mmol) in THF (90 ml) at −78° C. Stirring was continued for 30 minutes at −78° C. Then Part A ester (8.2 g, 50 mmol) was added dropwise to give a yellow colored solution. After 3 hours stirring at −78° C., the reaction was warmed to room temperature and stirred for 1 hour. The reaction was quenched by addition of AcOH to pH 5∼6. The solvent was removed in vacuo and H₂O (100 ml) was added. The products were extracted with CH₂Cl₂ (100 ml×3), which was washed with saturated NaHCO₃, H₂O and dried over MgSO₄. Filtration and evaporation of solvent left a yellow oil. This was fractionated to give the desired compound (8.1 g, 31.6 mmol, 63%, b.p. 142°–144°/0.2 mm Hg).

C. [1β,2α,3α(1E),4β]-4-[2-[3-(3-Oxo-4-phenyl-1-pentenyl)-7-oxabicyclo[2.2.1]hept-2-yl]ethyl]benzoic acid, methyl ester Sodium hydride (201 mg of 50% in mineral oil, 4.18 mmol) is suspended in distilled dimethoxyethane (70 ml) in an argon atmosphere and treated with a solution of title B phosphonate (1.45 g, 4.7 mmol) in DME (10 ml). The mixture is stirred at room temperature 90 minutes. A solution of [1β,2α,3α,4β]-4-[2-[3-formyl-7oxabicyclo[2.2.1]hept-2-yl]ethyl]benzoic acid, methyl ester (prepared as described in Example 2) (3.8 mmol) in DME (5 ml) is then added and the mixture is stirred overnight at room temperature. The reaction is quenched by adding glacial acetic acid (0.5 ml) and the solvent is removed in vacuo. Ether and saturated NaHCO₃ are added and the layers are separated. The ether layer is washed once with saturated NaHCO₃ solution, dried over MgSO₄, filtered and taken to dryness in vacuo leaving a viscous oil. This is chromatographed on silica gel 60 (110 g) eluting with ether-pet ether (2:3) to give title C compound as an oil. A faster moving material is also isolated and identified by ¹H NMR as the cis double bond isomer.

D. [1β,2α,3α(1E,3α,4α),4β]-4-[2-[3-(3-Hydroxy-4-phenyl-1-pentenyl)-7oxabicyclo[2.2.1]hept-2-yl]ethyl]benzoic acid, methyl ester (fast moving isomer A)

Title C compound (2.49 mmol) and CeCl₃.7.6H₂O (0.954 g, 2.49 mmol) are dissolved in methanol (25 ml) and THF (2 ml). The solution is cooled in an ice bath and NaBH₄ (94.1 mg, 2.5 mmol) is added portionwise in 30 seconds. The ice bath is removed and the mixture is stirred 10 minutes, then poured into saturated NH₄Cl solution (200 ml). The product is extracted into ethyl acetate (5×50 ml). The combined ethyl acetate extracts are dried (MgSO₄), filtered and freed of solvent in vacuo to give a viscous oil (0.953 g). This is chromatographed on silica gel (60 g) eluting with ether-pet ether (3:2) to give nearly clean faster moving isomer and slower moving isomer ([1β,2α,3α(1E,3β),4β]-4-[2-[3-(3-hydroxy-4-phenyl-1-phenyl-1-pentenyl)-7-oxabicyclo[2.2.1]hept-2-yl]ethyl]benzoic acid, methyl ester). The faster moving isomer A is rechromatographed eluting with the same solvent to give title D compound.

E. [1β,2α,3α(1E,3α,4α),4β]-4-[2-[3-(3-Hydroxy-4-phenyl-1-pentenyl)-7-oxabicyclo[2.2.1]hept-2-yl]ethyl]benzoic acid (fast moving isomer A) and [1β,2α,3α(1E,3α,4β),4β]-4-[2-[3-(3-Hydroxy-4-phenyl-1-pentenyl)-7-oxabicyclo[2.2.1]hept-2-yl]ethyl]benzoic acid (fast moving isomer B)

The title D methyl ester (1.5 mmol) is dissolved in THF (75 ml) and water (13.5 ml) and treated with 1N LiOH solution (15 ml). The mixture is stirred at room temperature in an argon atmosphere for 5 hours. The pH is adjusted to 3 by adding saturated oxalic acid solution and then the mixture is poured into water (450 ml). The product is extracted into ether (3×200 ml). The combined ether extracts are washed with water (3×200 ml) and saturated NaCl solution (1×200 ml), dried (MgSO₄), filtered and taken to dryness in vacuo leaving an oil. This is chromatographed on silica gel 60 eluting with 3% MeOH in CH₂Cl₂ to give two isomers. The faster moving isomer A is [1β,2α,3α(1E,3α,4α),4β]-4-[2-[3-(3-hydroxy-4-phenyl-1-pentenyl)-7-oxabicyclo[2.2.1]hept-2-yl]ethyl]benzoic acid and a slower moving isomer B is [1β,2α,3α(1E,3α,4β),4β]-4-[2-[3-(3-hydroxy-4-phenyl-1-pentenyl)-7-oxabicyclo2.2.1]hept-2-yl]ethyl]benzoic acid.

EXAMPLE 22

[1β,2α,3α(1E,3β),4β]-4-[2-[3-(3-Hydroxy-4-phenyl-1-pentenyl)-7-oxabicyclo[2.2.1]hept-2-yl]ethyl]benzoic acid (slow moving isomer)

The slow moving isomer of methyl ester (0.36 mmol) described in Examples 20 and 21 is dissolved in THF (18 ml) and water (3.2 mg). 1N LiOH solution (3.6 ml) is added and the mixture is stirred at room temperature in an argon atmosphere for 5 hours. A saturated solution of oxalic acid is added to adjust the pH to 3 and the solution is poured into water (150 ml). The product is extracted into ether (3×75 ml) and the combined ether extracts are washed with water (3×75 ml) and saturated NaCl solution (75 ml). The solution is dried (MgSO₄), filtered and the solvent is removed in vacuo to give the title product.

EXAMPLE 23

[1β,2α,3α(1E,3α),4β]-4-[2-[3-Hydroxy-4-(2-methylphenyl)-1-butenyl]-7-oxabicyclo[2.2.1]hept-2-yl]ethyl]benzoic acid (fast moving isomer)

A. 2-Oxo-3-(2-Methylphenyl)propyl dimethyl phosphonate

A solution of distilled dimethyl methylphosphonate (9.1 ml, 10.5 g, 77 mmol) in distilled THF (130 ml) was cooled to −78° in an argon atmosphere and treated dropwise in 30 minutes with a solution of 1.15N n-butyl lithium (70 ml, 80 mmol) in hexane. After addition was complete the mixture was stirred at −78° C. for 30 minutes. A solution of the methyl ester of o-tolylacetic acid (6.56 g, 40 mmol) in THF (7 ml) was added dropwise in 15 minutes. After stirring at −78° C. for 3.5 hours the cooling bath was removed and stirring was continued for 1 hour. The reaction was quenched by adding HOAc to pH 6. The solvent was removed in vacuo. Water (100 ml) was added to the residue and the product was extracted into CH₂Cl₂ (3×100 ml). The combined extracts were washed once with saturated NaHCO₃ solution and once with water, dried (MgSO₄)

and freed of solvent in vacuo. The residue was distilled to give 3.8 g (37%) of the title compound, b.p. 133°–135°/0.1 mmHg.

B. [1β,2α,3α(1E,3α),4β]-4-[2-[3-[3-Oxo-4-(2-methylphenyl)-1-butenyl]-7-oxabicyclo[2.2.1]hept-2-ethyl]benzoic acid, methyl ester Sodium hydride (201 mg of 50% in mineral oil, 4.18 mmol) is suspended in distilled dimethoxyethane (70 ml) in an argon atmosphere. A solution of title A phosphonate (1.46 g, 5.7 mmol) in DME (7 ml) is added. The mixture is stirred at room temperature 90 minutes. A solution of [1β,2α,3α,4β]-4-[2-[3-formyl-7oxabicyclo[2.2.1]hept-2-yl]ethyl]benzoic acid, methyl ester (prepared as described in Example 2) (3.8 mmol) in DME (5ml) is added and the mixture is left stirring overnight at room temperature. The reaction is quenched by adding HOAc (0.5 ml). The solvent is removed in vacuo and ether and saturated NaHCO₃ solution are added to the residue. The layers are separated and the ether layer is washed with NaHCO₃ solution; dried (MgSO₄), and freed of solvent in vacuo leaving a yellow oil. This is chromatographed on silica gel 60 (110 g) eluting with ether-pet ether 1:2 to give title B compound.

C. [1β,2α,3α(1E,3α),4β]-4-[2-[3-[3-Hydroxy-4-(2-methylphenyl)-1-butenyl]-7-oxabicyclo[2.2.1]hept-2-yl]ethyl]benzoic acid, methyl ester (fast moving isomer)

Title B compound (2.33 mmol) and CeCl₃.7.6H₂O (896 ml, 2.33 mmol) are dissolved in methanol (25 ml) and THF (4 ml). After cooling to 0°–5° C., NaBH₄ (88 mg, 2.33 mmol) is added portionwise in 30 sec. The ice bath is removed and the mixture is stirred 10 minutes, and then poured into saturated NH₄Cl solution (175 ml). The product is extracted into ethyl acetate (5×50 ml), dried (MgSO₄) and freed of solvent in vacuo leaving an oil. This is chromatographed on silica gel 60 (110 g), eluting with ether-pet ether 3:2 to give title C fast moving isomer and slow moving isomer. TLC: silica gel, Et₂O-P.E 3:2, vanillin R$_f$=0.39 (FMI) and 0.21 (SMI).

D. [1β,2α,3α(1E,3α),4β]-4-[2-[3-[3-Hydroxy-4-(2-methylphenyl)-1-butenyl]-7-oxabicyclo[2.2.1]hept-2-yl]ethyl]benzoic acid (fast moving isomer)

The title C methyl ester (fast moving isomer) (1.2 mmol) is dissolved in THF (60 ml) and water (11 ml) in an argon atmosphere. Lithium hydroxide solution (1N, 12.0 ml) is added and the mixture is stirred at room temperature 6 hours. Saturated oxalic acid solution is added to adjust the pH to 3 and the mixture is then poured into water (450 ml). The product is extracted into ether (3×200 ml). The combined ether extracts are washed with water (3×200 ml) and saturated NaCl solution (1×200 ml), dried (MgSO₄) and freed of solvent in vacuo. The oil is purified by chromatography on silica gel 60 (50 g), eluting with 3% MeOH in CH₂Cl₂ to give the title product.

EXAMPLE 24

[1β,2α,3α(1E,3β),4β]-4-[2-[3-[3-Hydroxy-4-(2-methylphenyl)-1-butenyl]-7-oxabicyclo[2.2.1]hept-2-yl]ethyl]benzoic acid (slow moving isomer)

The slow moving isomer [1β,2α,3α(1E,3β),4β]-4-[2-[3-[3-hydroxy-4-(2-methylphenyl)-1-butenyl]-7-oxabicyclo[2.2.1]hept-2-yl]ethyl]benzoic acid, methyl ester (prepared as described in Example 23, part C), (0.46 mmol) is dissolved in THF (25 ml) and water (4 ml) in an argon atmosphere and treated with 1N LiOH solution (4.6 ml). The mixture is stirred at room temperature for 6.5 hours; the pH is then adjusted to 3 by adding a saturated solution of oxalic acid. The solution is poured into water (150 ml) and the product is extracted into ether (3×75 ml). The combined ether extracts are washed with water (3×75 ml) and saturated NaCl solution (75 ml), dried (MgSO₄) and freed of solvent in vacuo to give the title product.

EXAMPLE 25

[1β,2α,3α(1E,3α),4β]-4-[2-[3-[3-Hydroxy-4-(3-methylphenyl)-1-butenyl]-7-oxabicyclo[2.2.1]hept-2-yl]ethyl]benzoic acid (fast moving isomer)

A. 2-Oxo-3-(3-methylphenyl)propyl dimethyl phosphonate

A solution of distilled dimethyl methylphosphonate (9.1 ml, 10.5 g., 77 mmol) in distilled THF (130 ml) was cooled to −78° C. in an argon atmosphere and treated dropwise in 30 minutes with a solution of 1.15N n-butyl lithium (70 ml, 80 mmol) in hexane. After addition was complete, the mixture was stirred at −78° C. for 30 minutes. A solution of the methyl ester of m-tosylacetic acid (6.56 g, 40 mmol) in 7 ml THF was then added dropwise over a period of 15 minutes. After stirring at −78° C. 3½ hours the cooling bath was removed and the mixture was stirred an additional 60 minutes. The reaction was quenched by adding acetic acid to pH 6. The solvent was removed in vacuo and water (70 ml) was added to the residue. The product was extracted into CH₂Cl₂ (3×100 ml). The conbined extracts were washed once with water, dried (MgSO₄) and freed of solvent in vacuo. The residue was distilled in vacuo to give the title A phosphonate (5.6 g, 55%) boiling 133°–135°/0.1 mm.

B. [1β,2α,3α(1E,3α),4β]-4-[2-[3-[3-Oxo-4-(3-methylphenyl)-1-butenyl]-7-oxabicyclo[2.2.1]hept-2-yl]ethyl]benzoic acid, methyl ester Sodium hydride (201 mg of 50% in mineral oil, 4.18 mmol) is suspended in distilled dimethoxyethane in an argon atmosphere. A solution of title A phosphonate (5.7 mmol) in DME (7 ml) is added. After stirring at room temperature 90 minutes a solution of [1β,2α,3α,4β]-4-[2-[3-formyl-7-oxabicyclo[2.2.1]hept-2-yl]ethyl]benzoic acid, methyl ester (3.8 mmol) in DME (5 ml) is added. The mixture is left stirring overnight at room temperature then quenched by adding glacial HOAc (0.5 ml). The solvent is removed in vacuo. Ether and saturated NaHCO₃ solution are added to the residue. The layers are separated and the ether layer is washed once with NaHCO₃ solution, dried (MgSO₄), and freed of solvent in vacuo. This is chromatographed on silica gel 60 (110 g) eluting with ether-pet ether 1:2 to give title B compound as a colorless oil. A faster moving material is also isolated and identified as the cis double bond isomer.

C.
[1β,2α,3α(1E,3α),4β]-4-[2-[3-[3-Hydroxy-4-(3-methylphenyl)-1-butenyl]-7-oxabicyclo[2.2.1]hept-2-yl]ethyl]benzoic acid, methyl ester Title B compound (2.5 mmol) and $CeCl_3.7.6H_2O$ (0.968 g, 2.5 mmol) are dissolved in methanol (25 ml) and THF (2 ml). The solution is cooled in an ice bath and $NaBH_4$ (95.5 mg, 2.5 mmol) is added portionwise in 30 seconds. The ice bath is removed and the mixture is stirred 8 minutes, then poured into saturated $NH_4Cl$ solution (200 ml). The product is extracted into ethyl acetate (5×50 ml), dried and freed of solvent in vacuo. The remaining oil is chromatographed on silica gel 60 (110 g) eluting with ether-pet ether (1:1 and then 3:2) to give fast moving isomer and slow moving isomer.

D.
[1β,2α,3α(1E,3α),4β]-4-[2-[3-[3-Hydroxy-4-(3-methylphenyl)-1-butenyl]-7-oxabicyclo[2.2.1]hept-2-yl]ethyl]benzoic acid (fast moving isomer)

The title C fast moving isomer of the methyl ester (1.59 mmol) is dissolved in distilled THF (75 ml) and water (14 ml) in an argon atmosphere. The solution is treated with 1N LiOH solution (15.9 ml) and stirred at room temperature 6 hours. A saturated solution of oxalic acid is added to pH 3 and the solution is poured into water (450 ml). The product is extracted into ether (3×200 ml). The combined ether extracts are washed with water (3×200 ml) and saturated NaCl solution (1×200 ml), dried ($MgSO_4$) and freed of solvent in vacuo leaving a colorless oil. This is chromatographed on silica gel 60 (50 g) eluting with 3% MeOH in $CH_2Cl_2$ to give the title product.

EXAMPLE 26
[1β,2α,3α(1E,3β),4β]-4-[2-[3-(3-Hydroxy-4-(3-methylphenyl)-1-butenyl]-7-oxobicyclo[2.2.1]hept-2-yl]ethyl]benzoic acid (slow moving isomer)

The slow moving isomer of the methyl ester prepared in Example 25, Part C, that is, [1β,2α,3α(1E,3β),4β]-4-[2-[3-[3-hydroxy-4-(3-methylphenyl)-1-butenyl]-7-oxabicyclo[2.2.1]hept-2-yl]ethyl]benzoic acid, methyl ester (0.53 mmol) is dissolved in THF (25 ml) and water (5 ml) in an argon atmosphere. Lithium hydroxide solution (1N, 5.3 ml) is added and the mixture is stirred at room temperature 6.5 hours. The pH is adjusted to 3 by adding saturated oxalic acid solution and then the solution is poured into water (150 ml). The product is extracted with ether (3×75 ml). The combined extracts are washed with water (3×75 ml) and saturated NaCl solution (75 ml), dried ($MgSO_4$) and freed of solvent in vacuo to give the title product.

EXAMPLE 27
[1β,2α,3α(1E,3α),4β]-4-[2-[3-(3-Hydroxy-4-methyl-4-phenyl-1-pentenyl)-7-oxabicyclo[2.2.1]hept-2-yl]ethyl]benzoic acid (fast moving isomer)

A. 2-Oxo-3-methyl-3-phenylbutyl dimethyl phosphonate

Sodium hydride (374.4 mg of 50% in mineral oil, 7.8 mmol) was washed with freshly distilled THF (5 ml) and suspended in THF (78 ml). 2-Oxo-3-phenylbutyl dimethyl phosphonate (prepared as described in Example 20, Part B), (2.0 g, 7.8 mmol) was added dropwise at 0° C. The mixture was stirred one hour at room temperature then cooled to −78° C. and treated with a solution of n-BuLi in hexane (4.85 ml of 1.7M solution, 7.8 mmol). The reaction was stirred at −78° C. for 15 minutes and at 0° C. for 1 hour. Methyl iodide (1.5 ml, 24 mmol) was added and the mixture was stirred at 0° C. for 1 hour, then quenched by adding glacial acetic acid. The mixture was carefully poured into saturated $NaHCO_3$ solution and the product was extracted into ethyl acetate (3×150 ml). The combined extracts were washed with saturated $NaHCO_3$ solution and saturated NaCl solution, dried ($Na_2SO_4$) and freed of solvent in vacuo to give a brown oil. This was distilled by kugelrohr to give the title A phosphonate, 1.9 g (92%) boiling 170°/0.15 mm.

B.
[1β,2α,3α(1E,3α),4β]-4-[2-[3-(3-Oxo-4-methyl-4-phenyl-1-pentenyl)-7-oxabicyclo[2.2.1]hept-2-yl]ethyl]benzoic acid, methyl ester Sodium hydride (201 mg of 50% in mineral oil, 4.18 mmol) is suspended in 70 ml distilled dimethoxyethane in an argon atmosphere. A solution of title A phosphonate (1.54 g, 5.7 mmol) in DME (7 ml) is added and the mixture is stirred at room temperature 90 minutes. [1β,2α,3α,4β]-4-[2-[3-Formyl-7-oxabicyclo[2.2.1]hept-2-yl]ethyl]benzoic acid, methyl ester (3.8 mmol) in DME (5 ml) is added and the reaction mixture is left stirring overnight at room temperature. The reaction is quenched by adding glacial acetic acid (0.5 ml) and the solvent is removed in vacuo. Ether and saturated $NaHCO_3$ solution are added to the residue. The layers are separated and the ether layer is washed once with saturated $NaHCO_3$ solution, dried ($MgSO_4$) and freed of solvent in vacuo leaving a yellow oil. This is chromatographed on silica gel 60, eluting with ether-pet ether (2:5) to give title B compound.

C.
[1β,2α,3α(1E,3α),4β]-4-[2-[3-(3-Hydroxy-4-methyl-4-phenyl-1-pentenyl)-7-oxabicyclo[2.2.1]hept-2-yl]ethyl]benzoic acid, methyl ester (fast moving isomer)

The title B ketone (2.43 mmol) and $CeCl_3.7.6H_2O$ (0.932 g, 2.43 mmol) are dissolved in MeOH (25 ml). The solution is cooled in an ice bath and treated portionwise in 30 sec. with $NaBH_4$ (92 mg, 2.43 mmol). The ice bath is removed and the mixture is stirred 8 minutes, then poured into saturated $NH_4Cl$ solution (200 ml). The product is extracted into EtOAc (5×50 ml), dried ($MgSO_4$) and freed of solvent in vacuo to give an oil. This is chromatographed on silica gel 60 (60 g), eluting with ether-pet ether 2:3 to give title C fast moving isomer and slow moving isomer.

D.
[1β,2α,3α(1E,3α),4β]-4-[2-[3-(3-Hydroxy-4-methyl-4-phenyl-1-pentenyl)-7-oxabicyclo[2.2.1]hept-2-yl]ethyl]benzoic acid (fast moving isomer)

The fast moving isomer of methyl ester (title C) (1.67 mmol) is dissolved in THF (75 ml) and water (15 ml). Lithium hydroxide solution (16.7 ml of 1N solution) is then added and the mixture is stirred at room temperature 7 hours. A saturated solution of oxalic acid is added to pH 3 and the solution is poured into water (450 ml). The product is extracted with ether (3×200 ml) and the combined extracts are washed with water (3×200 ml) and saturated NaCl solution (1×200 ml), dried ($MgSO_4$) and freed of solvent in vacuo. The oil is chromatographed on silica gel 60 (40 g) eluting with 3% MeOH in CH₂Cl₂ to give the title product.

EXAMPLE 28

[1β,2α,3α(1E,3β),4β]-4-[2-[3-(3-Hydroxy-4-methyl-4-phenyl-1-pentenyl)-7-oxabicyclo[2.2.1]hept-2-yl]ethyl]benzoic acid (slow moving isomer)

The slow moving isomer of methyl ester prepared in Example 27, Part C, that is [1β,2α,3α(1E,3β),4β]-4-[2-[3-(3-hydroxy-4-methyl-4-phenyl-1-pentenyl)-7-oxabicyclo[2.2.1]hept-2-yl]ethyl]benzoic acid, methyl ester (0.23 mmol) is dissolved in tetrahydrofuran (12 ml) and water (2 ml). Lithium hydroxide solution (2.3 ml of 1N) is added and the mixture is stirred at room temperature 6.5 hours. Saturated oxalic acid solution is added to pH 3 and the solution is poured into water (100 ml). The product is extracted into ether (3×50 ml). The combined ether extracts are washed with water (3×50 ml) and saturated NaCl solution (1×50 ml), dried (MgSO₄) and freed of solvent in vacuo to give the title product.

EXAMPLE 29

[1β,2α,3α(1E,3α),4β]-4-[2-[3-[3-Hydroxy-3-(1-methylcyclohexyl)-1-propenyl]-7-oxabicyclo[2.2.1]hept-2-yl]ethyl]benzoic acid (fast moving isomer)

A. 2-Oxo-2-(1-methylcyclohexyl)dimethyl phosphonate n-BuLi (1.15M solution of hexane, 70 ml, 80 mmol) was added dropwise to a stirred solution of distilled dimethyl methylphosphonate (9.1 ml, 10.5 g, 77 mmol) in THF (130 ml) at −78° C. Stirring was continued for 30 minutes at −78° and then a solution of the methyl ester of 1-methyl-1-cyclohexanecarboxylic acid (6.24 g, 40 mmol) in THF (8 ml) was added dropwise over a period of 15 minutes. The mixture was stirred at −78° C. for 3.5 hours and then at room temperature for 2 hours. The reaction was quenched by addition of HOAc to pH ~6. The solvent was removed in vacuo and water (70 ml) was added to the residue. The product was extracted into CH₂Cl₂ (3×100 ml). The combined extracts were washed once with water, dried (MgSO₄) and freed of solvent in vacuo leaving an oil. This was distilled to give the title compound (6.0 g, 60.5%) boiling 120°-122°/0.2 mm.

B.
[1β,2α,3α(1E,3α),4β]-4-[2-[3-[3-Oxo-3-(1-methylcyclohexyl)-1-propenyl]-7-oxabicyclo[2.2.1]hept-2-yl]ethyl]-benzoic acid, methyl ester Sodium hydride (201 mg of 50% in mineral oil, 4.18 mmol) is suspended in distilled dimethoxyethane (70 ml) in an argon atmosphere and treated with a solution of title A phosphonate (1.42 g, 5.7 mmol) in DME (7 ml). The mixture is stirred at room temperature 90 minutes. A solution of [1β,2α,3α,4β]-4-[2-[3-formyl-7-oxabicyclo[2.2.1]hept-2-yl]ethyl]benzoic acid, methyl ester (3.8 mmol) in DME (5 ml) is added and the mixture is left stirring overnight at room temperature. The reaction is quenched by adding glacial acetic acid (0.5 ml) and the solvent is removed in vacuo. Ether and saturated NaHCO₃ solution are added and the layers are separated. The ether layer is washed once with saturated NaHCO₃ solution, dried (MgSO₄), and freed of solvent in vacuo leaving a yellow oil. This is chromatographed on silica gel 60 (110 g), eluting with ether-pet ether 1:2 to give title B compound.

A faster moving material is also isolated and identified as the cis double bond isomer.

C.
[1β,2α,3α(1E,3α),4β]-4-[2-[3-[3-Hydroxy-3-(1-methylcyclohexyl)-1-propenyl]-7-oxabicyclo[2.2.1]hept-2-yl]ethyl]benzoic acid, methyl ester (fast moving isomer)

Title B compound (3.1 mmol) and CeCl₃.7.6H₂O (1.18 g, 3.1 mmol) are dissolved in methanol (30 ml) and THF (2 ml). The solution is cooled in an ice bath and sodium borohydride (117 mg, 3.1 mmol) is added portionwise over a period of 30 seconds. The ice bath is removed and the mixture is stirred 8 minutes, then poured into saturated NH₄Cl solution (200 ml). The product is extracted into EtOAc (5×50 ml), dried and freed of solvent in vacuo leaving an oil. This is chromatographed on silica gel 60 (80 g) eluting with ether-pet ether (1:1) to give material enriched in title C fast moving isomer and slow moving isomer. The fast moving isomer is rechromatographed on silica gel 60 eluting with 10% ethyl acetate in benzene to give clean title C compound.

D.
[1β,2α,3α(1E,3α),4β]-4-[2-[3-[3-Hydroxy-3-(1-methylcyclohexyl)-1-propenyl]-7-oxabicyclo[2.2.1]hept-2-yl]ethyl]benzoic acid (fast moving isomer)

The title C methyl ester (fast moving isomer, 1.54 mmol) is dissolved in THF (75 ml) and water (14 ml) in an argon atomsphere and treated with 1N LiOH solution (15.4 ml). The mixture is stirred at room temperature 6.5 hours. The pH is then adjusted to 3 by adding saturated oxalic acid solution and the solution is poured into water (450 ml). The product is extracted into ether (3×200 ml). The combined ether extracts are washed with water (3×200 ml) and saturated NaCl solution (1×200 ml), dried and freed of solvent in vacuo leaving an oil. This is purified by chromatography on silica gel 60 (40 g), eluting with 3% MeOH in CH₂Cl₂ to give the title product.

EXAMPLE 30

[1β,2α,3α(1E,3β),4β]-4-[2-[3-[3-Hydroxy-3-(1-methylcyclohexyl)-1-propenyl]-7-oxabicyclo[2.2.1]-hept-2-yl]ethyl]benzoic acid (slow moving isomer)

The slow moving methyl ester prepared in Example 29, Part C, that is [1β,2α,3α(1E,3β),4β]-4-[2-[3-[3-hydroxy-3-(1-methylcyclohexyl)-1-propenyl]-7-oxabicyclo[2.2.1]hept-2-yl]ethyl]benzoic acid, methyl ester (0.36 mmol) is dissolved in THF (18 ml) and water (3.2 ml) in an argon atmosphere. The solution is treated with 1N LiOH solution (3.6 ml) and stirred at room temperature 6.5 hours. A saturated solution of oxalic acid is added to pH 3 and the mixture is poured into water (150 ml). The product is extracted into ether (3×75 ml). The combined ether extracts are washed with water (3×75 ml) and saturated NaCl solution (1×75 ml), dried (MgSO₄) and freed of solvent in vacuo leaving an oil. This is chromatographed on silica gel 60 (15 g) eluting with 3% MeOH in CH₂Cl to give the title product (slow moving isomer).

EXAMPLE 31

[1β,2α,3α(1E,3α),4β]-4-[2-[3-[3-Hydroxy-4-(4-methylphenyl)-1-butenyl]-7-oxabicyclo[2.2.1]hept-2-yl]-ethyl]-benzoic acid (fast moving isomer)

A. 2-Oxo-3-(4-methylphenyl)propyl dimethyl phosphate

A solution of distilled dimethyl methylphosphonate (5.6 ml, 6.44 g, 47 mmol) in dist. THF (80 ml) was cooled to −78° C. in an argon atmosphere and treated dropwise in 30 minutes with a solution of 1.65M n-butyl lithium in hexane (30 ml, 49 mmol). After addition was complete, the mixture was stirred at −78° for 30 minutes. A solution of the methyl ester of p-tolylacetic acid (4.025 g, 24.5 mmol) in 5 ml THF was added dropwise in 15 minutes. After stirring at −78° C. for 3.5 hours the cooling bath was removed and the mixture was stirred an additional 60 minutes. The reaction was quenched by adding acetic acid to pH 6. The solvent was removed in vacuo and water (75 ml) was added to the residue. The product was extracted into $CH_2Cl_2$ (3×75 ml). The combined extracts were washed once with saturated $NaHCO_3$ solution (75 ml) and once with water (75 ml), dried ($MgSO_4$) and freed of solvent in vacuo leaving an oil. This was distilled in vacuo to give the title phosphonate (3.06 g, 49%) boiling 132°-134°/0.1 mm.

B. [1β,2α,3α(1E,3α),4β]-4-[2-[3-[3-Oxo-4-(4-methylphenyl)-1-butenyl]-7-oxabicyclo[2.2.1]hept-2-yl]ethyl]-benzoic acid, methyl ester Sodium hydride (201 mg of 50% in mineral oil, 4.18 mmol) is suspended in distilled dimethoxyethane (70 ml) in an argon atmosphere. A solution of title A phosphonate (1.46 g, 5.7 mmol) in DME (7 ml) is added. A fluffy solid precipitates out. After stirring at room temperature 90 minutes a solution of 1β,2α,3α,4β]-4-[2-[3-formyl-7-oxabicyclo[2.2.1]hept-2-yl]ethyl]benzoic acid, methyl ester (3.8 mmol) in DME (5 ml) is added. The mixture is left stirring overnight at room temperature, then quenched by adding glacial HOAc (0.5 ml). The solvent is removed in vacuo. Ether and saturated $NaHCO_3$ solution are added to the residue. The layers are separated and the organic layer is washed once with $NaHCO_3$ solution, dried ($MgSO_4$) and freed of solvent in vacuo to give material which crystallizes on standing. This is chromatographed on silica gel 60 eluting with ether-pet ether 1:3 to give title B compound which crystallizes. A faster moving material is also isolated and identified as the cis double bond isomer.

C. [1β,2α,3α(1E,3α),4β]-4-[2-[3-[3-Hydroxy-4-(4-methylphenyl)-1-butenyl]-7-oxabicyclo[2.2.1]hept-2-yl]ethyl]-benzoic acid, methyl ester Title B compound (2.66 mmol) and $CeCl_3.7.6H_2O$ (1.02 g, 2.66 mmol) are dissolved in methanol (25 ml) and THF (2 ml). The solution is cooled in an ice bath and $NaBH_4$ (101 mg, 2.66 mmol) is added portionwise in 30 seconds. The cooling bath is removed and the mixture is stirred 10 minutes, then poured into saturated $NH_4Cl$ solution (175 ml). The product is extracted into ethyl acetate (5×50 ml), dried ($MgSO_4$), and freed of solvent in vacuo leaving an oil. This is chromatographed on silica gel (100 g) eluting with $Et_2O$-pet ether 3:2 to give title C compound (fast moving isomer) and slow moving isomer.

D. [1β,2α,3α(1E,3α),4β]-4-[2-[3-[3-Hydroxy-4-(4-methylphenyl)-1-butenyl]-7-oxabicyclo[2.2.1]hept-2-yl]ethyl]-benzoic acid (fast moving isomer)

The fast moving isomer of methyl ester (title C) (1.5 mmol) is dissolved in THF (75 ml) and water (14 ml) in an argon atmosphere. The solution is treated with 1N LiOH solution (15 ml) and stirred at room temperature 7 hours. Saturated oxalic acid solution is added to pH 3 and the solution is poured into water (450 ml). The product is extracted into ether (3×200 ml). The combined ether extracts are washed with water (3×200 ml) and saturated NaCl solution (1×200 ml), dried ($MgSO_4$) and freed of solvent in vacuo. The remaining oil is chromatographed on silica gel 60 (50 g) eluting with 3% MeOH in $CH_2Cl_2$ to give clean title product.

EXAMPLE 32

[1β,2α,3α(1E,3β),4β]-4-[2-[3-[3-Hydroxy-4-(4-methylphenyl)-1-butenyl]-7-oxabicyclo[2.2.1]hept-2-yl]ethyl]-benzoic acid (slow moving isomer)

The slow moving isomer of methyl ester, described in Example 31, Part B, (0.46 mmol) is dissolved in THF (25 ml) and water (4 ml) in an argon atmosphere. 1N LiOH solution (4.6 ml) is added and the mixture is stirred at room temperature 7 hours. The pH is adjusted to 3 by adding saturated oxalic acid solution and the solution is then poured into water (150 ml). The product is extracted into ether (3×75 ml). The combined extracts are washed with water (3×75 ml) and saturated NaCl solution (75 ml), dried ($MgSO_4$) and freed of solvent in vacuo to give the title product.

EXAMPLE 33

[1β,2α,3α(1E,3α,4α),4β]-4-[2-[3-(3-Hydroxy-4-phenyl-1-hexenyl)-7-oxabicyclo[2.2.1]hept-2-yl]ethyl]benzoic acid (fast moving isomer)

A. 2-Oxo-3-phenylpentyl dimethyl phosphonate

A solution of distilled dimethyl methylphosphonate (12.8 ml, 14.75 g. 108 mmol) in distilled THF (180 ml) was cooled to −78° C. in an argon atmosphere. While stirring, a solution of n-butyl lithium in hexane (1.65M, 68 ml, 112.4 mmol) was added dropwise over a period of 30 minutes. The mixture was stirred at −78° for an additional 30 minutes and then treated dropwise in 15 minutes with a solution of the methyl ester of 2-phenylbutyric acid (10.0 g, 56.2 mmol) in THF (15 ml). Stirring at −78° C. was continued for 3.5 hours. The cooling bath was then removed and after 75 minutes glacial acetic acid was added to pH 6. Most of the solvent was then removed in vacuo and water (100 ml) was added. The product was extracted into $CH_2Cl_2$ (3×125 ml). The combined extracts were washed with saturated $NaHCO_3$ solution (1×100 ml) and water (1×100 ml), dried ($MgSO_4$) and freed of solvent in vacuo. The title phosphonate was distilled giving 10.5 g (69%) boiling 134°-136°/0.1 mm.

B. [1β,2α,3α(1E,3α,4α),4β]-4-[2-[3-[3-Oxo-4-phenyl-1-hexenyl)-7-oxabicyclo[2.2.1]hept-2-yl]ethyl]benzoic acid, methyl ester Sodium hydride (50% in mineral oil, 201 mg, 4.18 mmol) is suspended in distilled dimethoxyethane (70 ml) in an argon atmosphere. A solution of title A phosphonate (1.54 g, 5.7 mmol) in DME (7 ml) is added. After stirring at room temperature for 90 minutes a solution of [1β,2α,3α,4β]-4-[2-[3-formyl-7-oxabicyclo[2.2.1]hept-2-yl]ethyl]benzoic acid, methyl ester (3.8 mmol) in DME (5 ml) is added. The mixture is stirred overnight at room temperature and then quenched by adding glacial acetic acid (0.5 ml). The solvent is removed in vacuo. Ether and saturated NaHCO₃ solution are added to the residue and the layers are separated. The ether layer is washed once with saturated NaHCO₃ solution, dried (MgSO₄) and freed of solvent in vacuo leaving an oil. This is purified by HPLC followed by chromatography on 100 g silica gel 60, eluting with ether-pet ether (1:3) to give title compound.

C.
[1β,2α,3α(1E,3α,4α),4β]-4-[2-[3-[3-Hydroxy-4-phenyl-1-hexenyl]-7-oxabicyclo[2.2.1]hept-2-yl]ethyl]benzoic acid, methyl ester Title B compound (2.73 mmol) and CeCl₃.7.6H₂O (1.047 g, 2.73 mmol) are dissolved in methanol (25 ml) in an argon atmosphere. The solution is cooled in an ice bath and NaBH₄ (104 mg, 2.73 mmol) is added portionwise in 20 seconds. The cooling bath is removed and after stirring 8 minutes the mixture is poured into saturated NH₄Cl solution (175 ml). The product is extracted into ethyl acetate (5×50 ml), dried (MgSO₄) and freed of solvent in vacuo. The remaining oil is chromatographed on silica gel 60 (100 g) eluting with ether-pet ether (55:45) to give title C product (fast moving isomer) and slow moving isomer.

D.
[1β,2α,3α(1E,3α,4α),4β]-4-[2-[3-(3-Hydroxy-4-phenyl-1-hexenyl)-7-oxabicyclo[2.2.1]hept-2-yl]ethyl]benzoic acid (fast moving isomer)

The fast moving isomer from Part C (1.58 mmol) is dissolved in THF (75 ml) and water (14 ml) in an argon atmosphere and treated with 1N LiOH solution (15.8 ml). The mixture is stirred at room temperature 6.5 hours and then acidified to pH 3 with saturated oxalic acid solution. After pouring into water (450 ml), the product is extracted into ether (3×200 ml). The combined extracts are washed with water (3×200 ml) and saturated NaCl solution (200 ml), dried (MgSO₄) and freed of solvent in vacuo. The remaining oil includes fast moving isomer A and fast moving isomer B. This is chromatographed on silica gel 60 (80 g) eluting with 3% MeOH in CH₂Cl₂ to give 3 pools-a) greatly enriched in the title isomer A, b) mixture and c) enriched isomer B. The title isomer A enriched pool is rechromatographed on silica gel 60 (40 g), eluting with 2% MeOH in CH₂Cl₂ to give title isomer A appearing clean on TLC.

EXAMPLE 34
[1β,2α,3α(1E,3α,4β),4β]-4-[2-[3-(3-Hydroxy-4-phenyl-1-hexenyl)-7-oxabicyclo[2.2.1]hept-2yl]ethyl]benzoic acid (fast moving isomer B)

The pool (194 mg) described in Example 33 Part D as being enriched in isomer B is rechromatographed on silica gel 60 (30 g), eluting with 2.5% MeOH in CH₂Cl₂ to give the title isomer, (fast moving isomer B).

EXAMPLE 35
[1β,2α,3α(1E,3β),4β]-4-[2-[3-(3-Hydroxy-4-phenyl-1-heptenyl)-7-oxabicyclo[2.2.1]hept-2-yl]ethyl]benzoic acid (slow moving isomer)

The slow moving isomer described in Example 33, Part C (0.44 mmol) is dissolved in THF (25 ml) and water (4 ml) in an argon atmosphere and treated with 1N LiOH solution (4.4 ml). After stirring at room temperature 7 hours the pH is adjusted to 3 by adding saturated oxalic acid solution. The mixture is poured into water (150 ml) and extracted with ether (3×75 ml). The combined ether extracts are washed with water (3×75 ml) and saturated NaCl solution (75 ml), dried (MgSO₄) and freed of solvent in vacuo leaving an oil. The oil is chromatographed on silica gel 60 (30 g) eluting with 3% MeOH in CH₂Cl₂, to give the title product.

EXAMPLE 36
[1β,2α,3β,4β]-4-[2-[3-[[(Propoxycarbonyl)hydrazono]methyl]-7-oxabicyclo[2.2.1]hept-2-yl]ethyl]benzoic acid

A. n-Propyl hydrazinocarboxylate

Hydrazine hydrate (1.9 g, 0.038 mmol) and di-n-propyl carbonate (5.3 g, 0.036 mmol) were heated at reflux for 43 hours. The reaction was filtered and the filtrate was concentrated in vacuo to leave a colorless oil (3.5 g, 0.029 mol, 82%).

B.
[1β,2α,3β,4β]-4-[2-[3-Formyl-7-oxabicyclo[2.2.1]hept-2-yl]ethyl]benzoic acid, methyl ester The aldehyde from Example 2, Part J, namely, [1β,2α,3α,4β]-4-[2-[3-formyl-7-oxabicyclo[2.2.1]hept-2-yl]ethyl]benzoic acid, methyl ester is dissolved in 10 ml of methanol and to this solution is added 27 mg of sodium methoxide. The reaction is stirred at 25° for 2 hours, then poured into 300 ml of saturated ammonium chloride and extracted with three 100 ml portions of ether. The combined ethereal extract is washed with 50 ml of brine, dried over anhydrous magnesium sulfate and concentrated to give the title aldehyde.

C.
[1β,2α,3β,4β]-4-[2-[3-[[(Propoxycarbonyl)hydrazono]methyl]-7-oxabicyclo[2.2.1]hept-2-yl]ethyl]benzoic acid, methyl ester

[1β,2α,3β,4β]-4-[2-[3-Formyl-7-oxabicyclo[2.2.1]hept-2-yl]ethyl]benzoic acid, methyl ester, (prepared as described in Part A employing the appropriate starting hydroxymethyl isomer) (2 mmol) is dissolved in distilled ethanol (10 ml) in an argon atmosphere and the title A compound (260 mg, 2.2 mmol) is added. The mixture is stirred at room temperature 3 hours and then taken to dryness in vacuo. The oily residue is chromatographed on silica gel 60 (30 g), eluting with ether-pet ether 3:1 to give the title compound as a viscous oil.

D.
[1β,2α,3β,4β]-4-[2-[3-[[(Propoxycarbonyl)hydrazono]methyl]-7-oxabicyclo[2.2.1]hept-2-yl]ethyl]benzoic acid Title C compound (0.89 mmol) is dissolved in THF (40 ml) and water (7.8 ml) in an argon atmosphere. 1N LiOH solution (8.9 ml) is added and the mixture is stirred at room temperature 5.5 hours. 1N HCl (10.4 ml) is added to adjust pH to 3. The solution is poured into saturated NaCl solution (300 ml). The product is extracted into ethyl acetate (4×100 ml). The combined ethyl acetate extracts are washed with saturated NaCl solution (4×100 ml), dried over MgSO₄, filtered and freed of solvent in vacuo to give the title product.

EXAMPLE 37

[1β,2α,3α,4β]-4-[2-[3-[[(Propoxycarbonyl)hydrazono]methyl]-7-oxabicyclo[2.2.1]hept-2-yl]ethyl]benzoic acid

A.

[1β,2α,3α,4β]-4-[2-[3-[[(Propoxycarbonyl)hydrazono]methyl]-7-oxabicyclo[2.2.1]hept-2-yl]ethyl]benzoic acid, methyl ester

[1β,2α,3α,4β]-4-[2-[3-Formyl-7-oxabicyclo[2.2.1]hept-2-yl]ethyl]benzoic acid, methyl ester, (prepared as described in Example 2, employing the appropriate starting hydroxymethyl isomer) (2 mmol) and n-propyl hydrazinocarboxylate, prepared as described in Example 36, Part A, (283.2 mg, 2.4 mmol) are dissolved in EtOH (10 ml) and the reaction is stirred for 2 hours at room temperature. The reaction is concentrated in vacuo leaving a colorless oil (672 mg), which is purified by silica gel column (silica 60, 30 g) eluted with Et₂O/pet ether (3.5/1.5) to give a colorless oil.

B.

[1β,2α,3α,4β]-4-[2-[3-[[(Propoxycarbonyl)hydrazono]methyl]-7-oxabicyclo[2.2.1]hept-2-yl]ethyl]benzoic acid 1N-LiOH (6.7 ml) is added to title A ester (0.67 mmol) dissolved in THF (34 ml) and H₂O (6.7 ml) at room temperature. The reaction is stirred for 6 hours at room temperature. 1N-HCl (6.7 ml) is added to the reaction, which is poured into brine (~50 ml). The products are extracted with EtOAc (100 ml×3). The combined EtOAc layers are washed with brine (50 ml×2), and dried over MgSO₄. Filtration and evaporation of solvents affords an oil which is purified by silica gel column (silicar CC-7, 25 g) eluted with CH₂Cl₂/MeOH (9.75/0.25) to give the title product.

EXAMPLE 38

[1β,2α,3α,4β]-4-[2-[3-[[(Propoxycarbonyl)methylhydrazono]methyl]-7-oxabicyclo[2.2.1]hept-2-yl]ethyl]benzoic acid

A. 1-Methyl-1-propoxycarbonyl hydrazine

Methylhydrazine (7.2 g, 1.16 mole) and di-n-propylcarbonate (5 g, 0.034 mole) were stirred at room temperature for 96 hours to yield 1-methyl-1-propoxycarbonyl hydrazine and 2-methyl-1-propoxycarbonyl hydrazine in approximately equal amounts. The reaction was concentrated in vacuo and fractionated (F1, 2.0 g, 72°-76° a/0.8 mm Hg; F2, 1.1 g, 76°-88° a/0.8 mm Hg; F3, 1.1 g, 88°-90° a/0.8 mm Hg). F1 was a mixture of 1-methyl-1-propoxycarbonyl hydrazine and 2-methyl-1-propoxycarbonyl hydrazine in 4 to 1 ratio. F2 was an equal mixture of 1-methyl-1-propoxycarbony hydrazine and 2-methyl-1-propoxycarbonyl hydrazine. F3 was mostly 2-methyl-1-propoxycarbonyl hydrazine. Thus the yield of 1-methyl-1-propoxycarbonyl hydrazine was ca. 46%.

B.

[1β,2α,3α,4β]-4-[2-[3-[[(Propoxycarbonyl)methyl]hydrazono]methyl]-7-oxabicyclo[2.2.1]hept-2-yl]ethyl]benzoic acid, methyl ester A mixture of carbazate (1-methyl-1-propoxycarbonyl hydrazine and 2-methyl-1-propoxycarbonyl hydrazine) in a ratio of 1:1, (356 mg, 2.70 mmole) and [1β,2α,3α,4β]-4-[2-[3-formyl-7-oxabicyclo[2.2.1]hept-2-yl]ethyl]benzoic acid, methyl ester prepared as described in Example 2 (1.35 mmole) in MeOH (5 ml) are stirred at room temperature for 17 hours. The reaction is concentrated in vacuo and the residue is purified by SiO₂ column (SiO₂, 40 g) eluted with pet ether/ether-½ to give a colorless oil.

C.

[1β,2α,3α,4β]-4-[2-[3-[[(Propoxycarbonyl)methylhydrazono]methyl]-7-oxabicyclo[2.2.1]hept-2-yl]ethyl]benzoic acid 1N-LiOH (10 ml) is added to a magnetically stirred solution of the title B carbazone (381.5 mg, 1 mmole) in THF (50 ml) and H₂O (10 ml). Stirring is continued for 4.5 hours. 1N HCl (10 ml) and solid NaCl are added until the water layer is saturated. Then the products are extracted with EtOAc (70 ml×2), which is washed with brine once, and dried over MgSO₄. Filtration and evaporation of solvent gives an oil which is purified by SiO₂ column (silicar CC-7, 30 g) eluted with CH₂Cl/MeOH=9.8/0.2 to give the title product.

EXAMPLE 39

[1β,2α,3β,4β]-4-[2-[3-[[(Propoxycarbonyl)methylhydrazono]methyl]-7-oxabicyclo[2.2.1]hept-2-yl]ethyl]benzoic acid Following the procedure of Example 36 except substituting 1-methyl-1-propoxycarbonyl hydrazine for n-propyl hydrazinocarboxylate, the title compound is obtained.

EXAMPLE 40

[1β,2α,3α,4β]-4-[2-[3-[[(1-Oxopentyl)methylhydrazono]methyl]-7-oxabicyclo[2.2.1]hept-2-yl]ethyl]benzoic acid Following the procedure of Example 37 except substituting 1-methyl-1-pentanoyl hydrazine (prepared by reacting valeryl chloride and methyl hydrazine) for n-propyl hydrazinocarboxylate, the title compound is obtained.

EXAMPLE 41

[1β,2α,3β,4β]-4-[2-[3-[[(1-Oxopentyl)methylhydrazono]methyl]-7-oxabicyclo[2.2.1]hept-2-yl]ethyl]benzoic acid

A.

[1β,2α,3β,4β]-4-[2-[3-[[(1-Oxopentyl)methylhydrazono]methyl]-7-oxabicyclo[2.2.1]hept-2-yl]ethyl]benzoic acid, methyl ester A solution of the [1β,2α,3β,4β]-4-[2-[3-formyl-7-oxabicyclo[2.2.1]hept-2-yl]ethyl]benzoic acid, methyl ester (prepared as described in Example 36), (2 mmol) and 1 methyl-1-pentanoyl hydrazine, prepared as described in Example 40, (286 mg, 2.2 mmol) in EtOH (10 ml) is stirred at room temperature for 2 hours. The reaction mixture is poured into 100 ml of ether and washed with 1N HCl (2×20 ml), saturated NaHCO₃ solution (2×20 ml) and saturated NaCl solution (2×20 ml). The ether solution is dried over MgSO₄, filtered and freed of solvent in vacuo leaving 748 mg (99%) of oil. This is chromatographed on 30 g silica gel 60, eluting with ether to give title A compound as a viscous oil.

B.
[1β,2α,3β,4β]-4-[2-[3-[[(1-Oxopentyl)-methylhydrazono]methyl]-7-oxabicyclo[2.2.1]hept-2-yl]ethyl]-benzoic acid Title A compound (0.62 mmol) is dissolved in THF (30 ml) and water (5.8 mg). A solution of 1N LiOH (6.2 ml) is added and the mixture is stirred at room temperature 4.5 hours. 1N HCl (9 ml) is then added and the solution is poured into saturated NaCl solution (250 ml). The product is extracted into ethyl acetate (3 × 100 ml). The combined ethyl acetate extracts are washed with saturated NaCl solution (4 × 100 ml), dried over MgSO₄, filtered and freed of solvent in vacuo leaving glossy material. This is chromatographed on 18 g silica gel 60 eluting with 3% MeOH in CH₂Cl₂ to give clean title product as a viscous oil.

EXAMPLE 42
[1β,2α,3β,4β]-4-[2-[3-[(Ethylbenzoylhydrazono)methyl]-7-oxabicyclo]2.2.1]hept-2-yl]ethyl]benzoic acid

A.
[1β,2α,3β,4β]-4-[2-[3-[(Ethylbenzoylhydrazono)methyl]-7-oxabicyclo[2.2.1[hept-2-yl]ethyl]benzoic acid, methyl ester 1-Ethyl-1-benzoyl hydrazine (360 mg, 2.2 mmol) is added to a solution of [1β,2α,3β,4β]-4-[2-[3-formyl-7-oxabicyclo[2.2.1]hept-2-yl]ethyl]benzoic acid, methyl ester, prepared as described in Example 36 (2 mmol) in 10 ml dist EtOH in an argon atmosphere. The mixture is stirred at room temperature 2 hours and then poured into 100 ml ether. The ether solution is washed with 1N HCl (2 × 20 ml), saturated NaHCO₃ solution (2 × 20 ml) and saturated NaCl solution (2 × 20 ml), dried over MgSO₄, filtered and freed of solvent in vacuo leaving 667 mg oil. This is chromatographed on 38 g silica gel 60, eluting with ether to give clean methyl ester as a viscous oil.

B.
[1β,2α,3β,4β]-4-[2-[3-[(Ethylbenzoylhydrazono)methyl]-7-oxabicyclo[2.2.1]hept-2-yl]ethyl]benzoic acid The methyl ester of Part A (0.69 mmol) is dissolved in 35 ml THF and 6.5 ml water in an argon atmosphere and 1N LiOH solution (6.9 ml) was added. The mixture is stirred at room temperature 3½ hours and then 1N HCl solution (13.8 ml) is added. The solution is poured into 250 ml saturated NaCl solution and the product is extracted into ethyl acetate (3 × 100 ml). The combined ethyl acetate extracts are washed with saturated NaCl solution (4 × 100 ml), dried over MgSO₄, filtered and freed of solvent in vacuo leaving 217 mg oil. This is chromatographed twice on silica gel 60. The first column is eluted with 5% MeOH in EtOAc and the second column is eluted with 3% MeOH in EtOAc to give the title product as a foam.

EXAMPLE 43
[1β,2α,3α,4β]-4-[2-[3-(Ethylbenzoylhydrazono)methyl]-7-oxabicyclo[2.2.1]hept-2-yl]ethyl]benzoic acid

A.
[1β,2α,3α,4β]-4-[2-[3-[(Ethylbenzoylhydrazono)methyl]-7-oxabicyclo[2.2.1]hept-2-yl]ethyl]benzoic acid, methyl ester 1-Ethyl-1-benzoyl hydrazine (328 mg) is added to [1β,2α,3α,4β]-4-[2-[3-formyl-7-oxabicyclo[2.2.1]hept-2-yl]ethyl]benzoic acid, methyl ester (prepared as described in Example 2) (2 mmol) dissolved in EtOH (10 ml) and a drop of AcOH and stirred overnight. The reaction is poured into Et₂O (150 ml), which is washed with 1N HCl (30 ml × 2), NaHCO₃ (saturated, 30 ml × 2), brine (30 ml × 2) and dried over MgSO₄. Filtration and evaporation of solvent in vacuo give a yellow oil (812 mg), which is purified by a silica gel column (SiO₂, 30 g) eluted with CH₂Cl₂/MeOH (9.5/0.5) to give the title A hydrazone.

B.
[1β,2α,3α,4β]-4-[2-[3-[(Ethylbenzoylhydrazono)methyl]-7-oxabicyclo[2.2.1]hept-2-yl]ethyl]benzoic acid The hydrazone from Part A (0.78 mmol) is dissolved in THF (40 ml) and H₂O (8 ml), and cooled to 0° C. 1N LiOH (7.7 ml) is added. Stirring is continued at 0° C. for 4¼ hours. The reaction is quenched by addition of 10% oxalic acid to pH 3 and then poured into H₂O (200 ml). The products are extracted with EtOAc (150 ml × 3) and the combined EtOAc layers are washed with H₂O (50 ml × 3), brine (50 ml) and dried over MgSO₄. Filtration and evaporation of solvent in vacuo give a colorless oil, which is purified by a silica column (silica 60, 25 g) eluted with CH₂Cl₂/MeOH (9.5/0.5) to give anti isomer of the title hydrazone.

EXAMPLE 44
[1β,2α,3β,4β]-4-[2-[3-[[[(Phenylamino)carbonyl]-methylhydrazono]methyl]-7-oxabicyclo[2.2.1]hept-2-yl]ethyl]benzoic acid

A.
[1β,2α,3β,4β]-4-[2-[3-[[[(Phenylamino)-carbonyl]methylhydrazono]methyl]-7-oxabicyclo[2.2.1]hept-2-yl]ethyl]benzoic acid, methyl ester

[1β,2α,3β,4β]-4-[2-[3-Formyl-7-oxabicyclo[2.2.1-]hept-2-yl]ethyl]benzoic acid, methyl ester, (prepared as described in Example 36) (2 mmol) is dissolved in 10 ml dist. ethanol and treated with 2-methyl-4-phenyl semicarbazide (363 mg, 2.2 mmol) in an argon atmosphere. The mixture is stirred at room temperature 3 hours, then taken to dryness in vacuo. The residue is chromatographed on silica gel 60 (40 g), eluting with ether-pet ether (3:1) and ether to give the title anti isomer.

B.
[1β,2α,3β,4β]-4-[2-[3-[[[(Phenylamino)carbonyl]methylhydrazono]methyl]-7-oxabicyclo[2.2.1]hept-2-yl]ethyl]benzoic acid The title A anti isomer (0.82 mmol) is dissolved in THF (40 ml) and water (7.8 ml) in an argon atmosphere and treated with a 1N LiOH solution (8.2 ml). The mixture is stirred at room temperature 6 hours and then acidified by adding 1N HCl (9 ml) to bring the pH to ~3. The solution is poured into saturated NaCl solution (300 ml) and the product is extracted into ethyl acetate (4 × 100 ml). The combined EtOAc extracts are washed with saturated NaCl solution (4 × 100 ml), dried over MgSO₄, filtered and taken to dryness in vacuo leaving 281 mg (86%) of oil which starts to crystallize on standing. This is triturated with 4% MeOH in EtOAc. The white solid is harvested by filtration, washed with ethyl acetate and ether, then dried in vacuo to give the title product.

EXAMPLE 45

[1β,2α,3α,4β]-4-[2-[3-[[[(Phenylamino)carbonyl]-methylhydrazono]methyl]-7-oxabicyclo[2.2.1]hept-2-yl]ethyl]benzoic acid

A.

[1β,2α,3α,4β]-4-[2-[3-[[[(Phenylamino)carbonyl]methylhydrazono]methyl]-7-oxabicyclo[2.2.1]hept-2-yl]ethyl]benzoic acid, methyl ester

[1β,2α,3α,3β]-4-[2-[3-Formyl-7-oxabicyclo[2.2.1]hept-2-yl]ethyl]benzoic acid, methyl ester, prepared as described in Example 2 (2 mmol) and 2-methyl-4-phenylsemicarbazide (363 mg, 2.2 mmol) are dissolved in EtOH (10 ml). The reaction is stirred for 24 hours at room temperature, and concentrated in vacuo to give an oil (910 mg), which is purified by SiO₂ column (silica 60, 30 g) eluted with Et₂O/pet. ether (3.5/1.5) to give semicarbazone A in the form of a colorless oil.

B.

[1β,2α,3α,4β]-4-[2-[3-[[[(Phenylamino)carbonyl]methylhydrazono]methyl]-7-oxabicyclo[2.2.1]hept-2-yl]ethyl]benzoic acid Title A semicarbazone (0.634 mmol) is dissolved in THF (31.7 ml) and H₂O (6.3 ml) at room temperature. 1N LiOH (6.3 ml) is added. After 5 hours stirring at room temperature, the reaction is quenched by an addition of 1N HCl (6.3 ml) and poured into brine (50 ml). The products are extracted with EtOAc (80 ml×3). The combined EtOAc layers are washed with brine and dried over MgSO₄. Filtration and evaporation of solvent give an oil (225 mg) which is purified by silica gel column (silicar CC-7) to yield the title product in the form of a colorless oil.

EXAMPLE 46

[1β,2α,3α,4β]-4-[2-[3-[[(3-Pyridinylcarbonyl)methylhydrazono]methyl]-7-oxabicyclo[2.2.1]hept-2-yl]ethyl]benzoic acid

A.

[1β,2α,3α,4β]-4-[2-[3-[[(Pyridinylcarbonyl)methylhydrazono]methyl]-7-oxabicyclo[2.2.1]hept-2-yl]ethyl]benzoic acid, methyl ester

[1β,2α,3α,4β]-4-[2-[3-Formyl-7-oxabicyclo[2.2.1]hept-2-yl]ethyl]benzoic acid, methyl ester (2.0 mmol) is dissolved in ethanol (10 ml) in an argon atmosphere. 1-Methyl-1-nicotinoyl hydrazine (332 mg, 2.2 mmol) is added and the mixture is stirred at room temperature. At the end of 3 hours, more of the hydrazide (60 mg, 0.4 mmol) is added and stirring is continued for an additional 1.5 hours. The solvent is removed in vacuo and the residue is chromatographed on silica gel 60 (50 g) eluting with 2% MeOH in EtOAc to give the title A compound.

B.

[1β,2α,3α,4β]-4-[2-[3-[[(3-Pyridinylcarbonyl)methylhydrazono]methyl]-7-oxabicyclo[2.2.1]hept-2-yl]ethyl]benzoic acid The title A methyl ester (0.98 mmol) is dissolved in THF (50 ml) and water (8.5 ml). 1N LiOH solution (9.8 ml) is added and the mixture is stirred at room temperature 4 hours. 1N HCl solution (9.8 ml) is then added (pH~5) and the mixture is poured into 300 ml saturated NaCl solution. The product is extracted into ethyl acetate (4×100 ml). The ethyl acetate extracts are washed with saturated NaCl solution (4×100 ml), dried (mgSO₄) and freed of solvent in vacuo leaving the title product.

EXAMPLE 47

[1β,2α,3β,4β]-4-[2-[3-[[(3-Pyridinylcarbonyl)methylhydrazono]methyl]-7-oxabicyclo[2.2.1]hept-2-yl]ethyl]benzoic acid Following the procedure of Example 46 except substituting for the aldehyde employed in Example 46 Part A, [1β,2α,3β,4β]-4-[2-[3-formyl-7-oxabicyclo[2.2.1]hept-2-yl]ethyl]benzoic acid, methyl ester, the title compound is obtained.

EXAMPLE 48

[1β,2α,3β,4β]-4-[2-[3-[[(Cyclohexylcarbonyl)methylhydrazono]methyl]-7-oxabicyclo[2.2.1]hept-2-yl]ethyl]benzoic acid Following the procedure of Example 42 except substituting 1-methyl-1-cyclohexylcarbonyl hydrazine for methyl benzoyl hydrazine, the title compound is obtained.

EXAMPLE 49

[1β,2α,3α,4β]-4-[2-[3-[[(Cyclohexylcarbonyl)methylhydrazono]methyl]-7-oxabicyclo[2.2.1]hept-2-yl]ethyl]benzoic acid Following the procedure of Example 43 except substituting 1-methyl-1-cyclohexylcarbonyl hydrazine for 1-methyl-1-benzoyl hydrazine, the title compound is obtained.

EXAMPLE 50

[1β,2α,3α,4β]-4-[2-[3-[[(2-Oxo-1-piperidinyl)imino]methyl]-7-oxabicyclo[2.2.1]hept-2-yl]ethyl]benzoic acid

A. 1-Amino-2-piperidone

Methyl δ-bromovalerate (9.75 g) in dry MeOH (50 ml) was added dropwise to a magnetically stirred solution of hydrazine hydrate (2.5 g) in dry MeOH (125 ml) over 40 minutes at room temperature. After 22 hours stirring at room temperature, an additional hydrazine hydrate (2.5 g) was added. Stirring was continued for 6 hours at room temperature. Then, sodium methoxide (sodium, 1.15 g) in dry MeOH (25 ml) was added dropwise to the reaction at room temperature, which was stirred overnight. Solvent was removed in vacuo and the residual sludge was distilled to give a desired compound, a colorless liquid (3.4 g, b.p. 84° C./0.4 mmHg).

B.

[1β,2α,3α,4β]-4-[2-[3-[[(2-Oxo-1-piperidinyl)imino]methyl]-7-oxabicyclo]-ethyl]benzoic acid, methyl ester

[1β,2α,3α,4β]-4-[2-[3-Formyl-7-oxabicyclo[2.2.1]hept-2-yl]ethyl]benzoic acid, methyl ester, prepared as described in Example 2 (2 mmol), and 1-amino-2-piperidone (230 mg) in MeOH (10 ml) and stirred at room temperature overnight. Solvent is removed in vacuo and the residual oil is purified by SiO₂ column (silica 60, 30 g) eluted with pet. ether/ether (½) to give the desired title hydrazone (615.3 mg).

C.

[1β,2α,3α,4β]-4-[2-[3-[[(2-Oxo-1-piperidinyl)imino]methyl]-7-oxabicyclo[2.2.1]hept-2-yl]ethyl]benzoic acid 1N LiOH (6.7 ml) is added to title B ester (0.67 mmol) dissolved in THF (34 ml) and H₂O (6.7 ml) at room temperature. The reaction is stirred for 6 hours at room temperature. 1N HCl (6.7 ml) is added to the reaction, which is poured into brine (~50 ml). The products are extracted with EtOAc (100 ml×3). The combined EtOAc layers are washed with brine (50 ml×2), and dried over MgSO$_4$. Filtration and evaporation of solvents afford oil, which is purified by silica gel column (silicar CC-7, 25 g) eluted with CH$_2$Cl$_2$/MeOH (9/1) to give the title product.

EXAMPLE 51

[1β,2α,3β,4β]-4-[2-[3-[[(2-Oxo-1-piperidinyl)imino]methyl]-7-oxabicyclo[2.2.1]hept-2-yl]-ethyl]benzoic acid Following the procedure of Example 36, except substituting 1-amino-2-piperidone (prepared by reaction of hydrazine hydrate and methyl 5-bromopentanoate) for the Example 36A hydrazine, the title compound is obtained.

EXAMPLE 52

[1β,2α,3α,4β]-4-[2-[3-[[(Phenoxycarbonyl)methylhydrazono]methyl]-7-oxabicyclo[2.2.1]hept-2-yl]ethyl]benzoic acid Following the procedure of Example 37, except employing [1β,2α,3α,4β]-4-[2-[3-formyl-7-oxabicyclo[2.2.1]hept-2-yl]ethyl]benzoic acid and substituting the 1-methyl-1-phenoxycarbonyl hydrazine for the n-propyl hydrazonocarboxylate, the title compound is obtained.

EXAMPLE 53

[1β,2α,3β,4β]-4-[2-[3-[[(Phenoxycarbonyl)methylhydrazono]methyl]-7-oxabicyclo[2.2.1]hept-2-yl]ethyl]benzoic acid Following the procedure of Example 52 except substituting [1β,2α,3β,4β]-4-[2-[3-formyl-7-oxabicyclo[2.2.1]hept-2-yl]ethyl]benzoic acid, methyl ester for the methyl ester employed in Example 52, the title compound is obtained.

EXAMPLE 54

[1β,2α,3β,4β]-4-[2-[3-[[(1-Oxohexyl)methyl]hydrazono]methyl]-7-oxabicyclo[2.2.1]hept-2-yl]ethyl]benzoic acid Following the procedure of Example 40 except substituting 1-hexanoyl-1-methyl hydrazine for 1-pentanoyl-1-methyl hydrazine, the title compound is obtained.

EXAMPLE 55

[1β,2α,3α,4β]-4-[2-[3-[[(1-Oxohexyl)methyl]hydrazono]methyl]-7-oxabicyclo[2.2.1]hept-2-yl]ethyl]benzoic acid Following the procedure of Example 41 except substituting 1-hexanoyl-1-methyl hydrazine for 1-pentanoyl-1-methyl hydrazine, the title compound is obtained.

EXAMPLE 56

[1β,2α,3α,4β]-4-[2-[3-[[[(n-Butylamino)carbonyl]ethylhydrazono]methyl-7-oxabicyclo[2.2.1]hept-2-yl]ethyl]benzoic acid Following the procedure of Example 45 except substituting 2-ethyl 4-butylsemicarbazide for 2-methyl 4-phenylsemicarbazide, the title compound is obtained.

EXAMPLE 57

[1β,2β,3α,4β]-4-[2-[3-[[(1-Oxopentyl)methylhydrazino]methyl]-7-oxabicyclo[2.2.1]-2-yl]ethyl]benzoic acid Following the procedure of Example 36 except substituting [1β,2β,3α,4β]-4-[2-[3-formyl-7-oxabicyclo[2.2.1]hept-2-yl]ethyl]benzoic acid, methyl ester (prepared as described in Example 1 for the aldehyde employed in Example 36, the title product is obtained.

EXAMPLE 58

[1β,2β,3α,4β]-4-[2-[3-[[(Propoxycarbonyl)methylhydrazono]methyl]-7-oxabicyclo[2.2.1]hept-2-yl]ethyl]benzoic acid Following the procedure of Example 57 except substituting 1-methyl-1-propoxycarbonyl hydrazine for the Example 36A carbazate, the title compound is obtained.

EXAMPLE 59

[1β,2β,3α,4β]-4-[2-[3-[(Ethylbenzoylhydrazono)methyl]-7-oxabicyclo[2.2.1]hept-2-yl]ethyl]benzoic acid Following the procedure of Example 57 except substituting 1-methyl-1-benzoyl hydrazine for the Example 40 hydrazide, the title compound is obtained.

EXAMPLE 60

[1β,2β,3α,4β]-4-[2-[3-[[[(Phenylamino)carbonyl]methylhydrazono]methyl]-7-oxabicyclo[2.2.1]hept-2-yl]ethyl]benzoic acid Following the procedure of Example 57 except substituting 2-methyl-4-phenyl semicarbazide for the Example 36A carbazate, the title compound is produced.

EXAMPLE 61

[1β,2β,3α,4β]-4-[2-[3-[[(3-Pyridinylcarbonyl)methylhydrazono]methyl]-7-oxabicyclo[2.2.1]hept-2-yl]ethyl]benzoic acid Following the procedure of Example 57 except substituting 1-methyl-1-nicotinoyl hydrizine for the Example 36A carbazate, the title compound is produced.

EXAMPLE 62

[1β,2β,3α,4β]-4-[2-[3-[[(Cyclohexylcarbonyl)methylhydrazono]methyl]-7-oxabicyclo[2.2.1]hept-2-yl]ethyl]benzoic acid Following the procedure of Example 57 except substituting 1-methyl-1-cyclohexylcarbonyl hydrazine for the Example 36A carbazate, the title compound is obtained.

EXAMPLE 63

[1β,2β,3α,4β]-4-[2-[3-[[(n-Butylamino)carbonyl]ethylhydrazono]methyl]-7-oxabicyclo[2.2.1]hept-2-yl]ethyl]benzoic acid Following the procedure of Example 57 except substituting 2-ethyl-4-n-butylsemicarbazide for 2-methyl-4-phenyl-semicarbazide, the title compound is obtained.

EXAMPLE 64

[1β,2β,3α,4β]-4-[2-[3-[[(1-Oxopentyl)methylhydrazono]methyl]-7-oxabicyclo[2.2.1]hept-2-yl]ethyl]benzoic acid Following the procedure of Example 57 except substituting 1-methyl-1-pentanoyl hydrazine for the Example 36A carbazate the title compound is obtained.

EXAMPLE 65

[1β,2β,3α,4β]-4-[2-[3-[[1-(2-Oxo-1-piperidinyl)imino]methyl]-7-oxabicyclo[2.2.1]hept-2-yl]ethyl]benzoic acid Following the procedure of Example 57 except substituting 1-amino-2-piperidone for the Example 36A carbazate, the title compound is obtained.

EXAMPLE 66

[1β,2β,3α,4β]-4-[2-[3-[[(Phenoxycarbonyl)methylhydrazono]methyl]-7-oxabicyclo[2.2.1]hept-2-yl]ethyl]benzoic acid Following the procedure of Example 57 except substituting 1-methyl-1-phenoxycarbonyl hydrazine for the Example 36A carbazate, and substituting [1β,2β,3α,4β]-4-[2-[3-formyl-7-oxabicyclo[2.2.1]hept-2-yl]ethyl]benzoic acid for the corresponding methyl ester, the title compound is obtained.

EXAMPLE 67

[1β,2α,3α,4β]-4-[2-[3-[[(Pentyloxy)imino]methyl]-7-oxabicyclo[2.2.1]hept-2-yl]ethyl]benzoic acid

A.

[1β,2α,3α,4β]-4-[2-[3-[[(Pentyloxy)imino]methyl]-7-oxabicyclo[2.2.1]hept-2-yl]ethyl]benzoic acid, methyl ester O-pentylhydroxyamine hydrochloride (306.9 mg, 2.2 mmol) is added to a suspension of NaOAc (196.8 mg, 2.4 mmol) in dry EtOH (10 ml). NaCl is immediately precipitated out. Then, [1β,2α,3α,4β]-4-[2-[3-formyl-7-oxabicyclo[2.2.1]hept-2-yl]ethyl]benzoic acid, methyl ester (2.0 mmol) in dry EtOH (1 ml) is added at room temperature. After 1 hour stirring, the reaction mixture is poured into Et₂O, which is washed with 1N HCl (20 ml×2), saturated NaHCO₃ (20 ml×2), brine (20 ml×2) and dried over MgSO₄. Filtration and evaporation of solvents in vacuo give an oil. The oil is purified by column chromatography (silica 60, 30 g) eluted with ether/pet. ether (1:2) to give the title compound.

B.

[1β,2α,3α,4β]-4-[2-[3-[[(Pentyloxy)imino]methyl]-7-oxabicyclo[2.2.1]hept-2-yl]ethyl]benzoic acid Fast moving isomer from Part A (0.794 mmol) is dissolved in THF (40 ml) and H₂O (8 ml) at 0° C. under an argon atmosphere. 1N LiOH (8 ml) is added and the reaction is allowed to warm to room temperature. Stirring is continued for 6¾ hours. Then 10% oxalic acid is added to adjust to pH 3 and the reaction is poured into H₂O (200 ml). The products are extracted with ether (3×100~150 ml). Combined ether layers are further washed with H₂O (100 ml×3), brine (50 ml), and dried over MgSO₄. Filtration and evaporation of solvent in vacuo give the title product.

EXAMPLE 68

[1β,2α,3β,4β]-4-[2-[3-[[(Pentyloxy)imino]methyl]-7-oxabicyclo[2.2.1]hept-2-yl]ethyl]benzoic acid

A.

[1β,2α,3β,4β]-4-[2-[3-[[(Pentyloxy)imino]methyl]-7-oxabicyclo[2.2.1]hept-2-yl]ethyl]benzoic acid, methyl ester O-Pentylhydroxyamine hydrochloride (2.2 mmol) is added to a suspension of sodium acetate (196.8 mg, 2.4 mmol) in 10 ml dist. ethanol. A solution of [1β,2α,3β,4β]-4-[2-[3-formyl-7-oxabicyclo[2.2.1]hept-2-yl]ethyl]benzoic acid, methyl ester (2 mmol) in 1 ml ethanol is then added and the mixture is stirred at room temperature for 1 hour. The reaction mixture is poured into 100 ml ether and washed with 1N HCl solution (2×20 ml), saturated NaHCO₃ solution (2×20 ml) and saturated NaCl solution (2×20 ml). The solution is dried over MgSO₄, filtered and freed of solvent in vacuo leaving an oil. This is chromatographed on 30 g silica gel 60 eluting with ether-petroleum ether 1:2 to give clean title methyl ester.

B.

[1β,2α,3β,4β]-4-[2-[3-[[(Pentyloxy)imino]methyl]-7-oxabicyclo[2.2.1]hept-2-yl]ethyl]benzoic acid The methyl ester prepared in Part A (0.62 mmol) is dissolved in 30 ml THF and 5.8 mg H₂O in an argon atmosphere. 1N LiOH (6.2 ml) is added and the mixture is stirred at room temperature 6½ hours. Oxalic acid (saturated aqueous solution) is then added to adjust to pH 3 and the mixture is poured into 250 ml H₂O. The product is extracted into ether (3×100 ml). The combined ether extracts are washed with water (3×100 ml) and saturated NaCl solution (1×100 ml), dried over MgSO₄, filtered and taken to dryness in vacuo to give the title compound.

EXAMPLE 69

[1β,2α,3α,4β]-4-[2-[3-[[(Phenylmethoxy)imino]methyl]-7-oxabicyclo[2.2.1]hept-2-yl]ethyl]benzoic acid

A.

[1β,2α,3α,4β]-4-[2-[3-[[(Phenylmethoxy)imino]methyl]-7-oxabicyclo[2.2.1]hept-2-yl]ethyl]benzoic acid, methyl ester NaOAc (164 mg, 2 mmol) is added to a magnetically stirred suspension of O-benzylhydroxylamino hydrochloride (320 mg, 2 mmol) in EtOH (8 ml) at room temperature. Then [1β,2α,3α,4β]-4-[2-[3-formyl-7-oxabicyclo[2.2.1]hept-2-yl]ethyl]-benzoic acid, methyl ester (2 mmol) in EtOH (2 ml) is added and stirred for 1 hour at room temperature. The reaction is poured into Et₂O (100 ml), which is washed with 1N HCl (20 ml×2), saturated NaHCO₃ (20 ml×2), brine (20 ml×2), and dried over MgSO₄. Filtration and evaporation of solvents give the title compound.

B.

[1β,2α,3α,4β]-4-[2-[3-[[(Phenylmethoxy)imino]methyl]-7-oxabicyclo[2.2.1]hept-2-yl]ethyl]benzoic acid 1N LiOH (7.2 ml) is added to a magnetically stirred solution of the title A oxime (268.6 mg, 0.723 mmol) dissolved in THF (36 ml) and H₂O (7 ml) at 0° C. under argon. The reaction is warmed to room temperature, and stirring is continued for 6 hours. 10% Oxalic acid is added to quench the reaction and to adjust to pH 3. The reaction is poured into H₂O (200 ml), which is extracted with Et₂O (100 ml×4). The combined ether layers are washed with H₂O (50 ml×3), brine (50 ml) and dried over MgSO₄. Filtration and evaporation of solvent in vacuo give the title compound.

EXAMPLE 70

[1β,2α,3β,4β]-4-[2-[3-[[(Phenylmethoxy)imino]methyl]-7-oxabicyclo[2.2.1]hept-2-yl]ethyl]benzoic acid

A.

[1β,2α,3β,4β]-4-[2-[3-[[(Phenylmethoxy)imino]methyl]-7-oxabicyclo[2.2.1]hept-2-yl]ethyl]benzoic acid, methyl ester O-Benzylhydroxylamine hydrochloride (351.2 mg, 2.2 mmol) is added to a stirred suspension of sodium acetate (196.8 mg, 2.4 mmol) in 10 ml distilled ethanol in an argon atmosphere. A solution of [1β,2α,3β,4β]-4-[2-[3-formyl-7-oxabicyclo[2.2.1]hept-2-yl]ethyl]benzoic acid, methyl ester prepared as described in Example 36 (2 mmol) in 1 ml ethanol is added and the mixture is stirred at room temperature 90 minutes. The mixture is poured into 100 ml ether and the ether solution is washed with 1N HCl solution (2×20 ml), saturated NaHCO₃ solution (2×20 ml) and saturated NaCl solution (2×20 ml). The solution is dried over MgSO₄, filtered and taken to dryness in vacuo leaving 730 mg (98%) of oil. This is chromatographed on 35 g silica gel 60, eluting with ether-petroleum ether (1:2) to give clean (by TLC) title compound as a colorless oil.

B.

[1β,2α,3β,4β]-4-[2-[3-[[(Phenylmethoxy)imino]methyl]-7-oxabicyclo[2.2.1]hept-2-yl]ethyl]benzoic acid The Part A methyl ester (0.635 mmol) is dissolved in 30 ml THF and 5.8 ml H₂O in an argon atmosphere and treated with 6.35 ml 1N LiOH. The mixture is stirred at room temperature 6 hours. The pH is then adjusted to ~3 by adding a saturated oxalic acid solution and the clear solution is poured into 250 ml water. The product is extracted into ether (3×100 ml). The combined ether extracts are washed with water (3×100 ml) and saturated NaCl solution (1×100 ml), dried over MgSO₄, filtered and freed of solvent in vacuo leaving title compound.

EXAMPLE 71

[1β,2α,3α,4β]-4-[2-[3-[[(Butyloxy)imino]methyl]-7-oxabicyclo[2.2.1]hept-2-yl]ethyl]benzoic acid Following the procedure of Example 67 except substituting 1-bromobutane for 1-bromopentane, the title compound is produced.

EXAMPLE 72

[1β,2α,3β,4β]-4-[2-[3-[[(Butyloxy)imino]methyl]-7-oxabicyclo[2.2.1]hept-2-yl]ethyl]benzoic acid Following the procedure of Example 68 except substituting O-butylhydroxyamine hydrochloride for O-pentylhydroxyamine hydrochloride, the title compound is obtained.

EXAMPLE 73

[1β,2α,3α,4β]-4-[2-[3-[[(Hexyloxy)imino]methyl]-7-oxabicyclo[2.2.1]hept-2-yl]ethyl]benzoic acid Following the procedure of Example 67 except substituting 1-bromohexane for 1-bromopentane, the title compound is produced.

EXAMPLE 74

[1β,2α,3β,4β]-4-[2-[3-[[(Hexyloxy)imino]methyl]-7-oxabicyclo[2.2.1]hept-2-yl]ethyl]benzoic acid Following the procedure of Example 68 except substituting O-hexylhydroxyamine hydrochloride for O-pentylhydroxyamine hydrochloride, the title compound is produced.

EXAMPLE 75

[1β,2α,3α,4β]-4-[2-[3-[[(Cyclohexyloxy)imino]methyl]-7-oxabicyclo[2.2.1]hept-2-yl]ethyl]benzoic acid Following the procedure of Example 67 except substituting bromocyclohexane for 1-bromopentane, the title compound is produced.

EXAMPLE 76

[1β,2α,3β,4β]-4-[2-[3-[[(Cyclohexyloxy)imino]methyl]-7-oxabicyclo[2.2.1]hept-2-yl]ethyl]benzoic acid Following the procedure of Example 68 except substituting O-cyclohexylhydroxyamine hydrochloride for O-pentylhydroxyamine hydrochloride, the title compound is produced.

EXAMPLE 77

[1β,2α,3α,4β]-4-[2-[3-[[(Phenyloxy)imino]methyl]-7-oxabicyclo[2.2.1]hept-2-yl]ethyl]benzoic acid Following the procedure of Example 67 except substituting O-phenylhydroxylamine for O-pentylhydroxylamine hydrochloride, the title compound is produced.

EXAMPLE 78

[1β,2α,3β,4β]-4-[2-[3-[[(Phenyloxy)imino]methyl]-7-oxabicyclo[2.2.1]hept-2-yl]ethyl]benzoic acid Following the procedure of Example 68 except substituting O-phenylhydroxyamine hydrochloride for O-pentylhydroxyamine hydrochloride, the title compound is produced.

EXAMPLE 79

[1β,2α,3α,4β]-4-[2-[3-[[(Acetyloxy)imino]methyl]-7-oxabicyclo[2.2.1]hept-2-yl]ethyl]benzoic acid Following the procedure of Example 67 except substituting O-acetyloxyhydroxyl hydrochloride for O-pentylhydroxyamine hydrochloride, the title compound is obtained.

EXAMPLE 80

[1β,2α,3α,4β]-4-[2-[3-[[(Pentyloxy)imino]methyl]-7-oxabicyclo[2.2.1]hept-2-yl]ethyl]benzoic acid Following the procedure of Example 67 except substituting [1β,2α,3α,4β]-4-[2-[3-formyl-7-oxabicyclo[2.2.1]hept-2-yl]ethyl]benzoic acid, methyl ester for the aldehyde used in Example 67, the title product is obtained.

EXAMPLE 81

[1β,2α,3β,4β]-4-[2-[3-[[(Pentyloxy)imino]methyl]-7-oxabicyclo[2.2.1]hept-2-yl]ethyl]benzoic acid Following the procedure of Example 76 except substituting [1β,2α,3β,4β]-4-[2-[3-formyl-7-oxabicyclo[2.2.1]hept-2-yl]ethyl]benzoic acid, methyl ester for the aldehyde used in Example 67, the title product is obtained.

EXAMPLE 82

[1β,2α,3β,4β]-4-[2-[3-[(Hexylamino)methyl]-7-oxabicyclo[2.2.1]hept-2-yl]ethyl]benzoic acid

A.
[1β,2α,3β,4β]-7-[3-[(Hexylamino)methyl]-7-oxabicyclo[2.2.1]hept-2-yl]-5-heptenoic acid, methyl ester To 0.50 mmole (1 eq) of [1β,2α,3β,4β]-4-[2-[3-formyl-7-oxabicyclo[2.2.1]hept-2-yl]ethyl]benzoic acid in 3 ml of anhydrous methanol under an argon atmosphere at 25° is added 101.1 mg (1.0 mmole, 2 eq) of hexylamine and ca. 300 mg of activated crushed 3 Å molecular sieves. The reaction is stirred for 96 hours, diluted with 2 ml of anhydrous methanol, cooled to 0° and an excess of sodium borohydride is added. This reaction mixture is stirred for 30 minutes, quenched with 1 ml of acetone, diluted with 100 ml of ether and washed successively with 50 ml of water and 50 ml of brine, and dried over anhydrous magnesium sulfate. The product is purified by flash chromatography on LP-1 silica using a 167/15/1 chloroform:methanol:formic acid solution as the eluent to provide the title compound.

B.
[1β,2α,3β,4β]-4-[2-[3-[(Hexylamino)methyl]-7-oxabicyclo[2.2.1]hept-2-yl]ethyl]benzoic acid 0.43 Mmol of the title A ester in 10 ml of a 1N sodium hydroxide solution is refluxed for 45 minutes, cooled, neutralized to ca. pH 6.5 with dilute hydrochloric acid, and extracted with two 85 ml portions of ethyl acetate to provide an oil. This material is recrystallized twice from acetonitrile to provide the title product.

EXAMPLE 83

[1β,2α,3α,4β]-4-[2-[3-[(Hexylamino)methyl]-7-oxabicyclo[2.2.1]hept-2-yl]ethyl]benzoic acid

A.
[1β,2α,3α,4β]-4-[2-[3-[(Hexylamino)methyl]-7-oxabicyclo[2.2.1]hept-2-yl]ethyl]benzoic acid, methyl ester

[1β,2α,3α,4β]-4-[2-[3-Formyl-7-oxabicyclo[2.2.1]hept-2-yl]ethyl]benzoic acid, methyl ester is treated with hexylamine as described in Example 82A to give [1β,2α,3α,4β]-4-[2-[3-[(hexylamino)methyl]-7-oxabicyclo[2.2.1]hept-2-yl]ethyl]benzoic acid, methyl ester.

B.
[1β,2α,3α,4β]-4-[2-[3-[(Hexylamino)methyl]-7-oxabicyclo[2.2.1]hept-2-yl]ethyl]benzoic acid 0.43 Mmole of the title A ester in 10 ml of a 1N sodium hydroxide solution is refluxed for 45 minutes, cooled, neutralized to ca. pH 6.5 with dilute hydrochloric acid, and extracted with two 85 ml portions of ethyl acetate to provide 85 mg of an oil. This material is recrystallized twice from acetonitrile to provide the title product.

EXAMPLE 84

(1β,2β,3α,4β)-4-[2-[3-[(Hexylamino)methyl]-7-oxabicyclo[2.2.1]hept-2-yl]ethyl]benzoic acid Following the procedure of Example 82, except substituting [1β,2β,3α,4β]-4-[2-[3-formyl-7-oxabicyclo[2.2.1]hept-2-yl]ethyl]benzoic acid, methyl ester for the aldehyde used in Example 82, the title product is obtained.

EXAMPLE 85

[1β,2α,3α,4β]-4-[2-[3-[[(Phenylmethoxy)amino]methyl]-7-oxabicyclo[2.2.1]hept-2-yl]ethyl]benzoic acid

A.
[1β,2α,3α,4β]-4-[2-[3-[[(Phenylmethoxy)imino]methyl]-7-oxabicyclo[2.2.1]hept-2-yl]ethyl]benzoic acid, methyl ester NaOAc (164 mg, 2 mmol) is added to a magnetically stirred suspension of O-benzylhydroxylamine hydrochloride (320 mg, 2 mmol) in EtOH (8 ml) at room temperature. Then, [1β,2α,3α,4β]-4-[2-[3-formyl-7-oxabicyclo[2.2.1]hept-2-yl]ethyl]benzoic acid, methyl ester (2 mmol) in EtOH (2 ml) is added and stirred for 1 hour at room temperature. The reaction is poured into Et₂O (2 ml) is added and stirred for 1 hour at room temperature. The reaction is poured into Et₂O (100 ml), which is washed with 1N HCl (20 ml×2), saturated NaHCO₃ (20 ml×2), brine (20 ml×2), and dried over MgSO₄. Filtration and evaporation of solvents give the title compound.

B.
[1β,2α,3α,4β]-4-[2-[3-[[(Phenylmethoxy)amino]methyl]-7-oxabicyclo[2.2.1]hept-2-yl]ethyl]benzoic acid, methyl ester NaBH₃CN (57 mg, 0.92 mmol) is added to a magnetically stirred solution of oxime prepared as described in Part A (0.71 mmol) in MeOH (8.5 ml), followed by addition of AcOH (1.5 ml) dropwise. After 2¼ hours stirring at room temperature, additional NaBH₃CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basicified by addition of saturated NaHCO₃. The products are extracted with Et₂O (100 ml×2). The combined ether layers are washed with brine and dried over MgSO₄. Filtration and evaporation of solvent give title compound.

C.
[1β,2α,3α,4β]-4-[2-[3-[[(Phenylmethoxy)amino]methyl]-7-oxabicyclo[2.2.1]hept-2-yl]ethyl]benzoic acid 1N LiOH (6 ml) is added to the title B ester (0.59 mmol) in THF (30 ml) and H₂O (6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na₂SO₄. Filtration and evaporation of solvent yields the title product.

EXAMPLE 86

[1β,2α,3β,4β]-4-[2-[3-[[(Phenylmethoxy)amino]methyl]-7-oxabicyclo[2.2.1]hept-2-yl]ethyl]benzoic acid

A.
[1β,2α,3β,4β]-4-[2-[3-[[(Phenylmethoxy)imino]methyl]-7-oxabicyclo[2.2.1]hept-2-yl]ethyl]benzoic acid, methyl ester O-Benzylhydroxylamine hydrochloride (351.2 mg, 2.2 mmol) is added to a stirred suspension of sodium acetate (196.8 mg, 2.4 mmol) in 10 ml distilled ethanol in an argon atmosphere. A solution of [1β,2α,3β,4β]-4-[2-[3-formyl-7-oxabicyclo[2.2.1]hept-2-yl]ethyl]benzoic acid, methyl ester (2 mmol) in 1 ml ethanol is added and the mixture is stirred at room temperature 90 minutes. The mixture is poured into 100 ml ether and the ether solution is washed with 1N HCl solution (2×20 ml), saturated NaHCO$_3$ solution (2×20 ml) and saturated NaCl solution (2×20 ml). The solution is dried over MgSO$_4$, filtered and taken to dryness in vacuo leaving an oil which is chromatographed on 35 g silica gel 60, eluting with ether-pet ether (1:2) to give the title compound.

B.
[1β,2α,3β,4β]-4-[2-[3-[[(Phenylmethoxy)amino]methyl]-7-oxabicyclo[2.2.1]hept-2-yl]ethyl]benzoic acid, methyl ester The Part A methyl ester (0.88 mmol) and sodium cyanoborohydride (83.2 mg, 1.32 mmol) are dissolved in methanol (8 ml) and glacial acetic acid (4 ml). The mixture is stirred at room temperature 3¾ hours and then acidified to pH 1 with 1N HCl solution. After stirring at room temperature 30 minutes, the mixture is basified with NaHCO$_3$. The product is extracted into ether (2×80 ml), washed with saturated NaHCO$_3$ solution and saturated NaCl solution, dried and freed of solvent in vacuo to give an oil which is chromatographed on silica gel 60 (20 g), eluting with ether-pet ether to give pure title compound.

C.
[1β,2α,3β,4β]-4-[2-[3-[[(Phenylmethoxy)amino]methyl]-7-oxabicyclo[2.2.1]hept-2-yl]ethyl]benzoic acid The title B methyl ester (0.78 mmol) is dissolved in THF (40 ml) and water (8 ml) and treated with 1N LiOH solution (7.8 ml). The mixture is stirred at room temperature 6 hours, then treated with 1N HCl (7.8 ml) and poured into saturated NaCl solution (25 ml). The product is extracted into ether (3×50 ml), dried over MgSO$_4$ and freed of solvent in vacuo and is then chromatographed on silicar CC7 (20 g) eluting with CH$_2$Cl$_2$ to give the title product.

EXAMPLE 87
[1β,2α,3β,4β]-4-[2-[3-[(Phenylmethoxy)amino]methyl]-7-oxabicyclo[2.2.1]hept-2-yl]ethyl]benzoic acid Following the procedure of Example 84 and Example 86 except substituting O-benzylhydroxylamine hydrochloride for hexylamine, the title compound is obtained.

EXAMPLE 88
[1β,2α,3β,4β]-4-[2-[3-(Heptylamino)-7-oxabicyclo[2.2.1]hept-2-yl]ethyl]benzoic acid

A.
[1β,2α,3β,4β]-4-[2-[3-Carboxyl-7-oxabicyclo[2.2.1]hept-2-yl]ethyl]benzoic acid, methyl ester To 19.9 mmole of [1β,2α,3β,4β]-4-[2-[3-formyl-7-oxabicyclo[2.2.1]hept-2-yl]ethyl]benzoic acid, methyl ester (prepared as in Example 36B) in 300 ml of dimethylformamide is added 26.2 g (69.7 mmole, 3.5 eq) of pyridinium dichromate. The reaction is stirred for 24 hours, diluted with 300 ml of water and extracted with three 200 ml portions of ether. The ethereal layer is washed with three 100 ml portions of water and dried over anhydrous magnesium sulfate. The crude product is purified by flash chromatography using LP-1 silica and a gradient of 20% ether in pentane to 40% ether in pentane to provide the title acid.

B.
[1β,2α,3β,4β]-4-[2-[3-Amino-7-oxabicyclo[2.2.1]hept-2-yl]ethyl]benzoic acid, methyl ester To 1.04 mmole of the title A acid in 3 ml of anhydrous toluene is added 169 mg (1.04 mmole, 1 eq) of carbonyldiimidazole at 25° under an argon atmosphere. The reaction is stirred for 1 hour and 230.4 mg (2.08 mmole, 2 eq) of trimethylsilylazide is added. The reaction mixture is stirred for an additional 3 hours, diluted with 25 ml of toluene and washed successfully with 10 ml of cold 5% potassium bisulfate, and 10 ml of brine and dried over anhydrous magnesium sulfate. This organic solution is filtered, concentrated in vacuo, and diluted with 15 ml of anhydrous toluene. The solution is refluxed for 1 hour at 90°.

The toluene solution is then concentrated in vacuo, placed under an argon atmosphere, diluted with a 25% solution of 0.1N HCl in THF and stirred for 18 hours. The reaction mixture is diluted with 50 ml of water and washed with 50 ml of ether. The aqueous solution is then neutralized with saturated NaHCO$_3$, extracted with two 100 ml portions of ethyl acetate, washed with brine and dried over anhydrous magnesium sulfate to provide the title amine.

C.
[1β,2α,3β,4β]-4-[2-[3-(Heptylamino)-7-oxabicyclo[2.2.1]hept-2-yl]ethyl]benzoic acid To 0.51 mmole of the title B amine in 3 ml of anhydrous methanol under an argon atmosphere at 25° is added 87.3 mg (0.76 mmole, 1.5 eq) of heptanal and ca. 300 mg of activated crushed 3 Å molecular sieves. This solution is stirred for 55 hours, diluted with 4 ml of anhydrous methanol, cooled to 0°, and an excess of sodium borohydride is added. This reaction is stirred for 30 minutes, quenched with 1 ml of acetone, diluted with 100 ml of ether and washed successively with 50 ml of water, and 50 ml of brine, and dried over anhydrous magnesium sulfate. This material is purified by preparative TLC on a 2 mm 20×20 Merck silica gel-60 F254 plate using 35/3.5/1-chloroform:methanol:88% formic acid as the eluent.

D.
[1β,2α,3β,4β]-4-[2-[3-(Heptylamino)-7-oxabicyclo[2.2.1]hept-2-yl]ethyl]benzoic acid 0.31 Mmole of the title C ester is diluted with 10 ml of 1N sodium hydroxide solution and refluxed at 95° for 45 minutes under an argon atmosphere. This solution is cooled, diluted with 10 ml of water and washed with 20 ml of ether. The aqueous layer is acidified to ca. pH 6.5 with dilute hydrochloric acid, extracted with two 100 ml portions of ethyl acetate and dried over anhydrous magnesium sulfate. This material is purified by flash chromatography on an LP-1 silica column using a 10% methanol in methylene chloride solution as the eluent, concentrated in vacuo, diluted with distilled methylene chloride and filtered through a millipore membrane to provide the title product.

EXAMPLE 89

[1β,2α,3α,4β]-4-[2-[3-(Heptylamino)-7-oxabicyclo[2.2.1]hept-2-yl]ethyl]benzoic acid

A.
[1β,2α,3α,4β]-4-[2-[3-Carboxyl-7-oxabicyclo[2.2.1]hept-2-yl]ethyl]benzoic acid, methyl ester To 19.9 Mmole of [1β,2α,3α,4β]-4-[2-[3-(hydroxymethyl)-7-oxabicyclo[2.2.1]hept-2-yl]ethyl]benzoic acid, methyl ester (prepared as in Example 2I) in 300 ml of dimethylformamide is added 26.2 g (69.7 mmole, 3.5 eq) of pyridinium dichromate. The reaction is stirred for 24 hours, diluted with 300 ml of water and extracted with three 100 ml portions of ether. The ethereal layer is washed with three 100 ml portions of water and dried over anhydrous magnesium sulfate. The crude product is purified by flash chromatography using LP-1 silica and a gradient of 20% ether in pentane to 40% ether in pentane to provide the title acid.

B.
[1β,2α,3α,4β]-4-[2-[3-Amino-7-oxabicyclo[2.2.1]hept-2-yl]ethyl]benzoic acid, methyl ester To 1.04 mmole of the title A acid in 3 ml of anhydrous toluene is added 169 mg (1.04 mmole, 1 eq) of carbonyldiimidazole at 25° under an argon atmosphere. The reaction is stirred for 1 hour and 230.4 mg (2.08 mmole, 2 eq) of trimethylsilylazide is added. The reaction mixture is stirred for an additional 3 hours, diluted with 25 ml of toluene and washed successively with 10 ml of cold 5% potassium bisulfate, and 10 ml of brine and dried over anhydrous magnesium sulfate. This organic solution is filtered, concentrated in vacuo and diluted with 15 ml of anhydrous toluene. The solution is refluxed for 1 hour at 90°.

The toluene solution is then concentrated in vacuo, placed under an argon atmosphere, diluted with a 25% solution of 0.1N HCl in THF and stirred for 18 hours. The reaction mixture is diluted with 50 ml of water and washed with 50 ml of ether. The aqueous solution is then neutralized with saturated NaHCO₃, extracted with two 100 ml portions of ethyl acetate, washed with brine and dried over anhydrous magnesium sulfate to provide the title amine.

C.
[1β,2α,3α,4β]-4-[2-[3-(Heptylamino)-7-oxabicyclo[2.2.1]hept-2-yl]ethyl]benzoic acid, methyl ester To 0.51 mmole of the title B amine in 3 ml of anhydrous methanol under an argon atmosphere at 25° is added 87.3 mg (0.76 mmole, 1.5 eq) of heptanal and ca. 300 mg of activated crushed 3 Å molecular sieves. This solution is stirred for 55 hours, diluted with 4 ml of anhydrous methanol, cooled to 0°, and an excess of sodium borohydride is added. This reaction is stirred for 30 minutes, quenched with 1 ml of acetone, diluted with 100 ml of ether and washed successively with 50 ml of water, and 50 ml of brine, and dried over anhydrous magnesium sulfate. This material is purified by preparative TLC on a 2 mm 20×20 Merck silica gel-60 F254 plate using 35/3.5/1-chloroform:methanol:88% formic acid as the eluent.

D.
[1β,2α,3α,4β]-4-[2-[3-(Heptylamino)-7-oxabicyclo[2.2.1]hept-2-yl]ethyl]benzoic acid 0.31 Mmole of the title C ester is diluted with 10 ml of a 1N sodium hydroxide solution and refluxed at 95° for 45 minutes under an argon atmosphere. This solution is cooled, diluted with 10 ml of water and washed with 20 ml of ether. The aqueous layer is acidified to ca. pH 6.5 with dilute hydrochloric acid, extracted with two 100 ml portions of ethyl acetate and dried over anhydrous magnesium sulfate. This material is purified by flash chromatography on an LP-1 silica column using a 10% methanol in methylene chloride solution as the eluent, concentrated in vacuo, diluted with distilled methylene chloride and filtered through a millipore membrane to provide the title product.

EXAMPLE 90

[1β,2α,3β,4β]-4-[2-[3-(Pentylamino)methyl]-7-oxabicyclo[2.2.1]hept-2-yl]ethyl]benzoic acid Following the procedure of Example 82 except substituting pentylamine for hexylamine the title compound is obtained.

EXAMPLE 91

[1β,2α,3α,4β]-4-[2-[3-(Pentylamino)methyl]-7-oxabicyclo[2.2.1]hept-2-yl]ethyl]benzoic acid Following the procedure of Example 83 except substituting pentylamine for hexylamine, the title compound is obtained.

EXAMPLE 92

[1β,2α,3β,4β]-4-[2-[3-(Pentylamino)methyl]-7-oxabicyclo[2.2.1]hept-2-yl]ethyl]benzoic acid Following the procedure of Example 84 except substituting pentylamine for hexylamine, the title compound is obtained.

EXAMPLE 93

[1β,2α,3β,4β]-4-[2-[3-(Heptylamino)methyl]-7-oxabicyclo[2.2.1]hept-2-yl]ethyl]benzoic acid Following the procedure of Example 82 except substituting heptylamine for hexylamine, the title compound is obtained.

EXAMPLE 94

[1β,2α,3α,4β]-4-[2-[3-(Heptylamino)methyl]-7-oxabicyclo[2.2.1]hept-2-yl]ethyl]benzoic acid Following the procedure of Example 83 except substituting heptylamine for hexylamine, the title compound is obtained.

EXAMPLE 95

[1β,2α,3β,4β]-4-[2-[3-(Heptylamino)methyl]-7-oxabicyclo[2.2.1]hept-2-yl]ethyl]benzoic acid Following the procedure of Example 84 except substituting heptylamine for hexylamine, the title compound is obtained.

EXAMPLE 96

[1β,2α,3β,4β]-4-[2-[3-(Pentylamino)-7-oxabicyclo[2.2.1]hept-2-yl]ethyl]benzoic acid Following the procedure of Example 88 except substituting pentanal for heptanal, the title compound is obtained.

EXAMPLE 97

[1β,2α,3α,4β]-4-[2-[3-(Pentylamino)-7-oxabicyclo[2.2.1]hept-2-yl]ethyl]benzoic acid Following the procedure of Example 89 except substituting pentanal for haptanal, the title compound is obtained.

EXAMPLE 98

[1β,2α,3β,4β]-4-[2-[3-(Hexylamino)-7-oxabicyclo[2.2.1]hept-2-yl]ethyl]benzoic acid Following the procedure of Example 88 except substituting hexanal for heptanal, the title compound is obtained.

EXAMPLE 99

[1β,2α,3α,4β]-4-[2-[3-(Hexylamino)-7-oxabicyclo[2.2.1]hept-2-yl]ethyl]benzoic acid Following the procedure of Example 89 except substituting hexanal for heptanal, the title compound is obtained.

EXAMPLE 100

[1β,2β,3α,4β]-4-[2-[3-[[2-(1-Oxopentyl)hydrazino]methyl]-7-oxabicyclo[2.2.1]hept-2-yl]ethyl]benzoic acid

A. Pentanoyl hydrazine

Methyl valerate (11.62 g, 0.1 mol) was added to hydrazine hydrate (5.0 g, 0.1 mol). The reaction was heated at reflux under vigorous stirring for 24 hours. Low boiling materials (MeOH and H₂O) were removed in vacuo and the residue was crystallized from isopropyl ether to give the title compound in the form of needle crystals (10.5 g, 0.0905 mol, 91%, m.p. 59°–61° C.).

B.

[1β,2β,3α,4β]-4-[2-[3-[[(1-Oxopentyl)hydrazono]methyl]-7-oxabicyclo[2.2.1]hept-2-yl]ethyl]benzoic acid, methyl ester

[1β,2β,3α,4β]-4-[2-[3-Formyl-7-oxabicyclo[2.2.1]hept-2yl]ethyl]benzoic acid, methyl ester (2 mmol) and the title A hydrazide (255.2 mg, 2.2 mmol) are stirred in EtOH (10 ml) at room temperature for 1 hours. The reaction is poured into Et₂O (150 ml), which is washed with 1N HCl (30 ml×2), saturate NaHCO₃ (30 ml×2), brine (30 ml×2), and dried over MgSO₄. Filtration and evaporation of solvent give a viscous oil which is purified by silica gel column eluted with Et₂O/EtOAc—4/1 to give a colorless oil. Crystallization from diisopropyl ether/pet ether affords the title product.

C.

[1β,2β,3α,4β]-4-[2-[3-[[2-(1-Oxopentyl)hydrazino]methyl]-7-oxabicyclo[2.2.1]hept-2-yl]ethyl]benzoic acid, methyl ester NaBH₃CN (57 mg, 0.92 mmol) is added to a magnetically stirred solution of the title B compound (0.71 mmol) in MeOH (8.5 ml), followed by addition of AcOH (1.5 ml) dropwise. After 2¼ hours stirring at room temperature, additional NaBH₃CN (40 mg, 0.64 mmol) and AcOH (1 ml) is added. Stirring is continued at room temperature for 1 hour. Then, the reaction is quenched by addition of 2N HCl to pH 1 and stirred for 30 minutes. The reaction is basified by addition of saturated NaHCO₃. The products are extracted with Et₂O (100 ml×2). The combined ethers layers are washed with brine and dried over MgSO₄. Filtration and evaporation of solvent gives the title compound.

D.

(1β,2β,3α,4β)-4-[2-[3-[[2-(1-Oxopentyl)hydrazino]methyl]-7-oxabicyclo[2.2.1]hept-2-yl]ethyl]benzoic acid 1N LiOH (6 ml) is added to the title C ester (223 mg, 0.59 mmol) in THF (30 ml) and H₂O (6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na₂SO₄. Filtration and evaporation of solvent yield an oil which is purified by a silica gel column (silica 60, 20 g) eluted with CH₂Cl₂/MeOH (9.4/0.6) to give the title product.

EXAMPLE 101

[1β,2α,3β,4β]-4-[2-[3-[[2-(1-Oxopentyl)hydrazino]methyl]-7-oxabicyclo[2.2.1]hept-2-yl]ethyl]benzoic acid

A.

[1β,2α,3β,4β]-4-[2-[3-[[(1-Oxopentyl)hydrazono]methyl]-7-oxabicyclo[2.2.1]hept-2-yl]ethyl]benzoic acid, methyl ester A solution of [1β,2α,3β,4β]-4-[2-[3-formyl-7-oxabicyclo[2.2.1]hept-2-yl]ethyl]benzoic acid, methyl ester (2 mmol) and pentanoyl hydrazide (prepared as described in Example 100, Part A) (255.1 mg, 2.2 mmol) in EtOH (10 ml) is stirred at room temperature for 2 hours. The reaction mixture is poured into 100 ml of ether and washed with 1N HCl (2×20 ml), saturated NaHCO₃ solution (2×20 ml) and saturated NaCl solution (2×20 ml). The ether solution is dried over MgSO₄, filtered and freed of solvent in vacuo leaving an oil. This is chromatographed on 30 g silica gel 60, eluting with ether to give the title A compound.

B.

[1β,2α,3β,4β]-4-[2-[3-[[2-(1-Oxopentyl)hydrazino]methyl]-7-oxabicyclo[2.2.1]hept-2-yl]ethyl]benzoic acid, methyl ester Following the procedure of Example 100 Part C but substituting the above Part A hydrazono compound for the Example 102 title E compound, the above title B compound is obtained.

C.

[1β,2α,3β,4β]-4-[2-[3-[[2-(1-Oxopentyl)hydrazino]methyl]-7-oxabicyclo[2.2.1]hept-2-yl]ethyl]benzoic acid Following the procedure of Example 100 Part D but substituting the Part B methyl ester for the Example 103 Part F methyl ester, the title acid product is obtained.

EXAMPLE 102

[1β,2α,3α,2β]-4-[2-[3-[[2-(1-Oxopentyl)hydrazino]methyl]-7-oxabicyclo[2.2.1]hept-2-yl]ethyl]benzoic acid

A. Pentanoyl hydrazine

The title compound is prepared as described in Example 100A. B. [1β,2α,3α,4β[-4-[2-[3-[[(1-Oxopentyl)hydrazono]methyl]-7-oxabicyclo[2.2.1]hept-2-yl]ethyl]benzoic acid, methyl ester

[1β,2α,3α,4β]-4-[2-[3-Formyl-7-oxabicyclo[2.2.1]hept-2-yl]ethyl]benzoic acid, methyl ester (2 mmol) and the title A hydrazide (255.2 mg, 2.2 mmol) are stirred in EtOH (10 ml) at room temperature for 1 hour. The reaction is poured into Et$_2$O (150 ml), which is washed with 1N HCl (30 ml×2), saturated NaHCO$_3$ (30 ml×2), brine (30 ml×2), dried over MgSO$_4$. Filtration and evaporation of solvent give a viscous oil, which is purified by silica gel column eluted with Et$_2$O/EtOAc—4/1 to give an oil.

C.
[1β,2α,3α,4β]-4-[2-[3-[[2-(1-Oxopentyl)hydrazino]methyl]-7-oxabicyclo[2.2.1]hept-2-yl]ethyl]benzoic acid, methyl ester To 2.2 mmoles of the title B hydrazono compound dissolved in 20 ml ethyl acetate is added, under an argon atmosphere, 160 mg of 5% Pd on carbon. The argon atmosphere is exchanged for a slight positive pressure of hydrogen and the reaction is stirred for 8 hours at 25° C., filtered through a celite plug and evaporated to provide the title compound.

D.
[1β,2α,3α,4β]-4-[2-[3-[[2-(1-Oxopentyl)hydrazino]methyl]-7-oxabicyclo[2.2.1]hept-2-yl]ethyl]benzoic acid Following the procedure of Example 100 Part D but substituting the Part C methyl ester for the Example 100 Part C methyl ester, the title acid product is obtained.

Example 103

[1β,2α,3α,4β]-4-[2-[3-[[(Pentyloxy)amino]methyl]-7-oxabicyclo[2.2.1]hept-2-yl]ethyl]benzoic acid A. Ethyl N-hydroxyurethane H$_2$N-OH.HCl (27.8 g, 0.40 mol) was added portionwise to a solution of Na$_2$CO$_3$ (62.4 gm, 0.59 mol) in H$_2$O (184 ml) under vigorous magnetic stirring. The reaction was endothermic and gave a white solid suspension. Then, ethyl chloroformate (42.4 g) was added dropwise at 0° C. in an ice bath. After completing the addition, the reaction was warmed to room temperature and stirring was continued for 1.5 hours. The reaction was acidified to pH 2 by addition of concentrated HCl. The products were extracted into Et$_2$O by a continuous liquid-liquid extractor (24 hours). The ether layer was dried over MgSO$_4$. Filtration and evaporation of solvent in vacuo yielded the title compound in the form of a clear yellow oil (37.3 g, 0.355 mol, 89%). The crude product was pure enough for a next reaction, so that no purification was attempted.

B. Ethyl O-pentyl-N-hydroxyurethane

KOH (6.6 g, 0.12 mol) dissolved in EtOH (30 ml) was added to 1-bromopentane (15.4 g, 0.1 mol) and ethyl N-hydroxyurethane (prepared as described in Part A, 10.5 g, 0.1 mol). The reaction was heated at reflux for 6 hours. The reaction was poured into ether (400 ml), and the resulting solids were filtered. The filtrate was washed with saturated NH$_4$Cl and dried over MgSO$_4$. Filtration and evaporation of solvents in vacuo gave a colorless liquid (14.3 g) which was distilled to afford the title compound in the form of a colorless oil (10.6 g, 0.061 mol, b.p. 91° C./2.75 mHg, 61%).

C. O-Pentylhydroxyamino hydrochloride

Ethyl O-pentyl-N-hydroxyurethane, prepared as described in Part B, (10.6 g, 0.061 mol) and KOH (13.6 g, 0.242 mol) in H$_2$O (65 ml) were heated at reflux for 4 hours. The products was extracted into ether (150 ml×3). The combined ether layers were washed with 2N HCl (100 ml). Then, the water layer was washed with Et$_2$O (100 ml) and evaporated off in vacuo to give white solid (6.8 g). MeOH (50 ml) was added to dissolve most of the solid. Undissolved solid was removed by filtration and the filtrate was evaporated in vacuo to give the title compound in the form of a white solid (6.5 g, 46 mmol, 77%).

D.
[1β,2α,3α,4β]-4-[2-[3-[[(Pentyloxy)imino]methyl]-7-oxabicyclo[2.2.1]hept-2-yl]ethyl]benzoic acid, methyl ester O-pentylhydroxyamino hydrochloride (306.9 mg, 2.2 mmol) is added to a suspension of NaOAc (196.8 mg, 2.4 mmol) in dry EtOH (10 ml). NaCl is immediately precipitated out. Then, [1β,2α,3α,4β]-4-[2-[3-formyl-7-oxabicyclo[2.2.1]hept-2-yl]ethyl]benzoic acid, methyl ester (2.0 mmol) in dry EtOH (1 ml) is added at room temperature. After 1 hour stirring, the reaction mixture is poured into Et$_2$O, which is washed with 1N HCl (20 ml×2), saturated NaHCO$_3$ (20 ml×2), brine (20 ml×2) and dried over MgSO$_4$. Filtration and evaporation of solvents in vacuo give an oil, which is purified by column chromatography (silica 60, 30 g) eluted with ether/pet. ether (1:2) to give the title compound.

E.
[1β,2α,3α,4β]-4-[2-[3-[[(Pentyloxy)amino]methyl]-7-oxabicyclo[2.2.1]hept-2-yl]ethyl]benzoic acid, methyl ester NaBH$_3$CN (57 mg, 0.92 mmol) is added to a magnetically stirred solution of Part D oxime (0.71 mmol) in MeOH (8.5 ml), followed by addition of AcOH (1.5 ml) dropwise. After 2¼ hours stirring at room temperature, additional NaBH$_3$CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basified by addition of saturated NaHCO$_3$. The products are extracted with Et$_2$O (100×2). The combined ether layers are washed with brine and dried over MgSO$_4$. Filtration and evaporation of solvent gives the title compound in the form of a colorless oil, which is purified by a silica gel column (silica 60, 15 g) eluted with ether/pet ether (1/1) to give a colorless oil.

F.
[1β,2α,3α,4β]-4-[2-[3-[[(Pentyloxy)amino]methyl]-7-oxabicyclo[2.2.1]hept-2-yl]ethyl]benzoic acid 1N LiOH (6 ml) is added to the title E ester (0.59 mmol) in THF (30 ml) and H$_2$O (6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na$_2$SO$_4$. Filtration and evaporation of solvent yield an oil which is purified by a silica gel column (silica 60, 20 g) eluted with CH$_2$Cl$_2$/MeOH (9.4/0.6) to give the title product.

EXAMPLE 104

[1β,2α,3α,4β[-4-[2-[3-[[(Pentyloxy)amino]methyl]-7-oxabicyclo[2.2.1]hept-2-yl]ethyl]benzoic acid

A.
[1β,2α,3α,4β]-4-[2-[3-[[(Pentyloxy)imino]methyl]-7-oxabicyclo[2.2.1]hept-2-yl]ethyl]benzoic acid Following the procedure of Example 100 except substituting [1β,2α,3α,4β]-4-[2-[3-formyl-7-oxabicyclo[2.2.1]hept-2-yl]ethyl]benzoic acid, methyl ester for the aldehyde used in Example 100 Part B, the title product is obtained.

B.
[1β,2α,3α,4β]-4-[2-[3-[[(Pentyloxy)amino]methyl]-7-oxabicyclo[2.2.1]hept-2-yl]ethyl]benzoic acid, methyl ester NaBH$_3$CN (57 mg, 0.92 mmol) is added to a magnetically stirred solution of Part A oxime (0.71 mmol) in MeOH (8.5 ml), followed by addition of AcOH (1.5 ml) dropwise. After 2¼ hours stirring at room temperature, additional NaBH$_3$CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basified by addition of saturated NaHCO$_3$. The products are extracted with Et$_2$O (100 ml×2). The combined ether layers are washed with brine and dried over MgSO$_4$. Filtration and evaporation of solvent gives the title compound, which is purified by a silica gel column (silica 60, 15 g) eluted with ether/pet ether (1/1) to give a colorless oil.

C.
[1β,2α,3α,4β]-4-[2-[3-[[(Pentyloxy)amino]methyl]-7-oxabicyclo[2.2.1]hept-2-yl]ethyl]benzoic acid 1N LiOH (6 ml) is added to the title B ester (0.59 mmol) in THF (30 ml) and H$_2$O (6 ml) at room temperature. After 6 hours stirring at room temperature, the reaction is quenched by addition of 1N HCl (6 ml) and poured into brine (20 ml). The products are extracted with ether (100 ml33 3). The combined ether layers are washed with brine (50 ml×3) and dried over Na$_2$SO$_4$. Filtration and evaporation of solvent yield an oil which is purified by a silica gel column (silica 60, 20 g) eluted with CH$_2$Cl$_2$/MeOH (9.4/0.6) to give the title product.

EXAMPLE 105

[1β,2α,3α,4β]-4-[2-[3-[[2-(Propoxycarbonyl)hydrazino]methyl]-7-oxabicyclo[2.2.1]hept-2-yl]ethyl]benzoic acid

A.
[1β,2α,3α,4β]-4-[2-[3-[[(Propoxycarbonyl)hydrazono]methyl]-7-oxabicyclo[2.2.1]hept-2-yl]ethyl]benzoic acid, methyl ester

[1β,2α,3α,4β]-4-[2-[3-Formyl-7-oxabicyclo[2.2.1]hept-2-yl]benzoic acid, methyl ester, (2 mmol) and n-propyl hydrazinocarboxylate (prepared by refluxing hydrazine hydrate (1.9 g, 0.038 mmol) and di-n-propyl carbonate (5.3 g, 0.036 mmol) for 43 hours), 283.2 mg, 2.4 mmol, are dissolved in EtOH (10 ml) and the reaction is stirred for 2 hours at room temperature. The reaction is concentrated in vacuo leaving an oil, which is purified by silica gel column (silica 60, 30 g) eluted with Et$_2$O/pet ether (3.5/1.5) to give the title compound.

B.
[1β,2α,3α,4β]-4-[2-[3-[[2-(Propoxycarbonyl)hydrazino]methyl]-7-oxabicyclo[2.2.1]hept-2-yl]ethyl]benzoic acid, methyl ester Title A compound (0.96 mmol) is dissolved in methanol (9 ml) and sodium cyanoborohydride (90 mg, 1.43 mmol) is added. Glacial acetic acid (4.5 ml) is then added dropwise in 2 minutes. The mixture is stirred at room temperature for 2.5 hours and then acidified to pH 1 with 1N HCl solution. After stirring at room temperature for 30 minutes the mixture is basified with NaHCO$_3$. The product is extracted into ether (3×60 ml) and washed with saturated NaHCO$_3$ solution (50 ml) and saturated NaCl solution (50 ml), dried (MgSO$_4$) and freed of solvent in vacuo leaving an oil. This is chromatographed on silica gel 60 (20 g) to give the title compound.

C.
[1β,2α,3α,4β]-4-[2-[3-[[2-(Propoxycarbonyl)hydrazino]methyl]-7-oxabicyclo[2.2.1]hept-2-yl]ethyl]benzoic acid The title B methyl ester (0.77 mmol) is dissolved in THF (40 ml) and water (7 ml) in an argon atmosphere. While stirring, 1N LiOH solution (7.7 ml) is added and the mixture is stirred at room temperature 4 hours. 1N HCl solution (7.7 ml) is added to adjust the pH to ~6 and the mixture is poured into saturated NaCl column (200 ml). The product is extracted into ethyl acetate (3×100 ml). The combined ethyl acetate extracts are washed with saturated NaCl solution (4×75 ml), dried (MgSO$_4$) and freed of solvent in vacuo leaving an oil. This is chromatographed using silicar CC7 (25 g), eluting with 2% MeOH in CH$_2$Cl$_2$ to give the title product.

EXAMPLE 106

[1β,2α,3β,4β]-4-[2-[3-[(Phenylamino)methyl]-7-oxabicyclo[2.2.1]hept-2-yl]ethyl]benzoic acid Following the procedure of Example 82 except substituting aniline for hexylamine, the title product is obtained.

EXAMPLE 107

[1β,2α,3α,4β]-4-[2-[3-[(Phenylamino)methyl]-7-oxabicyclo[2.2.1]hept-2-yl]ethyl]benzoic acid Following the procedure of Example 83 except substituting aniline for hexylamine, the title product is obtained.

EXAMPLE 108

[1β,2α,3β,4β]-4-[2-[3-[(Phenylamino)methyl]-7-oxabicyclo[2.2.1]hept-2-yl]ethyl]benzoic acid Following the procedure of Examples 84 and 82 except substituting aniline for hexylamine, the title product is obtained.

EXAMPLE 109

[1β,2α,3β,4β]-4-[2-[3-(Benzylamino)-7-oxabicyclo[2.2.1]hept-2-yl]ethyl]benzoic acid Following the procedure of Example 88 except substituting benzaldehyde for heptanal, the title compound is obtained.

EXAMPLE 110

[1β,2α,3β,4β]-4-[2-[3-[(Benzylamino)methyl]-7-oxabicyclo[2.2.1]hept-2-yl]ethyl]benzoic acid Following the procedure of Example 82 except substituting the benzylamine for hexylamine, the title product is obtained.

EXAMPLE 111

[1β,2α,3α,4β]-4-[2-[3-[(Benzylamino)methyl]-7-oxabicyclo[2.2.1]hept-2-yl]ethyl]benzoic acid Following the procedure of Example 83 except substituting benzylamine for hexylamine, the title product is obtained.

EXAMPLE 112

[1β,2α,3β,4β]-4-[2-[3-[(Benzylamino)methyl]-7-oxabicyclo[2.2.1]hept-2-yl]ethyl]benzoic acid Following the procedure of Examples 84 and 82 except substituting benzylamine for hexylamine, the title product is obtained.

EXAMPLE 113

[1β,2α,3β,4β]-4-[2-[3-(Phenethylamino)-7-oxabicyclo[2.2.1]hept-2-yl]ethyl]benzoic acid Following the procedure of Example 88 except substituting benzeneacetaldehyde for heptanal, the title compound is obtained.

EXAMPLE 114

[1β,2β,3α,4β]-4-[2-[3-[[2-(Phenylcarbonyl)hydrazino]methyl]-7-oxabicyclo[2.2.1]hept-2-yl]ethyl]benzoic acid Following the procedure of Example 100 except substituting benzoyl hydrazine for pentanoyl hydrazine, the title product is obtained.

EXAMPLE 115

[1β,2α,3β,4β]-4-[2-[3-[[2-(Phenylcarbonyl)hydrazino]methyl]-7-oxabicyclo[2.2.1]hept-2-yl]ethyl]benzoic acid Following the procedure of Example 101 except substituting benzoyl hydrazine for pentanoyl hydrazine, the title product is obtained.

EXAMPLE 116

[1β,2β,3α,4β]-4-[2-[3-[[2-(Benzylcarbonyl)hydrazino]methyl]-7-oxabicyclo[2.2.1]hept-2-yl]ethyl]benzoic acid Following the procedure of Example 100 except substituting phenylacetyl hydrazine for pentanoyl hydrazine, the title compound is obtained.

EXAMPLE 117

[1β,2α,3β,4β]-4-[2-[3-[[2-(Benzylcarbonyl)hydrazino]methyl]-7-oxabicyclo[2.2.1]hept-2-yl]ethyl]benzoic acid Following the procedure of Example 101 except substituting phenylacetyl hydrazine for pentanoyl hydrazine, the title compound is obtained.

EXAMPLE 118

[1β,2β,3α,4β]-4-[2-[3-[[2-(Phenoxycarbonyl)hydrazino]methyl]-7-oxabicyclo[2.2.1]hept-2-yl]ethyl]benzoic acid Following the procedure of Example 100 except substituting phenoxycarbonyl hydrazine for pentanoyl hydrazine, the title product is obtained.

EXAMPLE 119

[1β,2α,3β,4β]-4-[2-[3-[[2-(Phenoxycarbonyl)hydrazino]methyl]-7-oxabicyclo[2.2.1]hept-2-yl]ethyl]benzoic acid Following the procedure of Example 101 except substituting phenoxycarbonyl hydrazine for pentanoyl hydrazine, the title compound is obtained.

EXAMPLE 120

[1β,2β,3α,4β]-4-[2-[3-[[2-(Benzyloxycarbonyl)hydrazino]methyl]-7-oxabicyclo[2.2.1]hept-2-yl]ethyl]benzoic acid Following the procedure of Example 100 except substituting benzyloxycarbonyl hydrazine for pentanoyl hydrazine, the title product is obtained.

EXAMPLE 121

[1β,2α,3β,4β]-4-[2-[3-[[2-(Benzyloxycarbonyl)hydrazino]methyl-7-oxabicyclo[2.2.1]hept-2-yl]ethyl]benzoic acid Following the procedure of Example 101 except substituting benzyloxycarbonyl hydrazine for pentanoyl hydrazine, the title compound is obtained.

EXAMPLE 122

[1β,2β,3α,4β]-4-[2-[3-[[2-(Phenylalanyl)hydrazino]methyl]-7-oxabicyclo[2.2.1]hept-2-yl]ethyl]benzoic acid Following the procedure of Example 100 except substituting phenylalanyl hydrazine for pentanoyl hydrazine, the title product is obtained.

EXAMPLE 123

[1β,2α,3β,4β]-4-[2-[3-[[2-(Phenylalanyl)hydrazino]methyl]-7-oxabicyclo[2.2.1]hept-2-yl]ethyl]benzoic acid Following the procedure of Example 101 except substituting phenylalanyl hydrazine for pentanoyl hydrazine, the title compound is obtained.

EXAMPLE 124

[1β,2β,3α,4β]-4-[2-[3-[[2-(Phenylaminocarbonyl)hydrazino]methyl]-7-oxabicyclo[2.2.1]hept-2-yl]ethyl]benzoic acid Following the procedure of Example 100 except substituting 4-phenylsemicarbazide for pentanoyl hydrazine, the title compound is obtained.

EXAMPLE 125

[1β,2α,3β,4β]-4-[2-[3-[[2-(Phenylaminocarbonyl)hydrazino]methyl]-7-oxabicyclo[2.2.1]hept-2-yl]ethyl]benzoic acid Following the procedure of Example 101 except substituting 4-phenylsemicarbazide for pentanoyl hydrazine, the title compound is obtained.

EXAMPLE 126

[1β,2β,3α,4β]-4-[2-[3-[[2-(Propylaminocarbonyl)hydrazino]methyl]-7-oxabicyclo[2.2.1]hept-2-yl]ethyl]benzoic acid Following the procedure of Example 100 except substituting 4-propylsemicarbazide for pentanoyl hydrazine, the title product is obtained.

EXAMPLE 126a

[1β,2α,3β,4β]-4-[2-[3-[[2-(Propylaminocarbonyl)methyl]-7-oxabicyclo[2.2.1]hept-2-yl]ethyl]benzoic acid Following the procedure of Example 101 except substituting 4-propylsemicarbazide for pentanoyl hydrazine, the title compound is obtained.

EXAMPLE 127

[1β,2α,3α(1E),4β]-4-[3-(3-Cyclohexyl-3-hydroxy-1-propenyl)-7-oxabicyclo[2.2.1]hept-2-yl]methyl benzoic acid

A.
4-[[(3-Hydroxymethyl)-7-oxabicyclo[2.2.1]hept-2-yl]hydroxymethyl]styrene and

B.
4-[[(3-Hydroxymethyl)-7-oxabicyclo[2.2.1]hept-2-yl]hydroxymethyl]styrene, diacetate To 747 mg Mg turnings (30.8 mmol, 2.5 eq) in 10 ml of dry THF under an argon atmosphere at 25° C. is added dropwise 5.93 g bromostyrene (32.5 mmol, 2.6 eq) in 20 ml of dry THF. The mixture is stirred for 1 hour. To this Grignard reagent is added at 25° C. 2.6 g (exo)-2-[3-acetoxymethyl-7-oxabicyclo[2.2.1]hept-2-yl]acetaldehyde, (12.3 mmol) in 30 ml of dry THF over a 1 hour period. The reaction mixture is stirred for 30 minutes then quenched with 30 ml of 1N HCl solution and diluted with 1 liter of ether. The ethereal solution is washed with three 100 ml portions of saturated sodium bicarbonate, two 100 ml portions of water, dried over anhydrous magnesium sulfate and then concentrated to yield title A compound as an oil.

A solution of the above title A compound, 130.5 g of triethylamine (1.28 mole, 104 eq), 984 mg 4-dimethyl amino pyridine (8.12 mmole, 0.66 eq) and 66.3 g acetic anhydride (0.64 mole, 52 eq) is stirred at 25° C. for 30 minutes. The mixture is concentrated under vacuum then poured into 100 ml of an ice-water mixture. The aqueous solution is extracted with four 200 ml portions of $CH_2Cl_2$. The combined organic layer is dried over anhydrous magnesium sulfate and concentrated to give a crude oil.

This crude oil is purified on a LPS-1 silica gel column, eluting with 2 liters of 10% EtOAc/hexane and 1 liter of 50% EtOAc/hexane to yield title B diacetate compound as an oil.

C.
[1β,2α,3α,4β]-4-[[3-Acetoxymethyl-7-oxabicyclo[2.2.1]hept-2-yl]acetoxymethyl]benzoic acid and

D.
[1β,2α,3α,4β]-4-[[3-Acetoxymethyl-7-oxabicyclo[2.2.1]hept-2-yl]acetoxymethyl]benzoic acid, methyl ester To title B diacetate (8.1 mmole) in 20 ml acetonitrile, 20 ml of carbon tetrachloride, 30 ml of water is added at 25° C. 7.14 g sodium periodate (33.2 mmole, 4.1 eq) and 44.8 mg ruthenium (III) chloride trihydrate (0.15 mmole, 2.2%). The mixture is stirred at 25° C. for 2 hours and then diluted with 20 ml of $CH_2Cl_2$. The aqueous layer is extracted with three 50 ml portions of $CH_2Cl_2$. The combined organic layer is dried over anhydrous magnesium sulfate and concentrated. The residue is diluted with 300 ml of ether and filtered through a bed of Celite. The filtrate is concentrated to give title C compound as an oil.

This oil is treated with excess diazomethane in ether to give 2.6 g of a crude oil.

This crude oil is purified on a LPS 1 silica gel column, eluting with 20% EtOAc/hexane to give pure ester title D compound.

E.
[1β,2α,3α,4β]-4-[[3-Acetoxymethyl-7-oxabicyclo[2.2.1]hept-2-yl]methyl]benzoic acid, methyl ester A mixture of title D compound and 1.5 g of 10% palladium on carbon in 100 ml of glacial acetic acid is shaken in a Parr bottle at 25° C. under 50 psi hydrogen pressure for 6 hours. The mixture is filtered through a bed of Celite and concentrated to give title E compound as a clear oil.

F.
[1β,2α,3α,4β]-4-[[3-Hydroxymethyl-7-oxabicyclo[2.2.1]hept-2-yl]methyl]benzoic acid, methyl ester To title E compound (2.79 mmole) in 20 ml of methanol is added 460 mg of potassium carbonate (3.34 mmole, 1.2 eq). The mixture is stirred under an argon atmosphere at 25° C. for 1 hour. The reaction mixture is poured into 200 ml of saturated ammonium chloride, then extracted with three 200 ml portions of ether. The ethereal extracts are washed with 100 ml of brine, dried over anhydrous magnesium sulfate and concentrated to give title F compound as a white solid.

G.
[1β,2α,3α,4β]-4-[[3-Formyl-7-oxabicyclo[2.2.1]hept-2-yl]methyl]benzoic acid, methyl ester A mixture of chromium trioxide (1.56 g, 15.6 mmole, 6 eq) pyridine (2.47 g, 31.3 mmole, 12 eq) in 100 ml of $CH_2Cl_2$ is stirred under an argon atmosphere at 25° C. for 30 minutes. Dry Celite (5.0 g) is added, followed by a solution of title F compound (2.61 mmole) in 50 ml $CH_2Cl_2$. The reaction mixture is stirred for 30 minutes then filtered with 300 ml $CH_2Cl_2$. The filtrate is washed with three 100 ml portions of 5% sodium bicarbonate, 100 ml of 10% hydrochloric acid, 100 ml of saturated sodium bicarbonate, dried over anhydrous magnesium sulfate, then filtered through a bed of florosil and concentrated.

The residue is purified by flash chromatography on a LPS-1 silica gel column, eluting with 20% EtOAc/hexane to yield title G compound as a white solid.

H.
[1β,2α,3α(1E),4β]-4-[[3-(3-Cyclohexyl-3-oxo-1-propenyl)-7-oxabicyclo[2.2.1]hept-2-yl]methyl]benzoic acid, methyl ester To a slurry of 99 mg of 50% sodium hydride in mineral oil (200 mmole, 1.1 eq) in 30 ml of anhydrous dimethoxy ethane (DME) is added 702.8 mg of 2-oxo-2-cyclohexylethyldimethylphosphonate (3.0 mmole, 1.6 eq) in 10 ml of DME at 0° C. under an argon atmosphere. The mixture is stirred under argon at 25° C. for 1 hour. To this solution at 25° C. is added title G compound (1.88 mmole) in 10 ml of DME. After 60 minutes, the reaction is quenched with 2 ml of glacial acetic acid, concentrated and dissolved in 200 ml of ether. The ethereal solution is washed with three 50 ml portions of 5% potassium bicarbonate and dried over anhydrous magnesium sulfate and concentrated to give a crude oil.

This oil is purified by flash chromatography on a LPS-1 silica gel column eluting with 10% EtOAc in hexanes to yield title H compound as a white solid.

I.
[1β,2α,3α(1E),4β]-4-[[3-(3-Cyclohexyl-3-hydroxy-1-propenyl)-7-oxabicyclo[2.2.1]hept-2-yl]methyl]benzoic acid, methyl ester (fast moving isomer) and

J.
[1β,2α,3α(1E),4β]-4-[[3-(3-Cyclohexyl-3-hydroxy-1-propenyl)-7-oxabicyclo[2.2.1]hept-2-yl]methyl]benzoic acid, methyl ester (slow moving isomer)

To a solution of 587 mg of title H compound in 15 ml of dry methanol is added at 25° C. under an argon atmosphere 578 mg of cerium chloride containing 25.7% water (1.49 mmole, 1 eq). The reaction is stirred for 10 minutes at 25° C., cooled to 0° C. and 56.6 mg of sodium borohydride (1.49 mmole, 4 eq) is slowly added. After stirring for 10 minutes at 0° C., the reaction mixture is poured into 100 ml of saturated ammonium chloride. The mixture is extracted with three 150 ml portions of ether. The ethereal extracts are washed with three 50 ml portions of water and 50 ml of brine. The organic layer is dried over anhydrous magnesium sulfate and concentrated.

Separation and purification is done on LPS-1 silica gel column eluting with 25% ethyl acetate in hexane to give title I compound and title J compound.

K.
[1β,2α,3α(1E),4β]-4-[[3-(3-Cyclohexyl-3-hydroxy-1-propenyl)-7-oxabicyclo[2.2.1]hept-2-yl]methyl]benzoic acid 365 Mg of title I alcohol ester (0.92 mmole) is dissolved in 30 ml of an 80% tetrahydrofuran-water solution and 19 ml of a 1N potassium hydroxide solution is added dropwise. The reaction is stirred at 25° C., then warmed up to 50° C. over a 48 hour period. The THF is evaporated under high vacuum and the residue is diluted with 20 ml of water, acidified to pH 3 with a 10% aqueous oxalic acid solution and extracted with three 60 ml portions of ether. The organic layer is washed with three 30 ml portions of water and 30 ml of brine. The product is dried over anhydrous magnesium sulfate and concentrated to give a white solid.

This is filtered through a polycarbonate membrane. The solvents are evaporated under high vacuum for 2 days to give title product.

EXAMPLE 128
[1β,2α,3α(1E),4β]-4-[[3-(3-Hydroxy-4-phenoxy-1-butenyl)-7-oxabicyclo[2.2.1]hept-2-yl]methyl]benzoic acid Following the procedure of Example 15 except substituting [1β,2α,3α,4β]-4-[[3-formyl-7-oxabicyclo[2.2.1]hept-2-yl]methyl]benzoic acid, methyl ester prepared as described in Example 127 for [1β,2α,3α,4β]-4-[2-[3-formyl-7-oxabicyclo[2.2.1]hept-2-yl]ethyl]benzoic acid, methyl ester, the title compound is obtained.

EXAMPLE 129
[1β,2α,3α,4β]-4-[[3-(3-Hydroxy-4-phenyl-1-pentenyl)-7-oxabicyclo[2.2.1]hept-2-yl]methyl]benzoic acid Following the procedure of Example 17 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 130
[1β,2α,3α,4β]-4-[[3-(3-Hydroxy-4-(2-methylphenyl)-1-butenyl]-7-oxabicyclo[2.2.1]hept-2-yl]methyl]benzoic acid Following the procedure of Example 23 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 131
[1β,2α,3α,4β]-4-[[3-(3-Hydroxy-4-methyl-4-phenyl-1-pentenyl)-7-oxabicyclo[2.2.1]hept-2-yl]methyl]benzoic acid Following the procedure of Example 27 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 132
[1β,2α,3α,4β]-4-[[3-[3-Hydroxy-3-(1-methylcyclohexyl)-1-propenyl]-7-oxabicyclo[2.2.1]hept-2-yl]methyl]benzoic acid Following the procedure of Example 29 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 133
[1β,2α,3α,4β]-4-[[3-(3-Hydroxy-4-phenyl-1-hexenyl)-7-oxabicyclo[2.2.1]hept-2-yl]methyl]benzoic acid Following the procedure of Example 33 except substituting [1β,2α,3α,4β]-4-[[3-formyl-7-oxabicyclo[2.2.1]hept-2-yl]methyl]benzoic acid, methyl ester (prepared as described in Example 33) for [1β,2α,3α,4β]-4-[2-[3-formyl-7-oxabicyclo[2.2.1]hept-2-yl]ethyl]benzoic acid, methyl ester, the title compound is obtained.

EXAMPLE 134
[1β,2α,3β,4β]-4-[3-[[(Propoxycarbonyl)hydrazono]methyl]-7-oxabicyclo[2.2.1]hept-2-yl]methyl]benzoic acid

A.
[1β,2α,3β,4β]-4-[[3-Formyl-7-oxabicyclo[2.2.1]hept-2-yl]methyl]benzoic acid, methyl ester The aldehyde from Example 127, Part G, namely, [1β,2α,3α,4β]-4-[[3-formyl-7-oxabicyclo[2.2.1]hept-2-yl]methyl]benzoic acid, methyl ester, is dissolved in 10 ml of methanol and to this solution is added 27 mg of sodium methoxide. The reaction is stirred at 25° C. for 2 hours, then poured into 300 ml of saturated ammonium chloride and extracted with three 100 ml portions of ether. The combined ethereal extract is washed with 50 ml of brine, dried over anhydrous magnesium sulfate and concentrated to give the title aldehyde.

B.
[1β,2α,3β,4β]-4-[[3-[[(Propoxycarbonyl)hydrazono]-methyl]-7-oxabicyclo[2.2.1]hept-2-yl]methyl]benzoic acid Following the procedure of Example 36 except substituting [1β,2α,3β,4β]-4-[[3-formyl-7-oxabicyclo[2.2.1]hept-2-yl]methyl]benzoic acid, methyl ester (prepared as described above) for [1β,2α,3β,4β]-4-[2-[3-formyl-7-oxabicyclo[2.2.1]hept-2-yl]ethyl]benzoic acid, methyl ester, the title compound is obtained.

EXAMPLE 135
[1β,2α,3α,4β]-4-[[3-[[(Propoxycarbonyl)hydrazono]-methyl]-7-oxabicyclo[2.2.1]hept-2-yl]methyl]benzoic acid Following the procedure of Example 37 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 136
[1β,2α,3α,4β]-4-[[3-[[(Propoxycarbonyl)methylhydrazono]methyl]-7-oxabicyclo[2.2.1]-hept-2-yl]methyl]benzoic acid Following the procedure of Example 38 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 137
[1β,2α,3β,4β]-4-[[3-[[(Propoxycarbonyl)methylhydrazono]methyl]-7-oxabicyclo[2.2.1]hept-2-yl]methyl]benzoic acid Following the procedure of Example 39 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 138
[1β,2α,3α,4β]-4-[[3-[[(1-Oxopentyl)methylhydrazono]-methyl]-7-oxabicyclo[2.2.1]hept-2-yl]methyl]benzoic acid Following the procedure of Example 41 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 139
[1β,2α,3β,4β]-4-[[3-[(Ethylbenzoylhydrazono)methyl]-7-oxabicyclo[2.2.1]hept-2-yl]methyl]benzoic acid Following the procedure of Example 42 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 140
[1β,2α,3α,4β]-4-[[3-(Ethylbenzoylhydrazono)methyl]-7-oxabicyclo[2.2.1]hept-2-yl]methyl]benzoic acid Following the procedure of Example 43 except substituting [1β,2α,3β,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 141
[1β,2α,3β,4β]-4-[[3-[[(Phenylamino)carbonyl]methyl]-7-oxabicyclo[2.2.1]hept-2-yl]methyl]benzoic acid Following the procedure of Example 44 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 142
[1β,2α,3α,4β]-4-[[3-[(3-Pyridinylcarbonyl)methyl]-7-oxabicyclo[2.2.1]hept-2-yl]methyl]benzoic acid Following the procedure of Example 46 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 143
[1β,2α,3α,4β]-4-[[3-[[(Cyclohexylcarbonyl)methylhydrazono]methyl]-7-oxabicyclo[2.2.1]hept-2-yl]methyl]benzoic acid Following the procedure of Example 49 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 144
[1β,2α,3α,4β]-4-[[3-[[(2-Oxo-1-piperidinyl)imino]methyl]-7-oxabicyclo[2.2.1]hept-2-yl]methyl]benzoic acid Following the procedure of Example 50 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 145
[1β,2α,3β,4β]-4-[[3-[[(Phenoxycarbonyl)methylhydrazono]methyl]-7-oxabicyclo[2.2.1]hept-2-yl]methyl]benzoic acid Following the procedure of Example 52 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 146

[1β,2α,3β,4β]-4-[[3-[[(1-Oxohexyl)methyl]hydrazono]-methyl]-7-oxabicyclo[2.2.1]hept-2-yl]methyl]benzoic acid Following the procedure of Example 54 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 147

[1β,2α,3α,4β]-4-[[3-[[[(n-Butylamino)carbonyl]ethylhydrazono]methyl]-7-oxabicyclo[2.2.1]hept-2-yl]methyl]benzoic acid Following the procedure of Example 56 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 148

[1β,2α,3α,4β]-4-[[3-[[(Pentyloxy)imino]methyl]-7-oxabicyclo[2.2.1]hept-2-yl]methyl]benzoic acid Following the procedure of Example 67 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 149

[1β,2α,3α,4β]-4-[[3-[[(Pentyloxy)imino]methyl]-7-oxabicyclo[2.2.1]hept-2-yl]methyl]benzoic acid Following the procedure of Example 68 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 150

[1β,2α,3α,4β]-4-[[3-[[(Phenylmethoxy)imino]methyl]-7-oxabicyclo[2.2.1]hept-2-yl]methyl]benzoic acid Following the procedure of Example 69 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 151

[1β,2α,3β,4β]-4-[[3-[[(Phenylmethoxy)imino]methyl]-7-oxabicyclo[2.2.1]hept-2-yl]methyl]benzoic acid Following the procedure of Example 70 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 152

[1β,2α,3α,4β]-4-[[3-[[(Cyclohexyloxy)imino]methyl]-7-oxabicyclo[2.2.1]hept-2-yl]methyl]benzoic acid Following the procedure of Example 75 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 153

[1β,2α,3β,4β]-4-[[3-[(Hexylamino)methyl]-7-oxabicyclo[2.2.1]hept-2-yl]methyl]benzoic acid Following the procedure of Example 82 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 154

[1β,2α,3α,4β]-4-[[3-[(Hexylamino)methyl]-7-oxabicyclo[2.2.1]hept-2-yl]methyl]benzoic acid Following the procedure of Example 83 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 155

[1β,2α,3α,4β]-4-[[3-[[(Phenylmethoxy)amino]methyl]-7-oxabicyclo[2.2.1]hept-2-yl]methyl]benzoic acid Following the procedure of Example 85 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 156

[1β,2α,3β,4β]-4-[[3-[(Phenylmethoxyamino)methyl]-7-oxabicyclo[2.2.1]hept-2-yl]methyl]benzoic acid Following the procedure of Example 86 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 157

[1β,2α,3β,4β]-4-[[3-(Heptylamino)-7-oxabicyclo[2.2.1]hept-2-yl]methyl]benzoic acid Following the procedure of Example 88 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 158

[1β,2α,3α,4β]-4-[[3-(Heptylamino)-7-oxabicyclo[2.2.1-]hept-2-yl]methyl]benzoic acid Following the procedure of Example 89 except substituting [1β,2α,3α,4β]-4-[[3-formyl-7-oxabicyclo[2.2.1-]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 159

[1β,2α,3β,4β]-4-[[3-[[2-(1-Oxopentyl)hydrazino]methyl-7-oxabicyclo[2.2.1]hept-2-yl]methyl]benzoic acid Following the procedure of Example 101 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

EXAMPLE 160

[1β,2α,3α,4β]-4-[[3-[[2-(1-Oxopentyl)hydrazino]methyl]-7-oxabicyclo[2.2.1]hept-2-yl]methyl]benzoic acid Following the procedure of Example 102 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]-hept-2-yl]ethyl]benzoic acid, methyl ester, the title compound is obtained.

EXAMPLE 161

[1β,2α,3α,4β]-4-[[3-[(Pentyloxyamino)methyl]-7-oxabicyclo[2.2.1]hept-2-yl]methyl]benzoic acid Following the procedure of Example 104 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 162

[1β,2α,3α,4β]-4-[[3-[[2-(Propoxycarbonyl)hydrazino]-methyl]-7-oxabicyclo[2.2.1]hept-2-yl]methyl]benzoic acid Following the procedure of Example 105 except substituting [1β,2α,3α,4β]-4-[[3-formyl-7-oxabicyclo[2.2.1]hept-2-yl]methyl]benzoic acid, methyl ester (prepared as described in Example 127) for [1β,2α,3α,4β]-4-[2-[3-formyl-7-oxabicyclo[2.2.1]hept-2-yl]ethyl]benzoic acid, methyl ester, the title compound is obtained.

EXAMPLE 163

[1β,2α,3β,4β]-4-[[3-[(Phenylamino)methyl]-7-oxabicyclo[2.2.1]hept-2-yl]methyl]benzoic acid Following the procedure of Example 106 except substituting [1β,2α,3β,4β]-4-[[3-formyl-7-oxabicyclo[2.2.1]hept-2-yl]methyl]benzoic acid, methyl ester (prepared as described in Example 134) for [1β,2α,3β,4β]-4-[2-[3-formyl-7-oxabicyclo[2.2.1]hept-2-yl]ethyl]benzoic acid, methyl ester, the title compound is obtained.

What is claimed is:

1. A compound having the structural formula

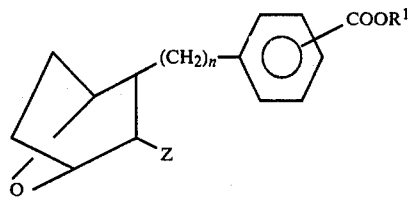

and including all stereoisomers thereof; wherein Z is

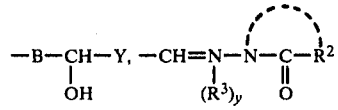

n is 1 or 2;
$R^1$ is H or lower alkyl;
B is —CH=CH—, —C≡C— or $(CH_2)_2$;
Y is alkyl; aryl-lower alkyl; alkenyl; alkynyl; aryl, pyridyl, pyridyl-lower alkyl; substituted pyridyl wherein the substituent is 1 or 2 halogen or lower alkyl groups; thienyl; thienylalkyl; substituted thienyl wherein the substituent is 1 or 2 halogen or lower alkyl groups; cycloalkyl; substituted cycloalkyl wherein the substituent is 1 or 2 halogens, 1 or 2 lower alkyl groups or lower alkoxy groups; cycloalkylalkyl or substituted cycloalkylalkyl wherein the substituent is 1 or 2 halogens, 1 or 2 lower alkyl groups or lower alkoxy groups;
y is 0 or 1,
where y is 1, $R^3$ is H or lower alkyl;
$R^2$ is lower alkyl, lower alkoxy, aryl, alkylamino, arylamino, aryloxy, pyridinyl or cycloalkyl or where y is 0 as indicated by

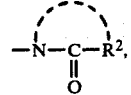

$R^2$ can be a —$(CH_2)_x$ linking group (wherein x is 3, 4 or 5) which together with

may form an N-containing 5-, 6- or 7-membered heterocycle, with the proviso that when $R^3$ is H, $R^2$ is lower alkoxy;
$R^4$ is lower alkyl, cycloalkyl, aryl, aryl-alkyl or alkanoyl;
p is 0 to 5;
m is 1 to 8; and
$R^5$ is lower alkyl, lower alkoxy, aralkoxy or

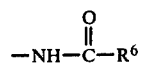

wherein $R^6$ is lower alkyl or phenyl; wherein alkyl or lower alkyl by itself or part of another group contains 1 to 12 carbons, aryl by itself or part of another part refers to a monocyclic or bicyclic aromatic group which contains 6 to 10 carbon atoms in the ring and which ring may be unsubstituted or contain 1 or 2 halogen, lower alkyl and/or lower alkoxy groups, alkenyl contains 3 to 6 carbon atoms, alkynyl contains 3 to 6 carbon atoms, and cycloalkyl contains 3 to 6 carbon atoms, and cycloalkyl contains 3 to 12 carbon atoms in the ring.

2. The compound as defined in claim 1 wherein n is 2.

3. The compound as defined in claim 1 wherein n is 1.

4. The compound as defined in claim 1 wherein COOR$^1$ is in the para position and R$^1$ is H.

5. The compound as defined in claim 1 having the formula

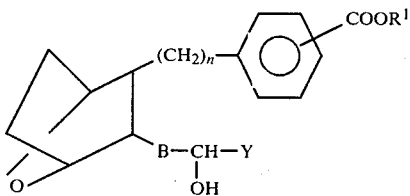

including all stereoisomers thereof.

6. The compound as defined in claim 1 having the formula

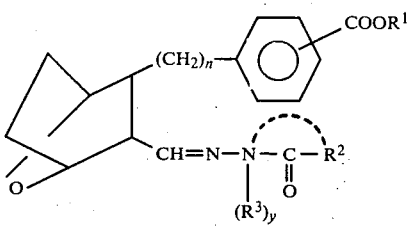

including all stereoisomers thereof.

7. The compound as defined in claim 1 having the formula

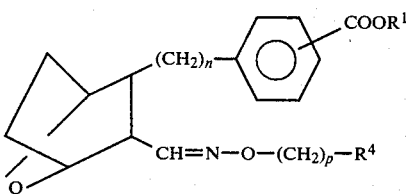

including all stereoisomers thereof.

8. The compound as defined in claim 1 having the formula

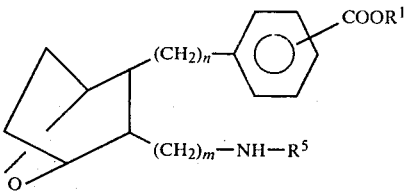

including all stereoisomers thereof.

9. The compound as defined in claim 1 wherein n is 2 and Z is

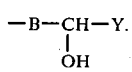

10. The compound as defined in claim 9 wherein B is —CH=CH.

11. The compound as defined in claim 10 wherein Y is cycloalkyl.

12. The compound as defined in claim 10 wherein —COOR$^1$ is in the para-position.

13. The compound as defined in claim 1 having the name [1β,2β,3α(1E),4β]-4-[2-[3-(3-cyclohexyl-3-hydroxy-1-propenyl)-7-oxabicyclo[2.2.1]hept-2-yl]ethyl]benzoic acid or its methyl ester including all isomers of each.

14. The compound as defined in claim 1 having the name [1β,2α,3α(1E),4β]-4-[2-[3-(3-cyclohexyl-3-hydroxy-1-propenyl)-7-oxabicyclo[2.2.1]hept-2-yl]ethyl]benzoic acid or its methyl ester and including all isomers thereof.

15. A method of inhibiting platelet aggregation and bronchoconstriction, which comprises administering to the circulatory system of a mammalian host an effective amount of a compound as defined in claim 1 or a pharmaceutically acceptable salt thereof.

16. The method as defined in claim 15 wherein said compound is administered in an amount within the range of from about 1 to about 100 ml/kg.

17. A composition for inhibiting platelet aggregation and bronchoconstriction comprising an effective amount of a compound as defined in claim 1 or a pharmaceutically acceptable salt thereof, and a pharmaceutically acceptable carrier therefor.

18. A method of inhibiting platelet aggregation which comprises administering to a mammalian host an effective amount of a compound as defined in claim 1 or a pharmaceutically acceptable salt thereof.

19. A method of inhibiting bronchoconstriction associated with asthma, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,463,015

DATED : July 31, 1984

INVENTOR(S) : Martin F. Haslanger et al.

It is certified that error appears in the above—identified patent and that said Letters Patent is hereby corrected as shown below:

Column 1, line 29, "$-(CH_2)_p-$" should read -- $-(CH_2)_m-$ --.

Column 3, after line 53 and before the formula on line 55, insert -- $(CH_2)_z CH_3$ (z is 2 to 4), $CH_2C_6H_5$, --.

Column 7, line 60, structure VIA should read

-- 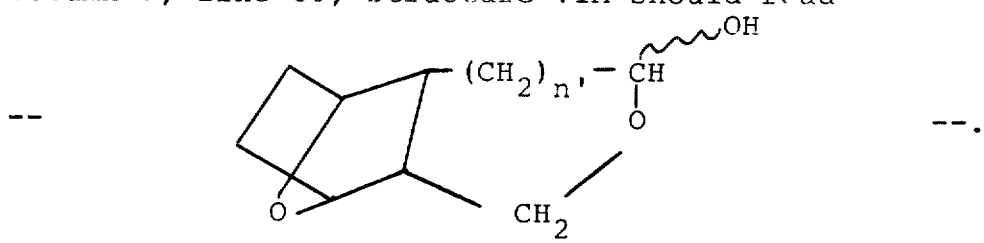 --.

Column 14, line 35, structures IIIc and IIId should read

-- 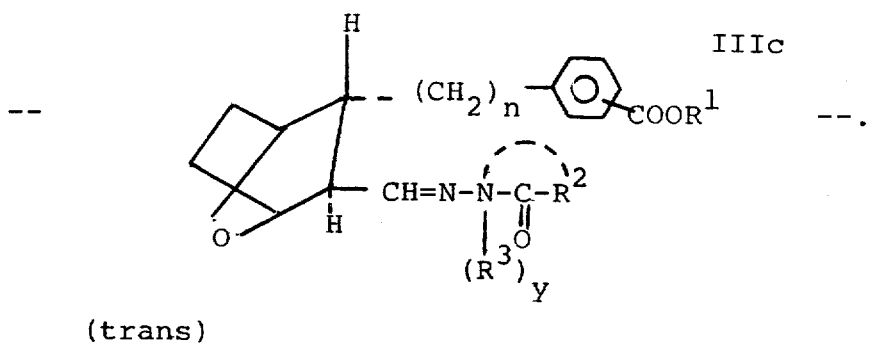 --.

(trans)

UNITED STATES PATENT AND TRADEMARK OFFICE
CERTIFICATE OF CORRECTION

PATENT NO. : 4,463,015

DATED : Martin F. Haslanger et al.

INVENTOR(S) : July 31, 1984

It is certified that error appears in the above—identified patent and that said Letters Patent is hereby corrected as shown below:

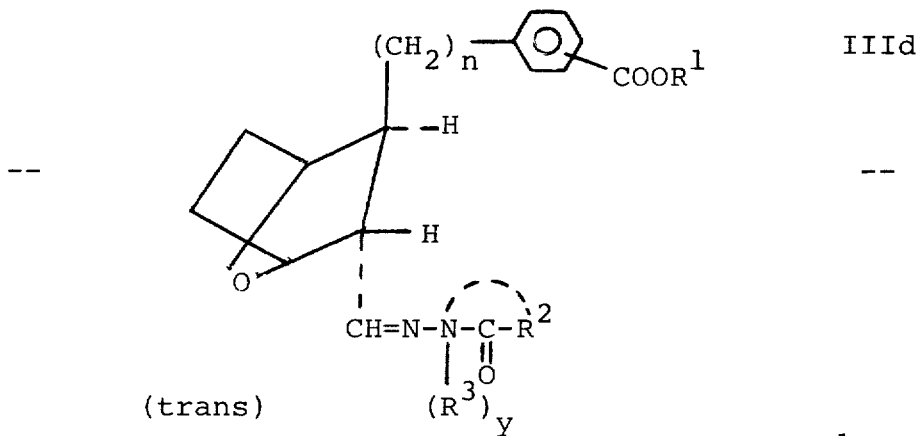

Column 15, after structure XXIV, insert --($R^1$ is lower alkyl)--.
Column 24, line 49, "guenched" should read --quenched--.
Column 38, line 34, "polycarbnate" should read --polycarbonate--.
Column 39, line 2, after "[3-" insert --[3- --.
Column 39, line 7, after "[3-[3-" delete "[3-".
Column 44, line 46, after "[3-" insert --[3- --.
Column 45, line 7, after "hept-2-" insert --yl]--.
Column 46, line 29, "m-tosylacetic" should read --m-tolylacetic--.
Column 46, line 38, "conbined" should read --combined--.
Column 47, line 50, "with ether" should read --into ether--.

UNITED STATES PATENT AND TRADEMARK OFFICE
CERTIFICATE OF CORRECTION

PATENT NO. : 4,463,015
DATED : Martin F. Haslanger et al.
INVENTOR(S) : July 31, 1984

It is certified that error appears in the above—identified patent and that said Letters Patent is hereby corrected as shown below:

Column 55, line 46, "1.16" should read --0.16--.
Column 55, line 56, "propoxycarbony" should read --propoxycarbonyl--.
Column 77, line 43, "100 ml33 3" should read --100 ml x 3--.
Column 87, line 38, "[1β,2α,3α,4β]" should read --[1β,2α,3β,4β]--.
Column 90, after the structures on line 16, insert -- $-CH=N-O-(CH_2)_p-R^4$ or $-(CH_2)_n-NH-R^5$; --.

Column 91, lines 5 and 6, delete "3 to 6 carbon atoms, and cycloalkyl contains".

Signed and Sealed this

Twelfth Day of March 1985

[SEAL]

Attest:

DONALD J. QUIGG

Attesting Officer    Acting Commissioner of Patents and Trademarks